(12) United States Patent
Lee et al.

(10) Patent No.: US 10,003,030 B2
(45) Date of Patent: Jun. 19, 2018

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Hoyong Lee, Daejeon (KR); Kongkyeom Kim, Daejeon (KR); Hyok Joon Kwon, Daejeon (KR); Tae Yoon Park, Daejeon (KR); Jiyeon Ahn, Daejeon (KR); Dongheon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 15/313,004

(22) PCT Filed: May 22, 2015

(86) PCT No.: PCT/KR2015/005212
§ 371 (c)(1),
(2) Date: Nov. 21, 2016

(87) PCT Pub. No.: WO2015/178740
PCT Pub. Date: Nov. 26, 2015

(65) Prior Publication Data
US 2017/0186966 A1    Jun. 29, 2017

(30) Foreign Application Priority Data

May 22, 2014  (KR) .................. 10-2014-0061428

(51) Int. Cl.
| | | |
|---|---|---|
| H01L 51/00 | (2006.01) |
| C07D 495/04 | (2006.01) |
| C07D 493/04 | (2006.01) |
| C09K 11/02 | (2006.01) |
| C09K 11/06 | (2006.01) |
| H01L 51/50 | (2006.01) |

(52) U.S. Cl.
CPC ........ *H01L 51/0067* (2013.01); *C07D 493/04* (2013.01); *C07D 495/04* (2013.01); *C09K 11/025* (2013.01); *C09K 11/06* (2013.01); *H01L 51/0052* (2013.01); *H01L 51/0071* (2013.01); *H01L 51/0072* (2013.01); *H01L 51/0073* (2013.01); *H01L 51/50* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01)

(58) Field of Classification Search
None
See application file for complete search history.

(56) References Cited

U.S. PATENT DOCUMENTS

| | | |
|---|---|---|
| 8,932,732 B2 | 1/2015 | Buesing et al. |
| 9,368,733 B2 | 6/2016 | Ryu et al. |
| 2014/0091298 A1 | 4/2014 | Hong et al. |

FOREIGN PATENT DOCUMENTS

| | | |
|---|---|---|
| CN | 103781876 A | 5/2014 |
| CN | 107075364 A | 8/2017 |
| EP | 3222695 A1 | 9/2017 |
| JP | 2009-267257 A | 11/2009 |
| KR | 10-2011-0102055 A | 9/2011 |

(Continued)

*Primary Examiner* — J. L. Yang
(74) *Attorney, Agent, or Firm* — Dentons US LLP

(57) ABSTRACT

The present specification provides a hetero-cyclic compound and an organic light emitting device including the hetero-cyclic compound.

13 Claims, 1 Drawing Sheet

(56) References Cited

FOREIGN PATENT DOCUMENTS

| | | |
|---|---|---|
| KR | 10-1560102 B1 | 10/2015 |
| WO | 2007/140847 A1 | 12/2007 |
| WO | 2014/051232 A1 | 4/2014 |

[Figure 1]
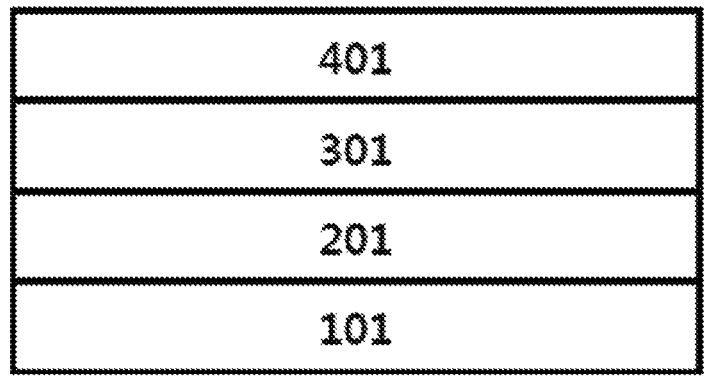
[Figure 2]
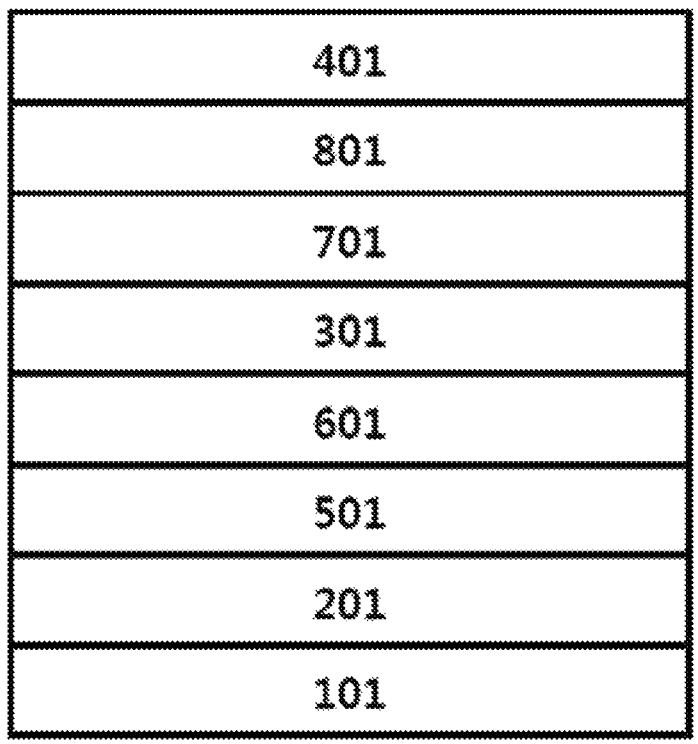

HETEROCYCLIC COMPOUND AND ORGANIC LIGHT EMITTING DEVICE COMPRISING SAME

TECHNICAL FIELD

This application is a National Stage Entry of International Application No. PCT/KR2015/005212, filed May 22, 2015, and claims the benefit of and priority to Korean Application No. 10-2014-0061428 filed on May 22, 2014 all of which are hereby incorporated by reference in their entirety for all purposes as if fully set forth herein.

The present specification relates to a hetero-cyclic compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon typically has a structure including an anode, a cathode, and an organic material layer disposed therebetween. Here, the organic material layer may have a multi-layered structure composed of different materials in order to enhance the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from an anode into the organic material layer and electrons are injected from a cathode into the organic material layer, and when the injected holes and electrons meet each other, an exciton is formed, and light is emitted when the exciton falls down again to a ground state.

There is a continuous need for developing a new material for the aforementioned organic light emitting device.

DISCLOSURE

Technical Problem

An object of the present specification is to provide a hetero-cyclic compound and an organic light emitting device including the same.

Technical Solution

An exemplary embodiment of the present specification provides a hetero-cyclic compound represented by the following Formula 1.

[Formula 1]

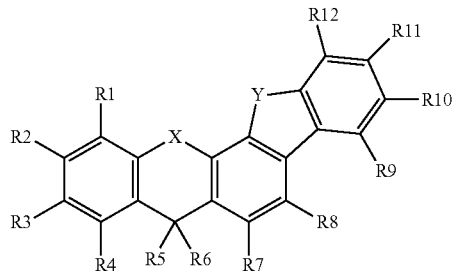

In Formula 1,

X and Y are each independently O or S,

R1 to R12 are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted aryl group; a substituted or unsubstituted fluorenyl group; a substituted or unsubstituted carbazole group; or a substituted or unsubstituted hetero-cyclic group including one or more of N, O and S atoms, provided that at least one of R1 to R4 is each independently represented by -(L)n-A, n is an integer of 0 to 4, L includes a substituted or unsubstituted arylene group; and one or more selected from the group consisting of a substituted or unsubstituted divalent hetero-cyclic group including one or more of N, O and S atoms, and when n is 2 to 4, a plurality of L's may be the same as or different from each other, and A is a substituted or unsubstituted monocyclic hetero-cyclic group including one or more of N; or a substituted or unsubstituted triphenylene group.

Further, an exemplary embodiment of the present specification provides an organic light emitting device including: a first electrode; a second electrode provided to face the first electrode; and one or more organic material layers including a light emitting layer provided between the first electrode and the second electrode, in which one or more of the organic material layers include the hetero-cyclic compound.

Advantageous Effects

A new compound according to the present specification may be used as a material for an organic material layer of an organic light emitting device, and it is possible to improve efficiency, achieve low driving voltage, and/or improve service life characteristics in the organic light emitting device by using the same.

DESCRIPTION OF DRAWINGS

FIG. 1 illustrates an example of an organic light emitting device composed of a substrate 101, an anode 201, a light emitting layer 301, and a cathode 401.

FIG. 2 illustrates an example of an organic light emitting device composed of a substrate 101, an anode 201, a hole injection layer 501, a hole transporting layer 601, a light emitting layer 301, an electron transporting layer 701, an electron injection layer 801, and a cathode 401.

MODE FOR INVENTION

Hereinafter, the present specification will be described in more detail.

An exemplary embodiment of the present specification provides a compound represented by Formula 1.

Examples of the substituents will be described below, but are not limited thereto.

The term "substituted or unsubstituted" in the present specification means that a group is substituted with one or two or more substituents selected from the group consisting of hydrogen; a halogen group; a nitrile group; a nitro group; a hydroxy group; an alkyl group; a cycloalkyl group; an alkenyl group; an amine group; an alkylamine group; an aralkylamine group; an arylamine group; a heteroarylamine group; an aryl group; a fluorenyl group; a carbazole group; and a hetero-cyclic group including one or more of N, O and S atoms, or is substituted with a substituent to which two or more substituents are linked among the substituents exemplified above, or has no substituent. For example, "the substituent to which two or more substituents are linked" may be a biphenyl group. That is, the biphenyl group may also be an aryl group, and may be interpreted as a substituent to which two phenyl groups are linked.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, examples of the halogen group include fluorine, chlorine, bromine or iodine.

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but is preferably a cycloalkyl group having 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the aryl group may be a monocyclic aryl group or a polycyclic aryl group, and includes the case where an alkyl group having 1 to 25 carbon atoms or an alkoxy group having 1 to 25 carbon atoms is substituted. Further, the aryl group in the present specification may mean an aromatic ring.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, a stilbenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthrenyl group, a triphenylene group, a pyrenyl group, a perylenyl group, a chrysenyl group, a fluoranthene group, a fluorenyl group, and the like, but are not limited thereto.

In the present specification, the fluorenyl group may be substituted, and two substituents may combine with each other to form a spiro structure.

When the fluorenyl group is substituted, the fluorenyl group may be

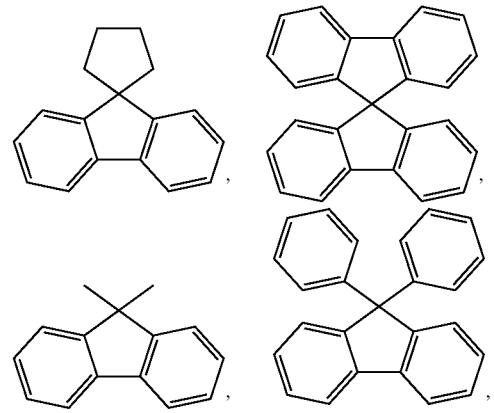

and the like. However, the fluorenyl group is not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, the hetero-cyclic group is a hetero-cyclic group including one or more of O, N, and S as a hetero element, and the number of carbon atoms thereof is not particularly limited, but is preferably 2 to 60. Examples of the hetero-cyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aryloxy group, the arylamine group, the aralkylamine group, the heteroarylamine group, the arylthioxy group, the arylsulfoxy group, and the arylalkenyl group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but are not limited thereto.

In the present specification, the alkyl group in the alkylthioxy group, the aralkylamine group, and the alkylsulfoxy group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In the present specification, the arylene group means that there are two bonding positions in an aryl group, that is, a divalent group. The above-described description on the aryl group may be applied, except that these are each a divalent group.

In the present specification, "*" means a moiety bonded to another substituent.

According to an exemplary embodiment of the present specification, X may be O.

According to an exemplary embodiment of the present specification, R2 or R3 is represented by $-(L)_n-A$, n is 0 or 1, L is a substituted or unsubstituted phenylene group; a substituted or unsubstituted biphenylene group; a substituted or unsubstituted divalent naphthalene group; or a substituted or unsubstituted anthracenylene group, and A may be a substituted or unsubstituted hetero-cyclic group; or a substituted or unsubstituted aryl group.

According to an exemplary embodiment of the present specification, R5 and R6 may be a substituted or unsubstituted alkyl group having 1 to 10 carbon atoms.

According to an exemplary embodiment of the present specification, R5 and R6 may be a methyl group.

According to an exemplary embodiment of the present specification, R10 may be hydrogen; or a substituted or unsubstituted aryl group having 6 to 20 carbon atoms.

According to an exemplary embodiment of the present specification, R10 may be hydrogen; a substituted or unsubstituted phenyl group; a substituted or unsubstituted biphenyl group; or a substituted or unsubstituted naphthyl group.

According to an exemplary embodiment of the present specification, A may be a substituted or unsubstituted pyridine group; a substituted or unsubstituted pyrimidine group; a substituted or unsubstituted pyridazine group; a substituted or unsubstituted pyrazine group; a substituted or unsubstituted triazine group; a substituted or unsubstituted tetrazine group; a pentazine group; a substituted or unsubstituted carbazole group; a substituted or unsubstituted dibenzofuranyl group; a substituted or unsubstituted dibenzothiophene group; a substituted or unsubstituted phenyl group; a substituted or unsubstituted biphenyl group; a substituted or unsubstituted naphthyl group; a substituted or unsubstituted phenanthrenyl group; a substituted or unsubstituted anthracenyl group; a substituted or unsubstituted fluorenyl group; a substituted or unsubstituted spiro bifluorenyl group; a substituted or unsubstituted fluoranthene group; or a substituted or unsubstituted triphenylene group.

According to an exemplary embodiment of the present specification, A may be a substituted or unsubstituted triazine group; a substituted or unsubstituted pyrimidine group; a substituted or unsubstituted carbazole group; a substituted or unsubstituted dibenzofuranyl group; a substituted or unsubstituted dibenzothiophene group; a substituted or unsubstituted phenyl group; a substituted or unsubstituted biphenyl group; a substituted or unsubstituted naphthyl group; a substituted or unsubstituted phenanthrenyl group; a substituted or unsubstituted anthracenyl group; a substituted or unsubstituted fluorenyl group; a substituted or unsubstituted spiro bifluorenyl group; a substituted or unsubstituted fluoranthene group; or a substituted or unsubstituted triphenylene group.

According to an exemplary embodiment of the present specification, when A is additionally substituted, the additional substituent may be a substituent which is substituted with one or more substituents selected from the group consisting of a halogen group; an alkyl group having 1 to 10 carbon atoms; an aryl group having 6 to 20 carbon atoms; and a hetero-cyclic group including one or more of N, O and S as a heteroatom having 2 to 20 carbon atoms.

According to an exemplary embodiment of the present specification, when A is additionally substituted, A may be substituted with a phenyl group.

According to an exemplary embodiment of the present specification, R2 may be a substituted or unsubstituted triazine group.

According to an exemplary embodiment of the present specification, R2 may be a phenyl group in which a substituted or unsubstituted triazine group is substituted.

According to an exemplary embodiment of the present specification, R2 may be a substituted or unsubstituted pyrimidine group.

According to an exemplary embodiment of the present specification, R2 may be a phenyl group in which a substituted or unsubstituted pyrimidine group is substituted.

According to an exemplary embodiment of the present specification, R2 may be a substituted or unsubstituted carbazole group.

According to an exemplary embodiment of the present specification, R2 may be a phenyl group in which a substituted or unsubstituted carbazole group is substituted.

According to an exemplary embodiment of the present specification, R2 may be a substituted or unsubstituted dibenzofuranyl group.

According to an exemplary embodiment of the present specification, R2 may be a phenyl group in which a substituted or unsubstituted dibenzofuranyl group is substituted.

According to an exemplary embodiment of the present specification, R2 may be a substituted or unsubstituted dibenzothiophene group.

According to an exemplary embodiment of the present specification, R2 may be a phenyl group in which a substituted or unsubstituted dibenzothiophene group is substituted.

According to an exemplary embodiment of the present specification, R2 may be a substituted or unsubstituted phenyl group.

According to an exemplary embodiment of the present specification, R2 may be a substituted or unsubstituted naphthyl group.

According to an exemplary embodiment of the present specification, R2 may be a phenyl group in which a substituted or unsubstituted naphthyl group is substituted.

According to an exemplary embodiment of the present specification, R2 may be a naphthyl group in which a substituted or unsubstituted naphthyl group is substituted.

According to an exemplary embodiment of the present specification, R2 may be a substituted or unsubstituted phenanthrenyl group.

According to an exemplary embodiment of the present specification, R2 may be a phenyl group in which a substituted or unsubstituted phenanthrenyl group is substituted.

According to an exemplary embodiment of the present specification, R2 may be a substituted or unsubstituted anthracenyl group.

According to an exemplary embodiment of the present specification, R2 may be a phenyl group in which a substituted or unsubstituted anthracenyl group is substituted.

According to an exemplary embodiment of the present specification, R2 may be a substituted or unsubstituted fluorenyl group.

According to an exemplary embodiment of the present specification, R2 may be a phenyl group in which a substituted or unsubstituted fluorenyl group is substituted.

According to an exemplary embodiment of the present specification, R2 may be a substituted or unsubstituted spiro bifluorenyl group.

According to an exemplary embodiment of the present specification, R2 may be a phenyl group in which a substituted or unsubstituted spiro bifluorenyl group is substituted.

According to an exemplary embodiment of the present specification, R2 may be a substituted or unsubstituted fluoranthene group.

According to an exemplary embodiment of the present specification, R2 may be a phenyl group in which a substituted or unsubstituted fluoranthene group is substituted.

According to an exemplary embodiment of the present specification, R2 may be a substituted or unsubstituted triphenylene group.

According to an exemplary embodiment of the present specification, R2 may be a phenyl group in which a substituted or unsubstituted triphenylene group is substituted.

According to an exemplary embodiment of the present specification, R3 may be a substituted or unsubstituted triazine group.

According to an exemplary embodiment of the present specification, R3 may be a phenyl group in which a substituted or unsubstituted triazine group is substituted.

According to an exemplary embodiment of the present specification, R3 may be a substituted or unsubstituted pyrimidine group.

According to an exemplary embodiment of the present specification, R3 may be a phenyl group in which a substituted or unsubstituted pyrimidine group is substituted.

According to an exemplary embodiment of the present specification, R3 may be a substituted or unsubstituted carbazole group.

According to an exemplary embodiment of the present specification, R3 may be a phenyl group in which a substituted or unsubstituted carbazole group is substituted.

According to an exemplary embodiment of the present specification, R3 may be a substituted or unsubstituted dibenzofuranyl group.

According to an exemplary embodiment of the present specification, R3 may be a phenyl group in which a substituted or unsubstituted dibenzofuranyl group is substituted.

According to an exemplary embodiment of the present specification, R3 may be a substituted or unsubstituted dibenzothiophene group.

According to an exemplary embodiment of the present specification, R3 may be a phenyl group in which a substituted or unsubstituted dibenzothiophene group is substituted.

According to an exemplary embodiment of the present specification, R3 may be a substituted or unsubstituted phenyl group.

According to an exemplary embodiment of the present specification, R3 may be a substituted or unsubstituted naphthyl group.

According to an exemplary embodiment of the present specification, R3 may be a phenyl group in which a substituted or unsubstituted naphthyl group is substituted.

According to an exemplary embodiment of the present specification, R3 may be a naphthyl group in which a substituted or unsubstituted naphthyl group is substituted.

According to an exemplary embodiment of the present specification, R3 may be a substituted or unsubstituted phenanthrenyl group.

According to an exemplary embodiment of the present specification, R3 may be a phenyl group in which a substituted or unsubstituted phenanthrenyl group is substituted.

According to an exemplary embodiment of the present specification, R3 may be a substituted or unsubstituted anthracenyl group.

According to an exemplary embodiment of the present specification, R3 may be a phenyl group in which a substituted or unsubstituted anthracenyl group is substituted.

According to an exemplary embodiment of the present specification, R3 may be a substituted or unsubstituted fluorenyl group.

According to an exemplary embodiment of the present specification, R3 may be a phenyl group in which a substituted or unsubstituted fluorenyl group is substituted.

According to an exemplary embodiment of the present specification, R3 may be a substituted or unsubstituted spiro bifluorenyl group.

According to an exemplary embodiment of the present specification, R3 may be a phenyl group in which a substituted or unsubstituted spiro bifluorenyl group is substituted.

According to an exemplary embodiment of the present specification, R3 may be a substituted or unsubstituted fluoranthene group.

According to an exemplary embodiment of the present specification, R3 may be a phenyl group in which a substituted or unsubstituted fluoranthene group is substituted.

According to an exemplary embodiment of the present specification, R3 may be a substituted or unsubstituted tripheneylene group.

According to an exemplary embodiment of the present specification, R3 may be a phenyl group in which a substituted or unsubstituted triphenylene group is substituted.

According to an exemplary embodiment of the present specification, the compound represented by Formula 1 may be represented by the following Formula 1-1 or 1-2.

[Formula 1-1]

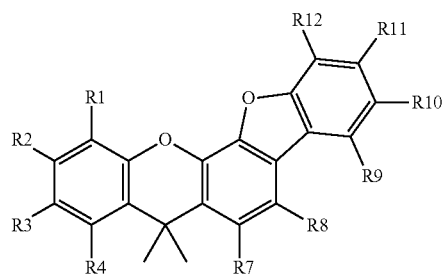

[Formula 1-2]

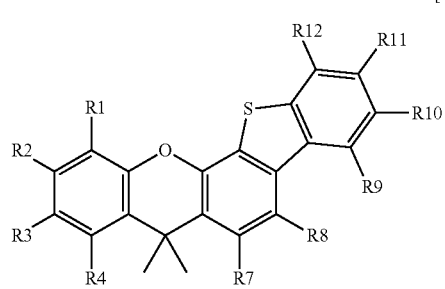

R1 to R4 and R7 to R12 in Formulae 1-1 and 1-2 are the same as those defined in Formula 1.

According to an exemplary embodiment of the present specification, -(L)n-A may be any one substituent of the following Substituents 1-1 to 1-41, which are substituted or unsubstituted. However, -(L)n-A is not limited thereto.

According to an exemplary embodiment of the present specification, when the following Substituents 1-1 to 1-41 are additionally substituted, the additional substituent may be a substituent which is substituted with one or more substituents selected from the group consisting of a halogen group; an alkyl group having 1 to 10 carbon atoms; an aryl group having 6 to 20 carbon atoms; and a hetero-cyclic group including one or more of N, O and S as a heteroatom and having 2 to 20 carbon atoms.

Substituent 1-1

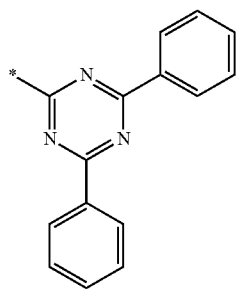

Substituent 1-2

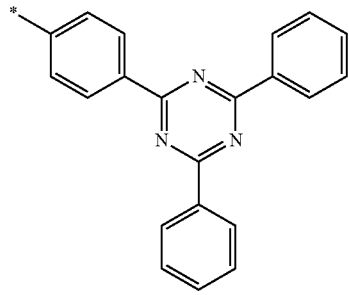

Substituent 1-3

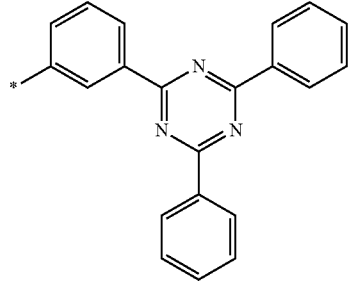

Substituent 1-4

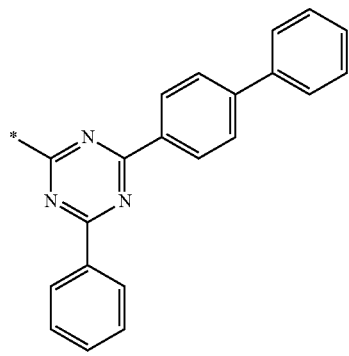

Substituent 1-5

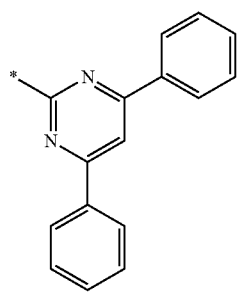

Substituent 1-6

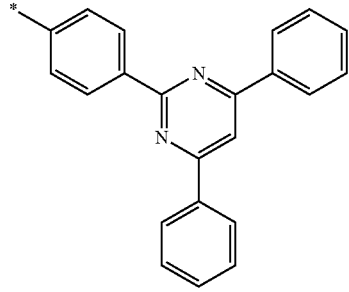

Substituent 1-7
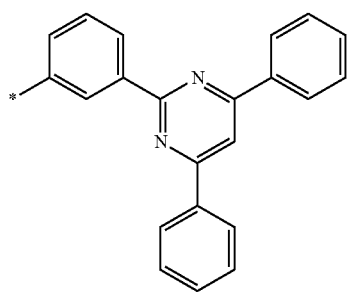
Substituent 1-8
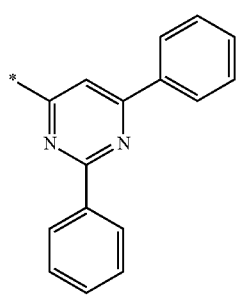
Substituent 1-9
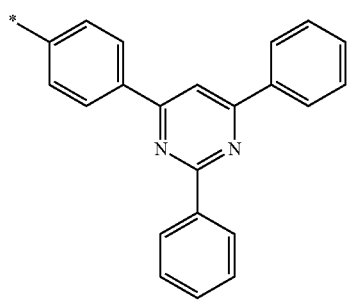
Substituent 1-10
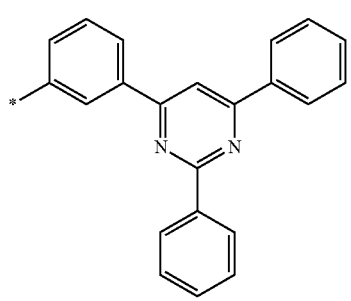
Substituent 1-11
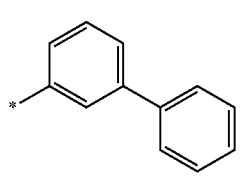
Substituent 1-12
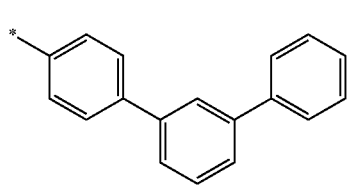
Substituent 1-13
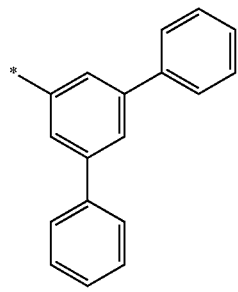
Substituent 1-14
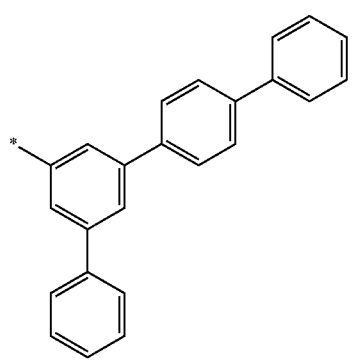
Substituent 1-15
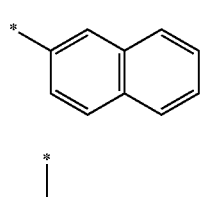
Substituent 1-16
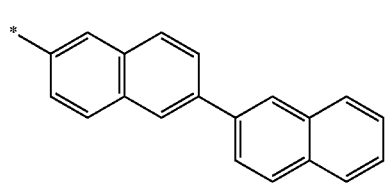
Substituent 1-17
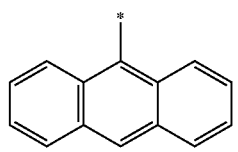
Substituent 1-18
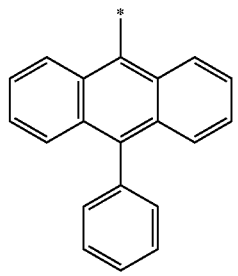
Substituent 1-19

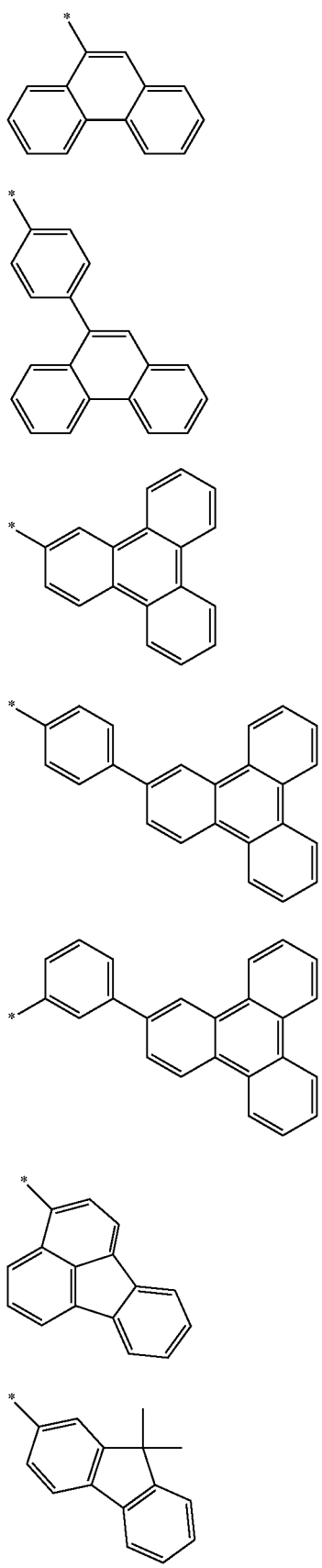
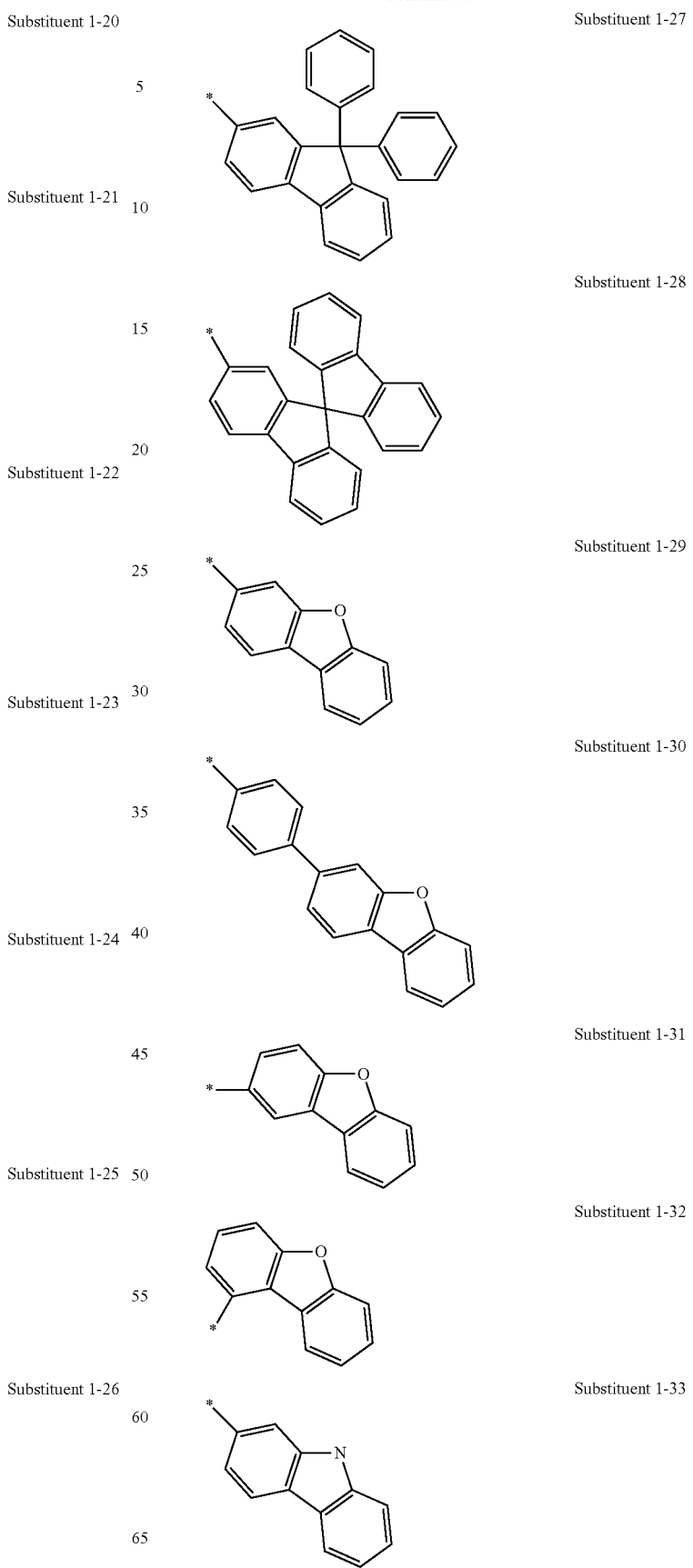

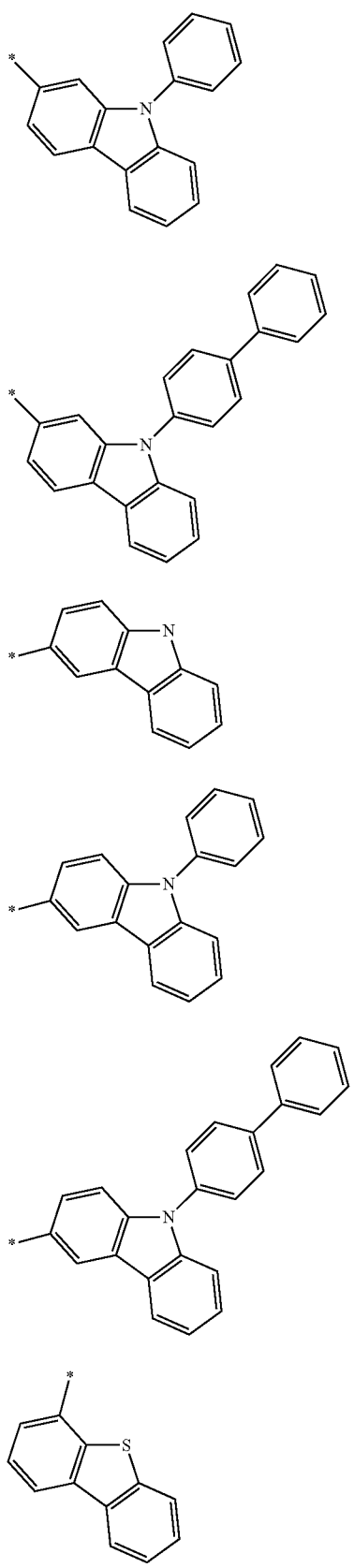
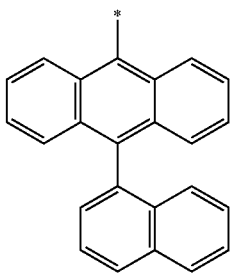
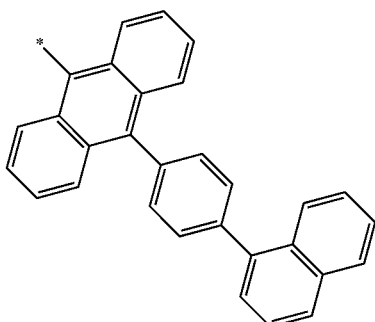
According to an exemplary embodiment of the present specification, the compound represented by Formula 1 may be a compound represented by any one of the following Formulae 2-1 to 2-81. However, the compound is not limited thereto.
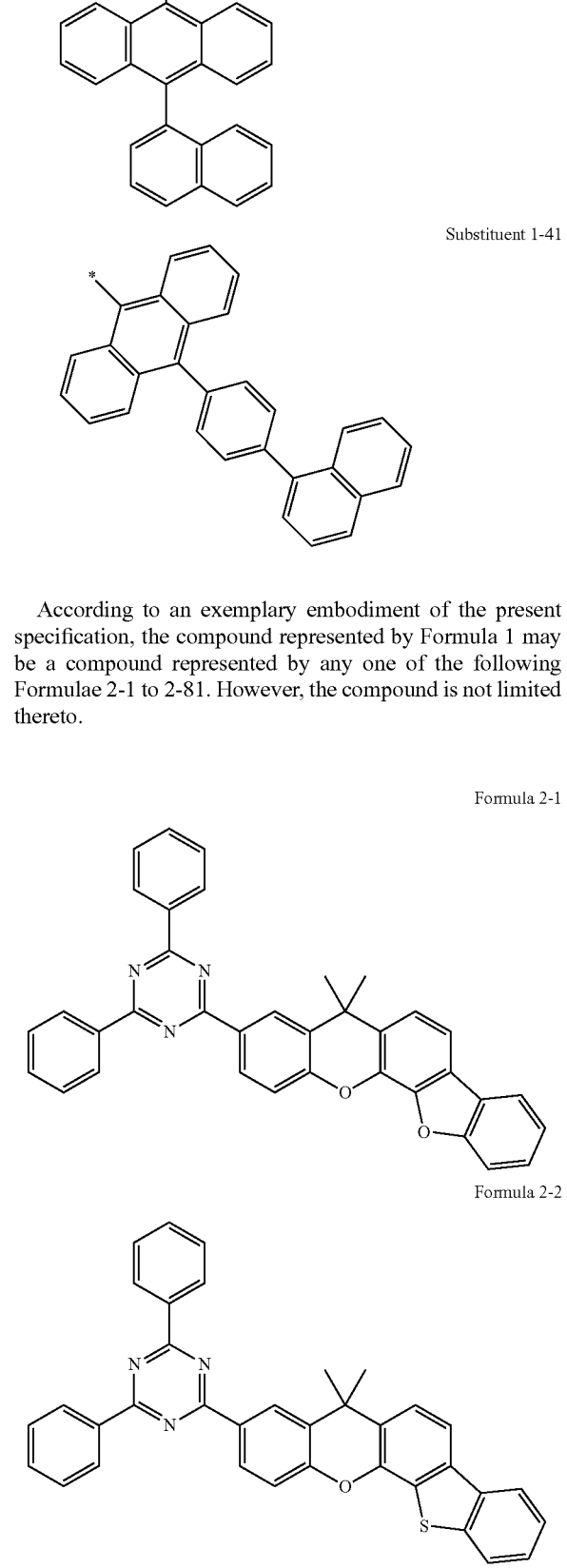

Formula 2-3
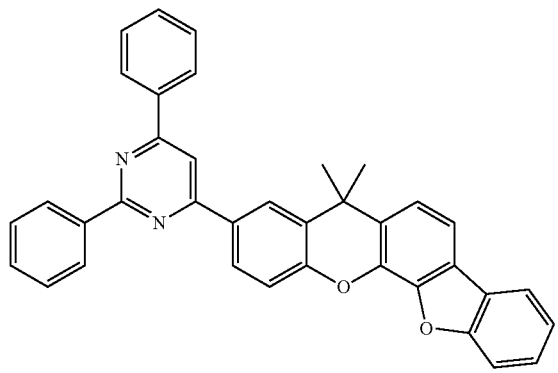
Formula 2-4
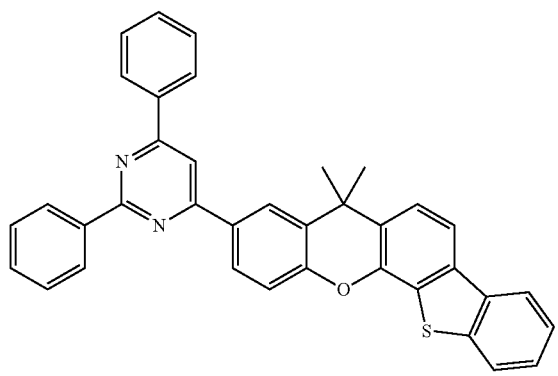
Formula 2-5
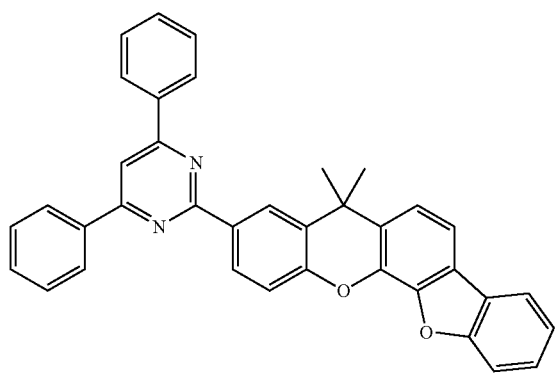
Formula 2-6
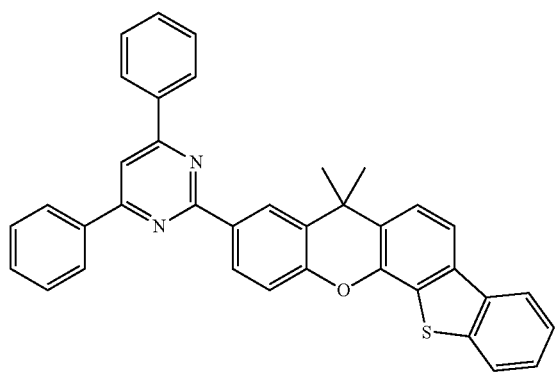
Formula 2-7
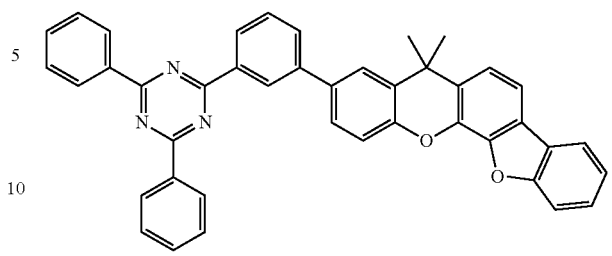
Formula 2-8
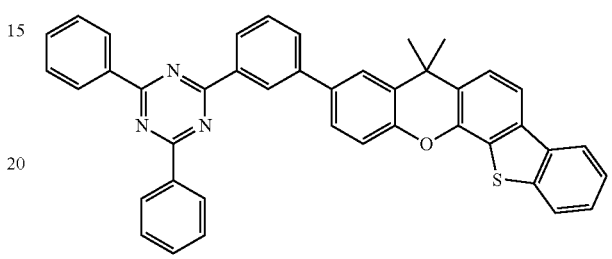
Formula 2-9
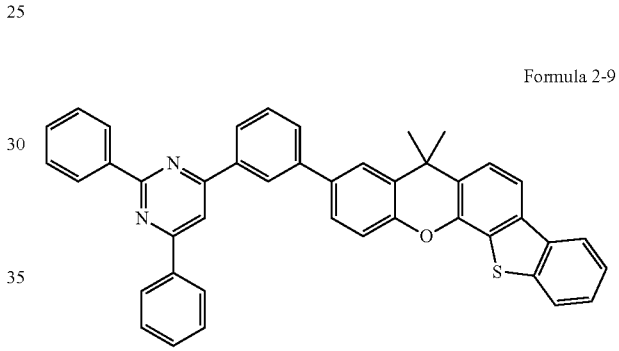
Formula 2-10
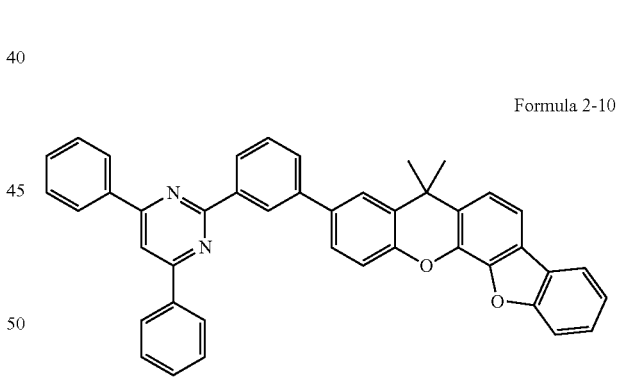
Formula 2-11
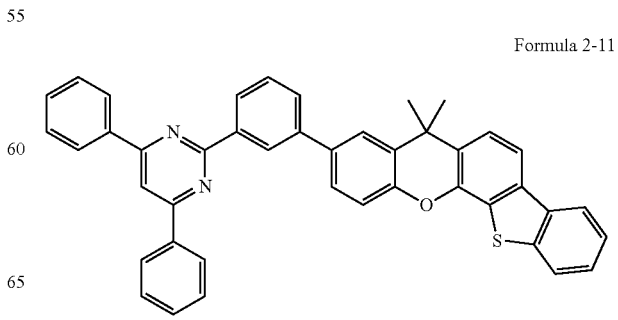

Formula 2-12
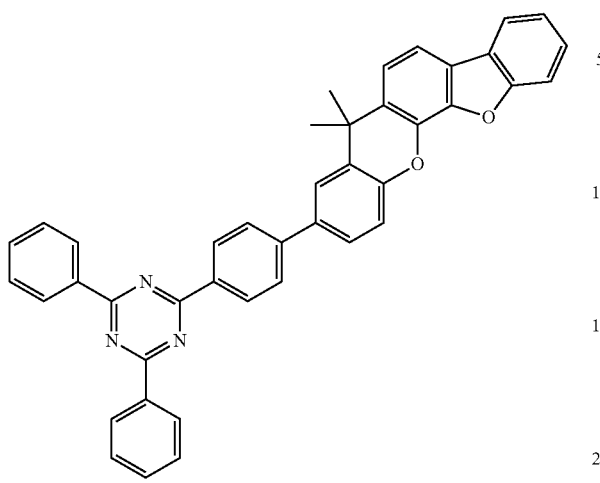
Formula 2-15
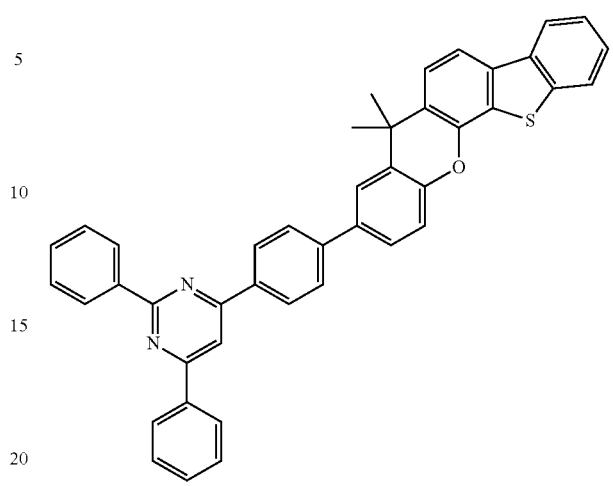
Formula 2-13
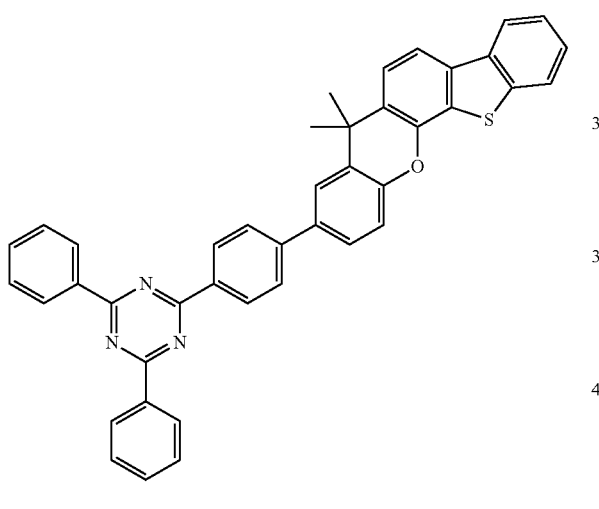
Formula 2-16
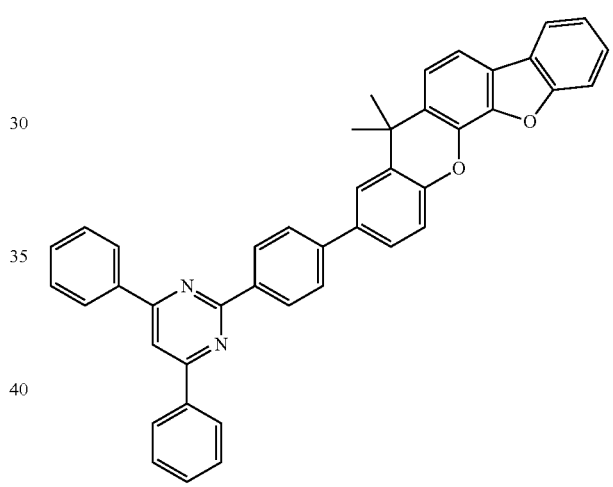
Formula 2-14
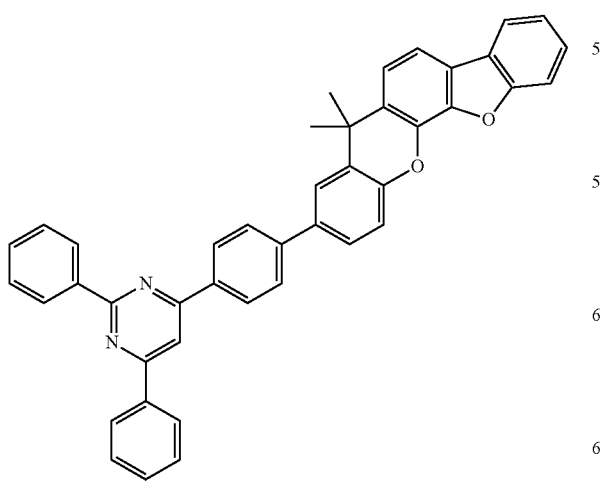
Formula 2-17
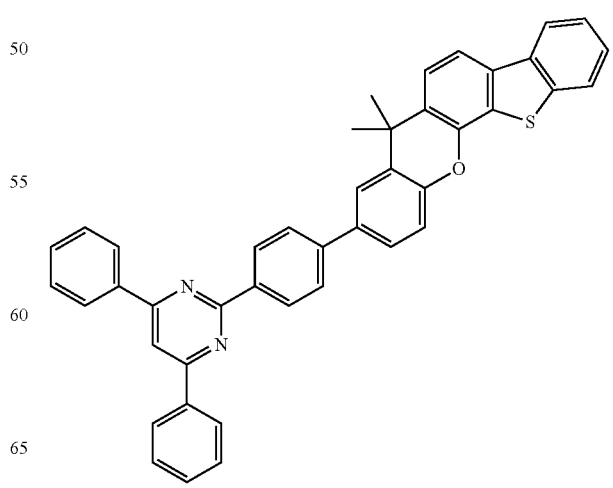

Formula 2-18
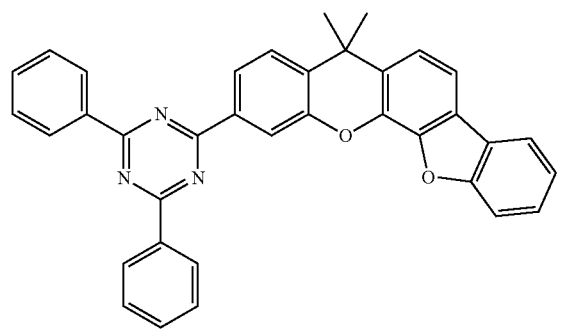
Formula 2-19
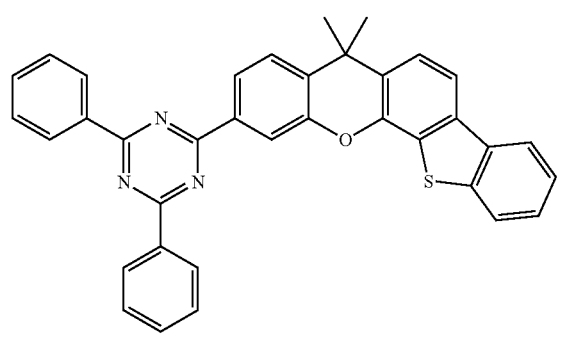
Formula 2-20
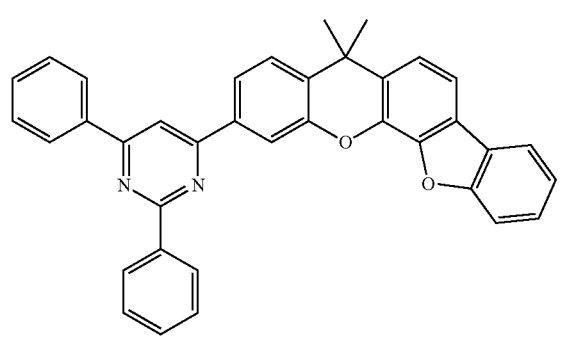
Formula 2-21
Formula 2-22
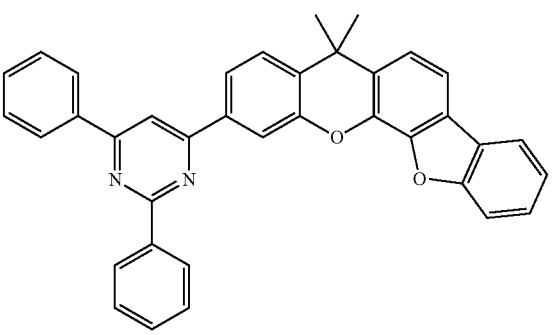
Formula 2-23
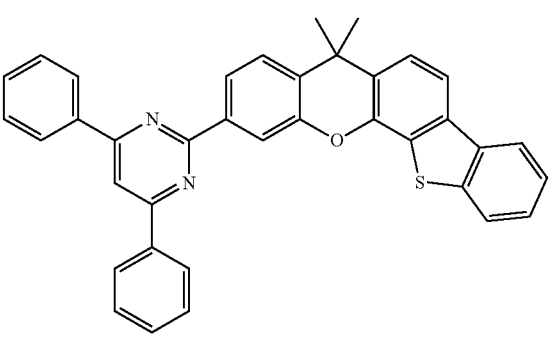
Formula 2-24
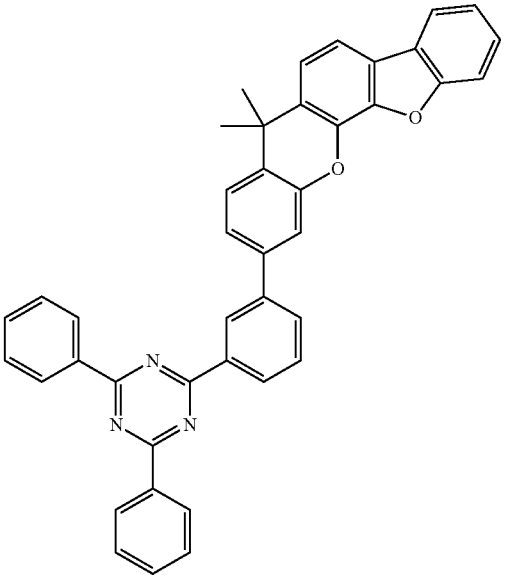

Formula 2-25
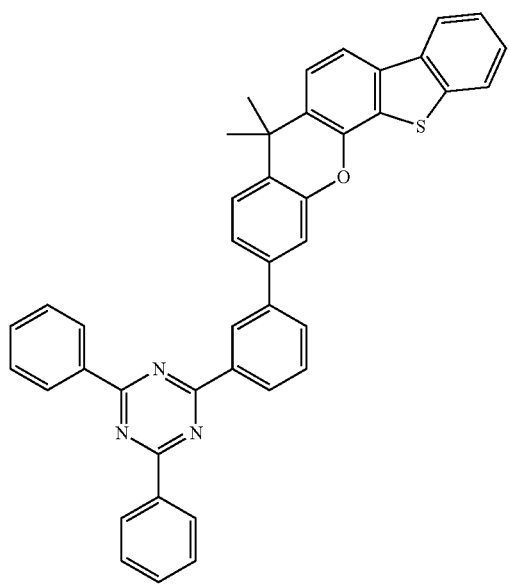
Formula 2-27
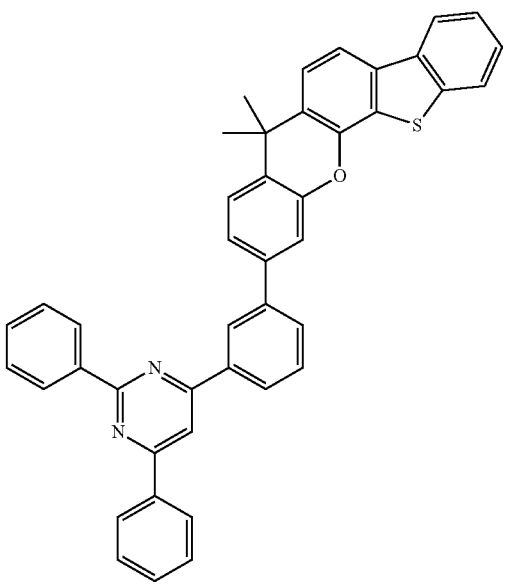
Formula 2-26
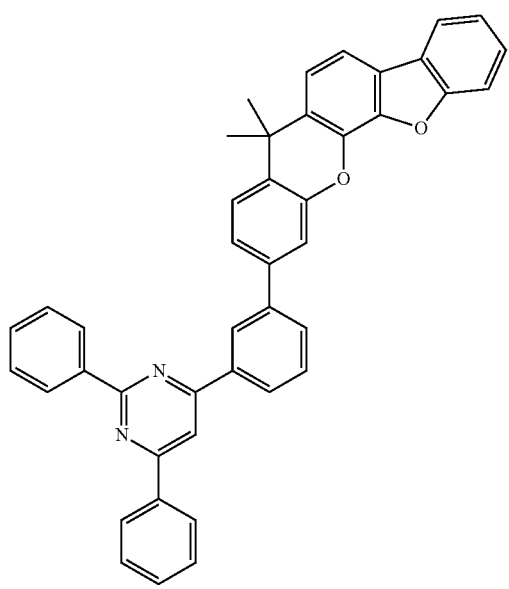
Formula 2-28
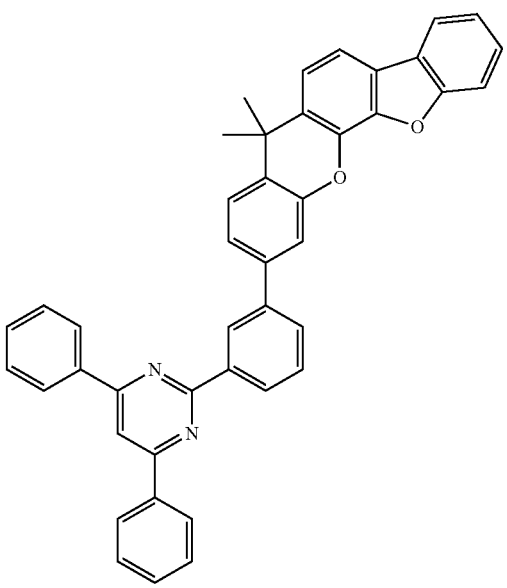

Formula 2-29
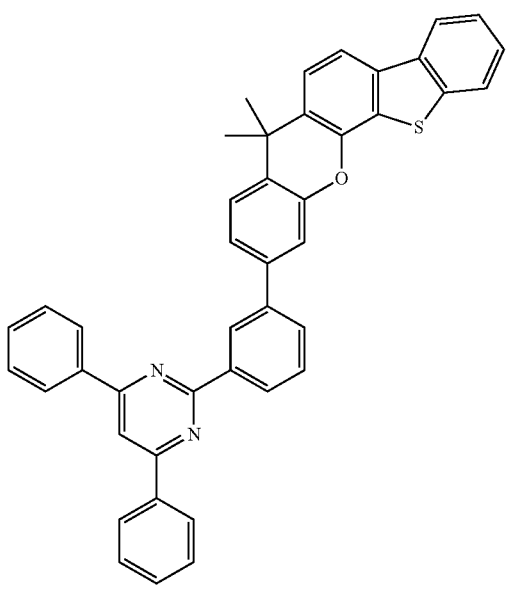
Formula 2-30
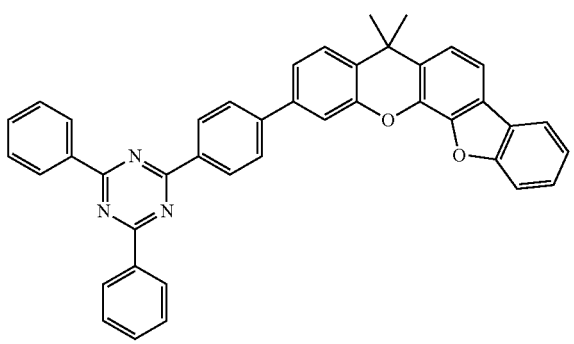
Formula 2-31
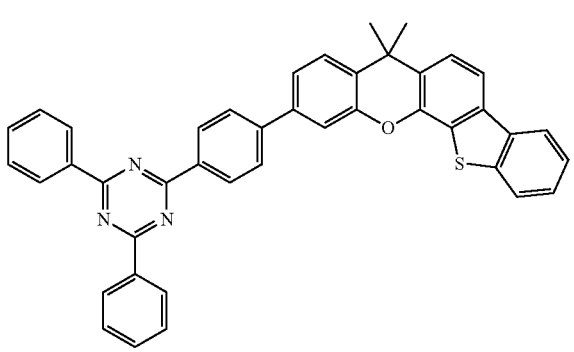
Formula 2-32
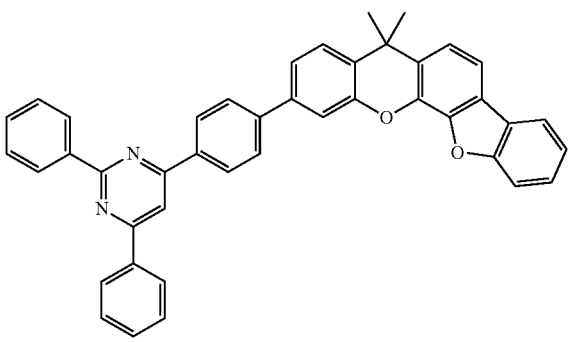
Formula 2-33
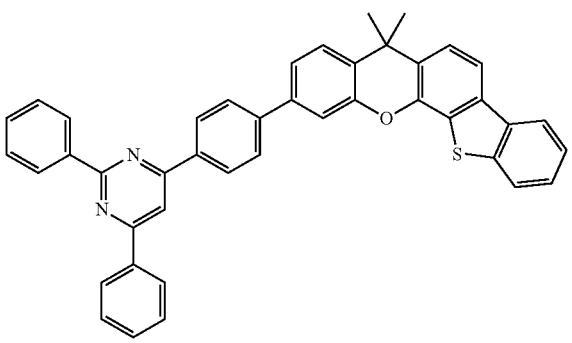
Formula 2-34
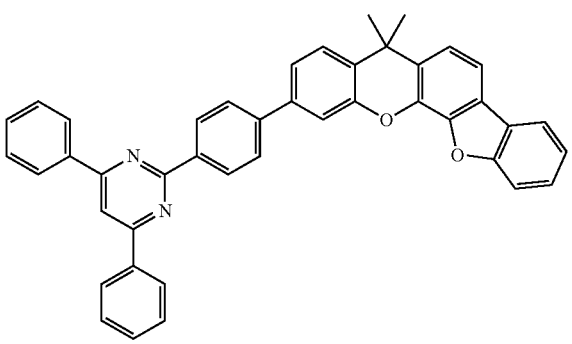
Formula 2-35
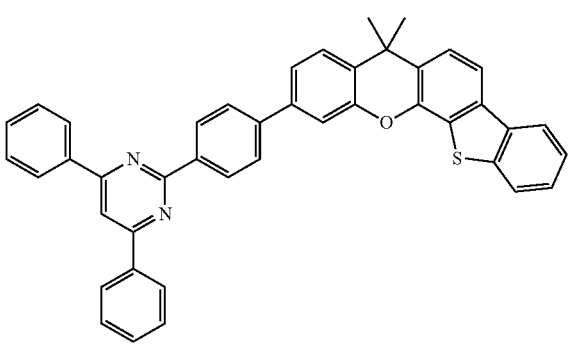

Formula 2-36
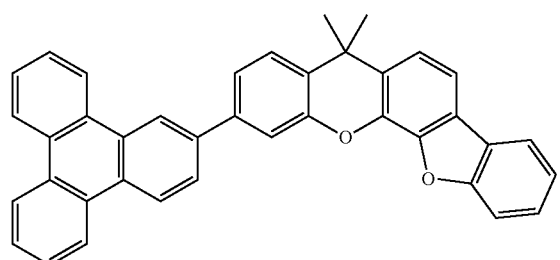
Formula 2-37
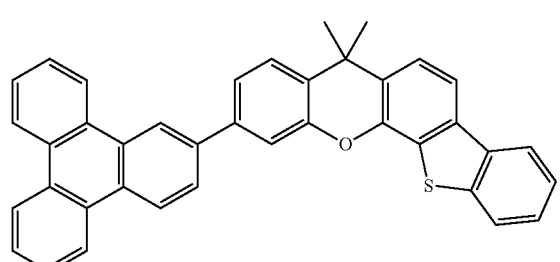
Formula 2-38
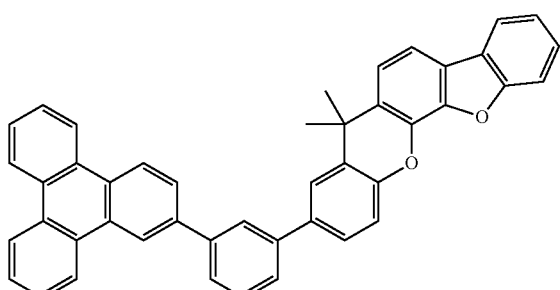
Formula 2-39
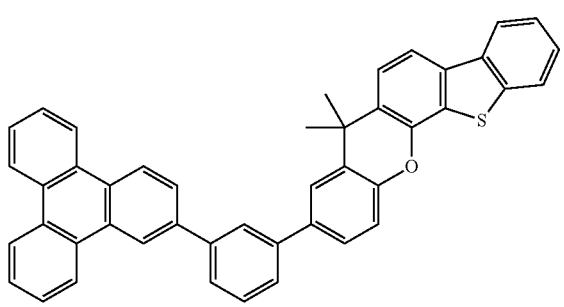
Formula 2-40
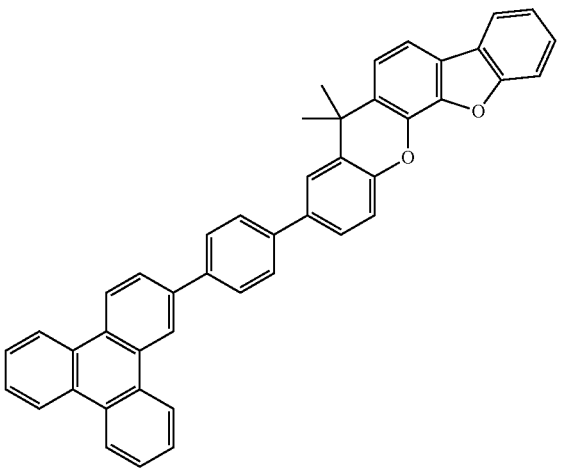
Formula 2-41
Formula 2-42
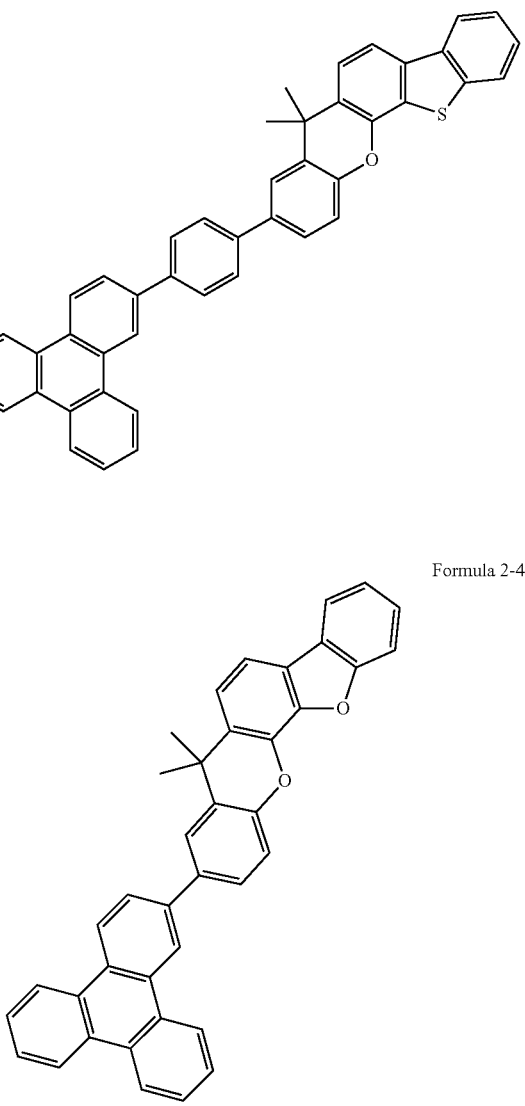

Formula 2-43
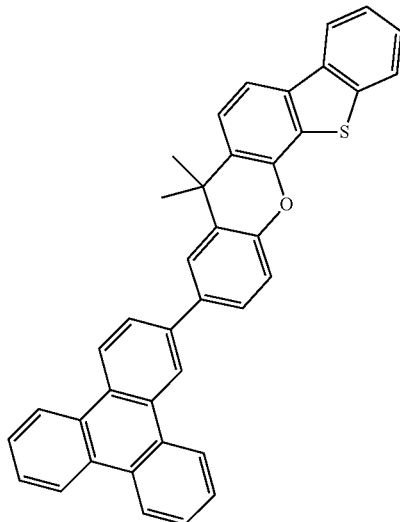
Formula 2-44
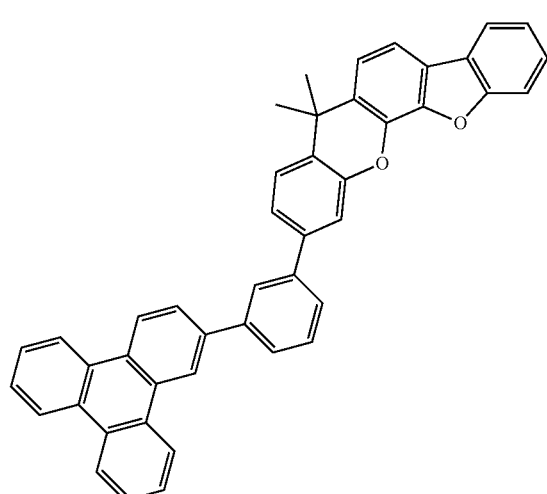
Formula 2-45
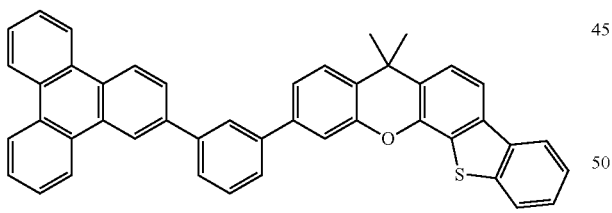
Formula 2-46
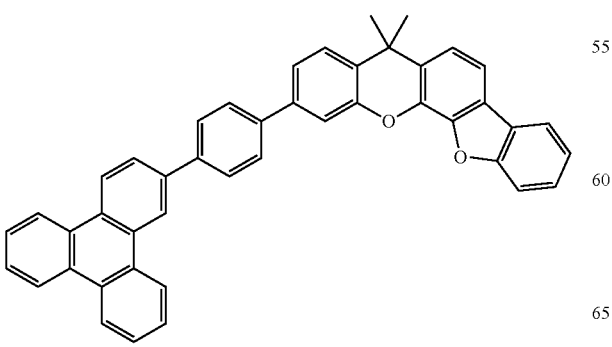
Formula 2-47
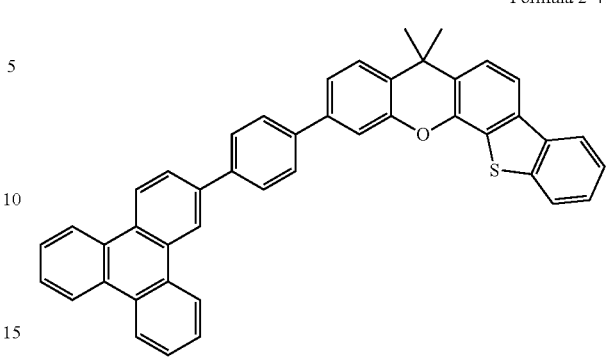
Formula 2-48
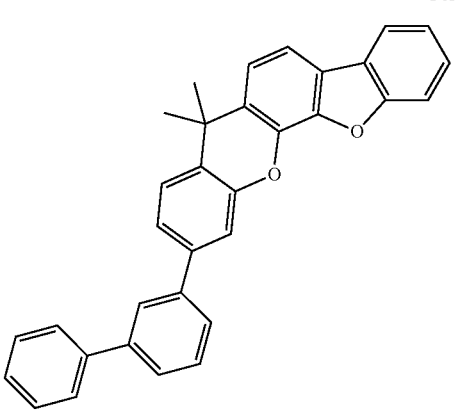
Formula 2-49
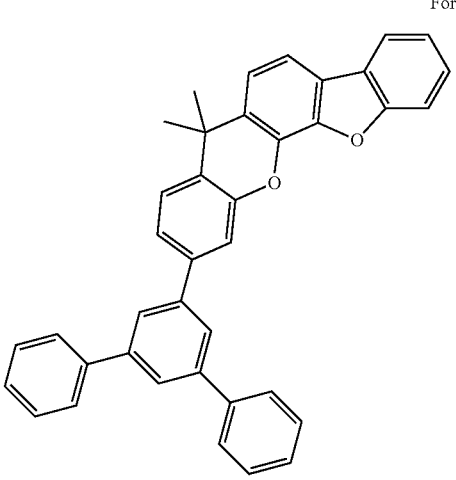

Formula 2-50
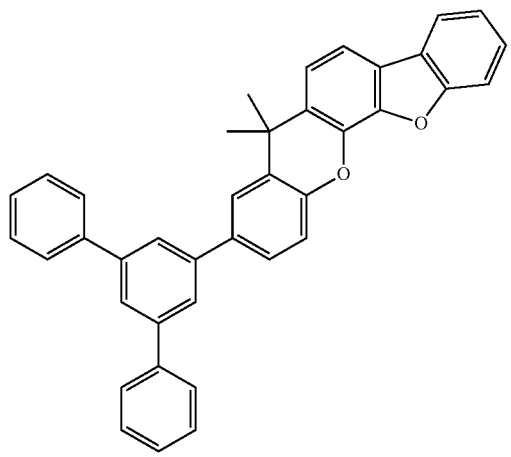
Formula 2-53
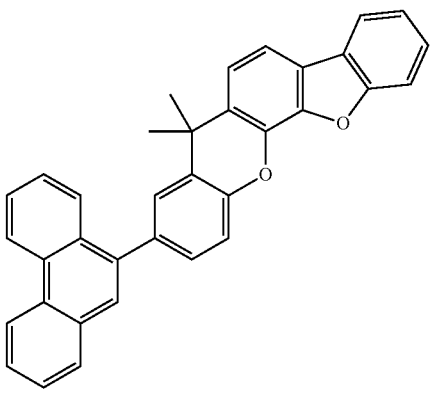
Formula 2-51
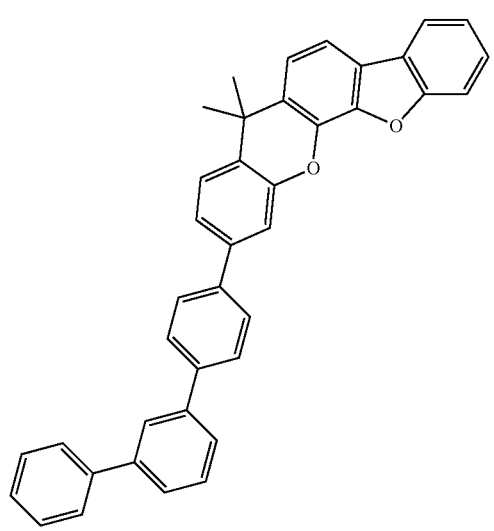
Formula 2-54
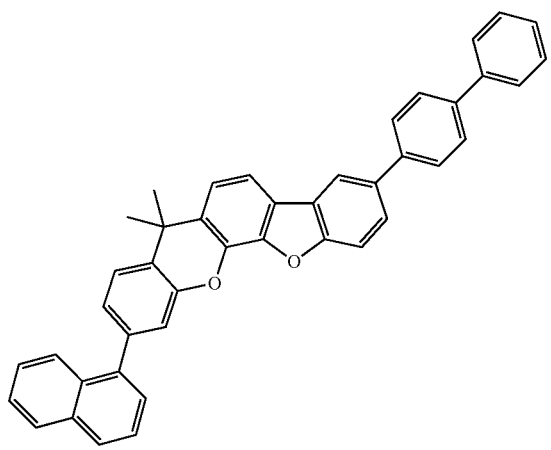
Formula 2-52
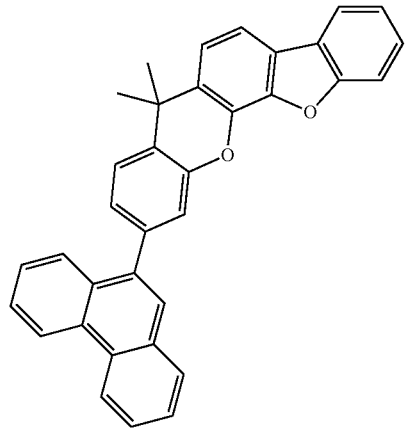
Formula 2-55
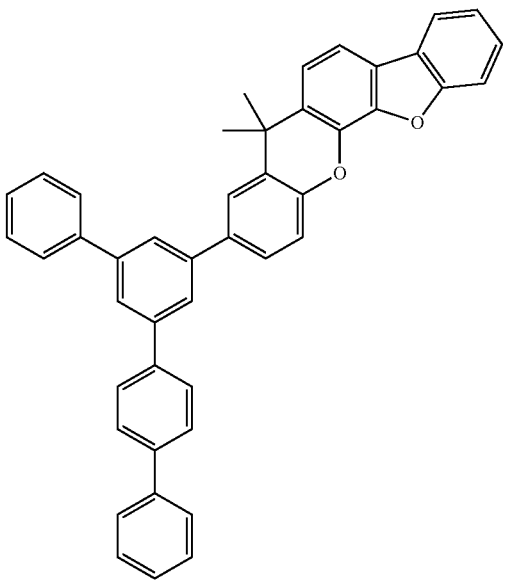

Formula 2-56
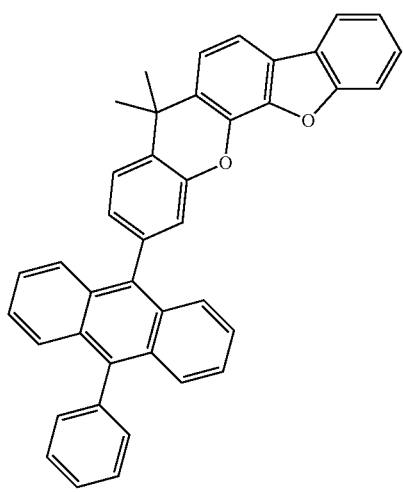
Formula 2-57
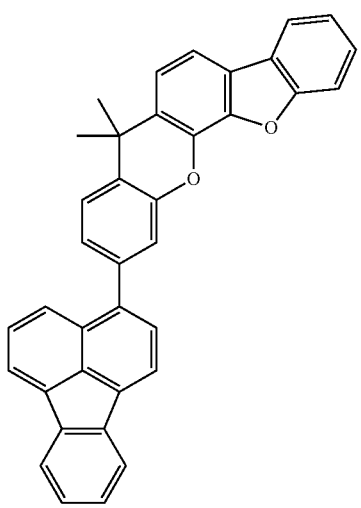
Formula 2-58
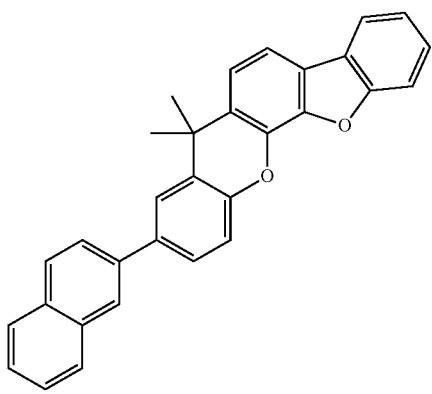
Formula 2-59
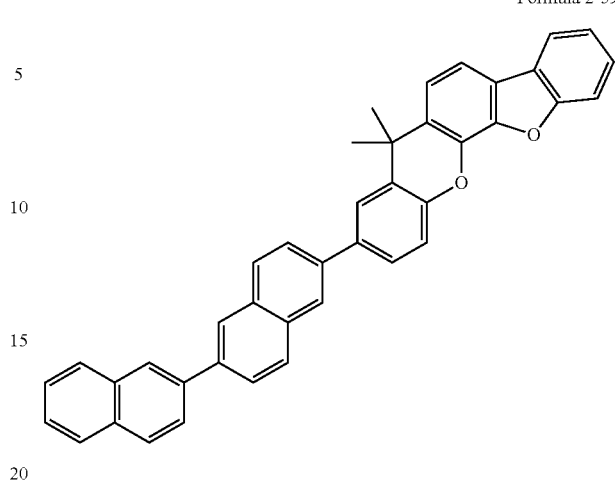
Formula 2-60
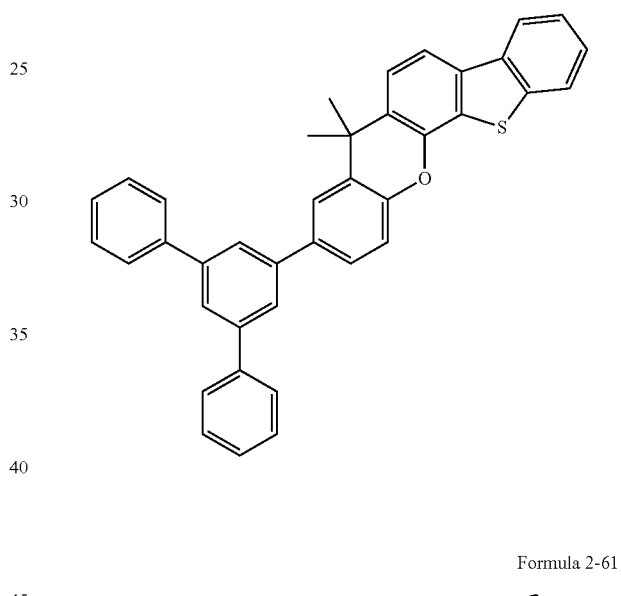
Formula 2-61
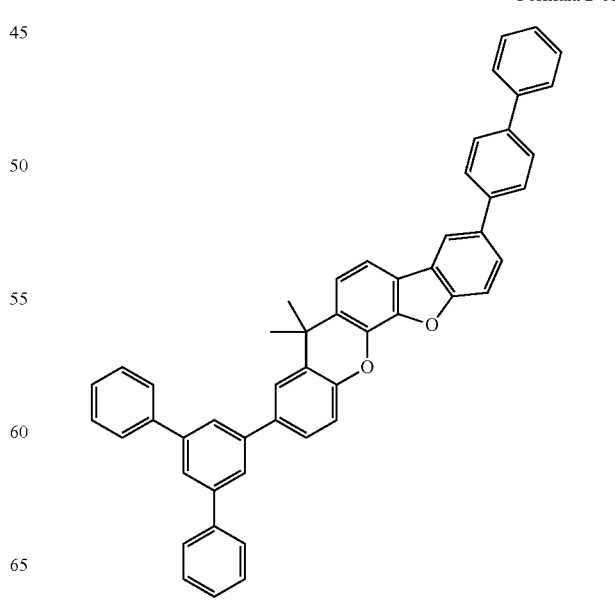

Formula 2-62
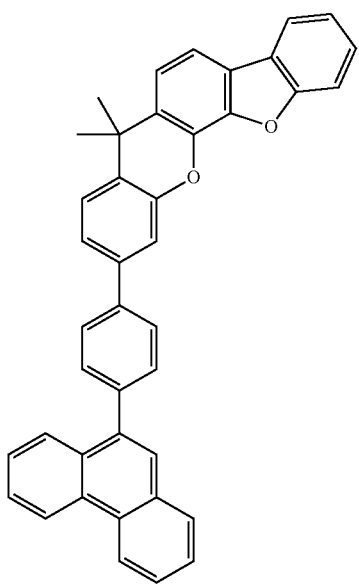
Formula 2-63
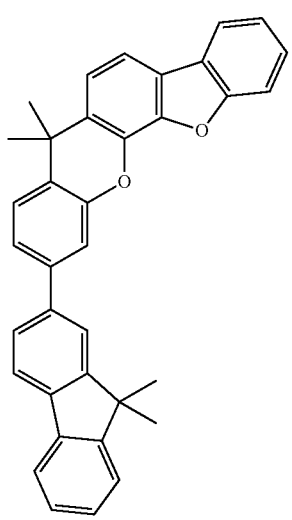
Formula 2-64
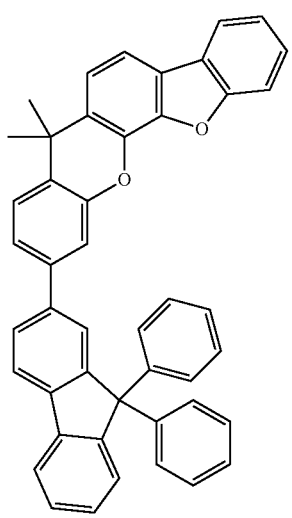
Formula 2-65
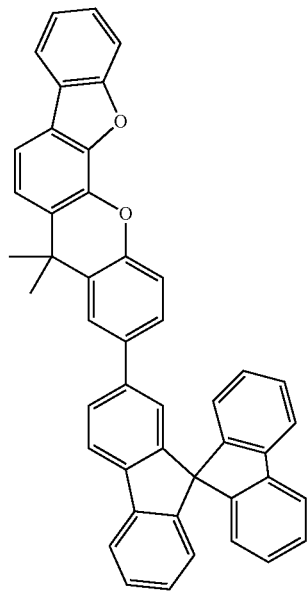
Formula 2-66
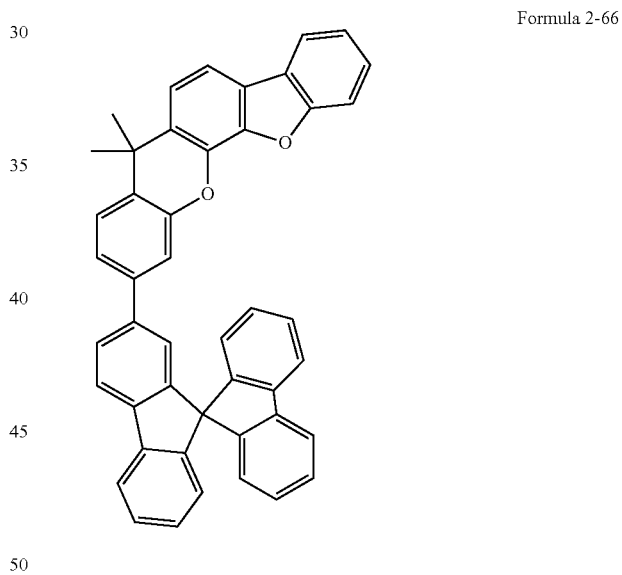
Formula 2-67
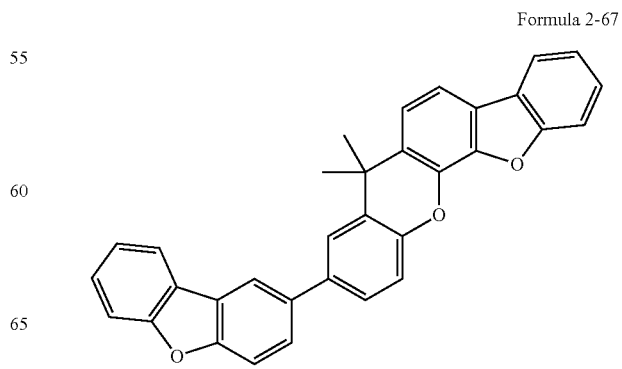

Formula 2-68
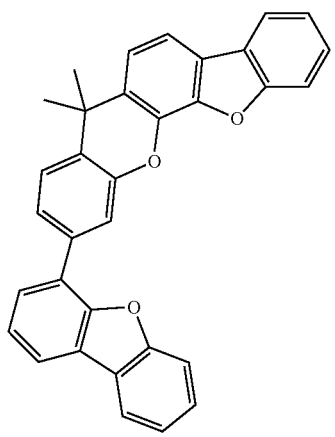
Formula 2-69
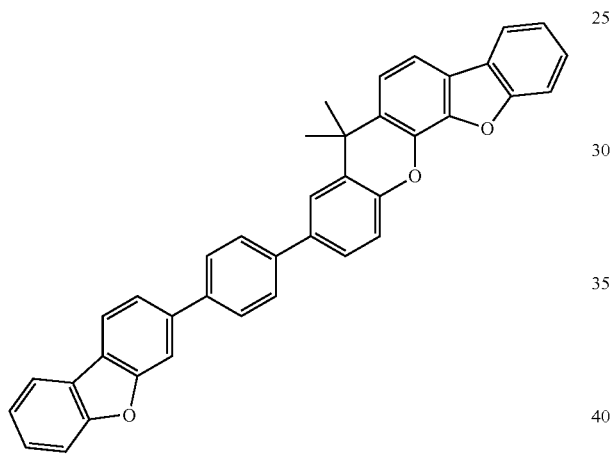
Formula 2-70
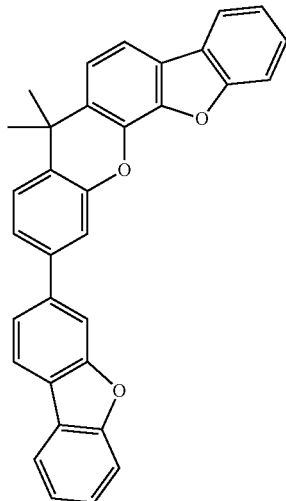
Formula 2-71
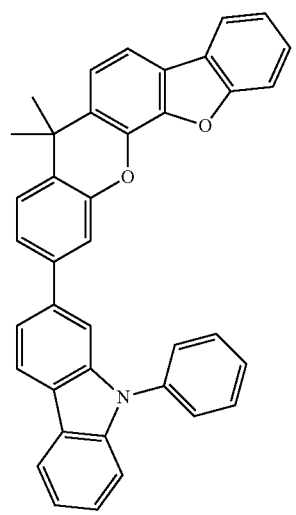
Formula 2-72
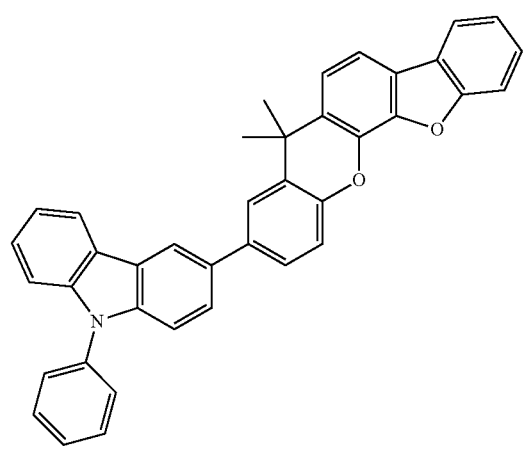
Formula 2-73
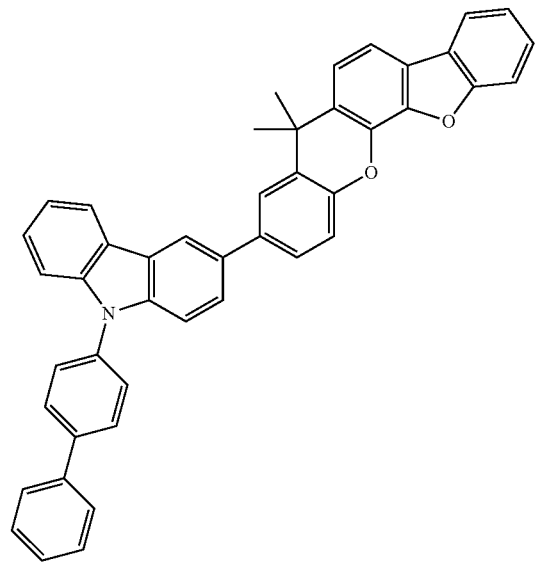

Formula 2-74
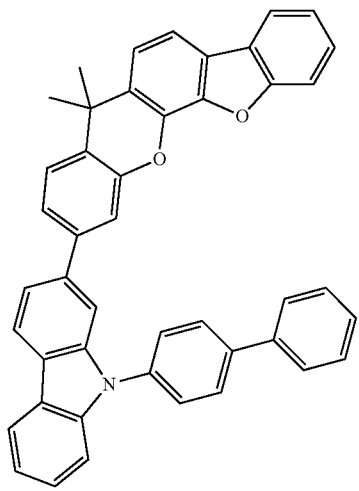
Formula 2-75
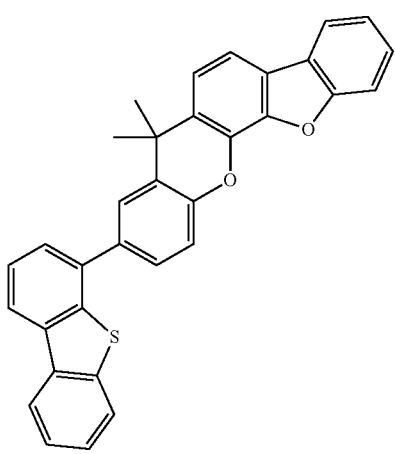
Formula 2-76
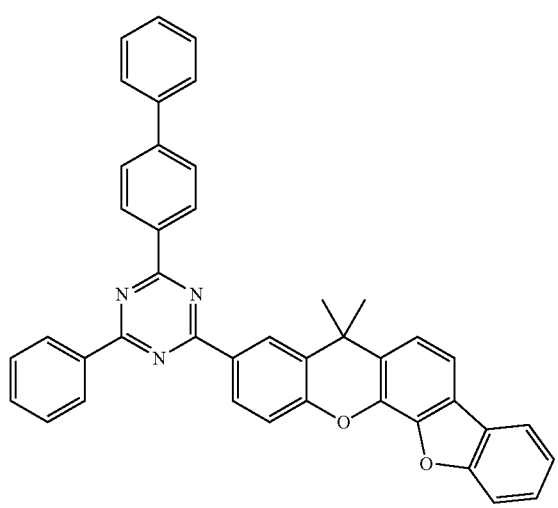
Formula 2-77
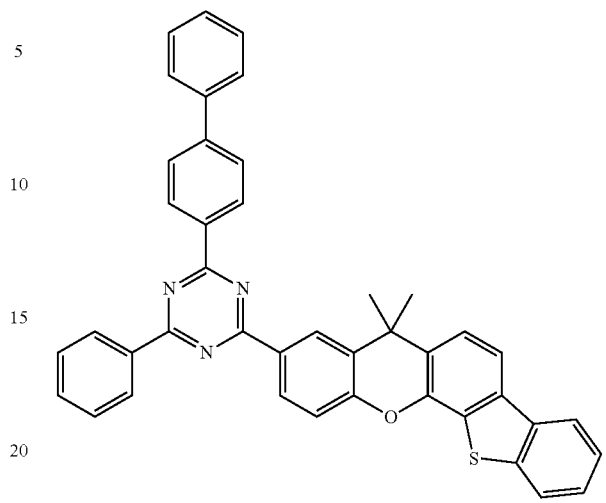
Formula 2-78
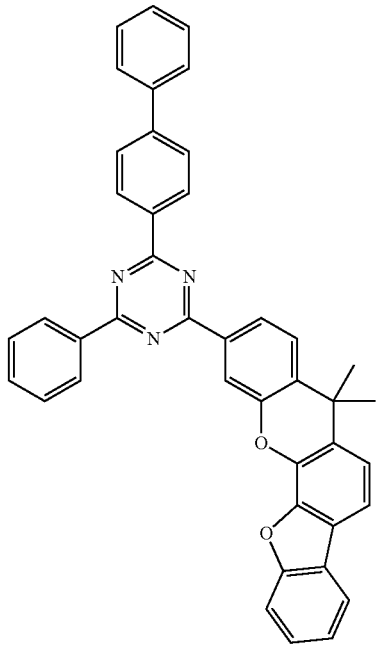
Formula 2-79
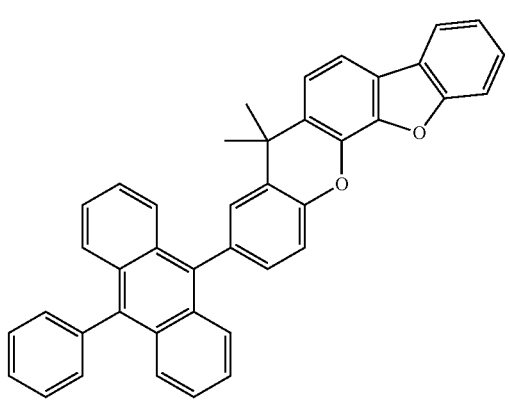

Formula 2-80

Formula 2-81

According to an exemplary embodiment of the present specification, a general synthesis example of the compound represented by Formula 1 may be as follows.

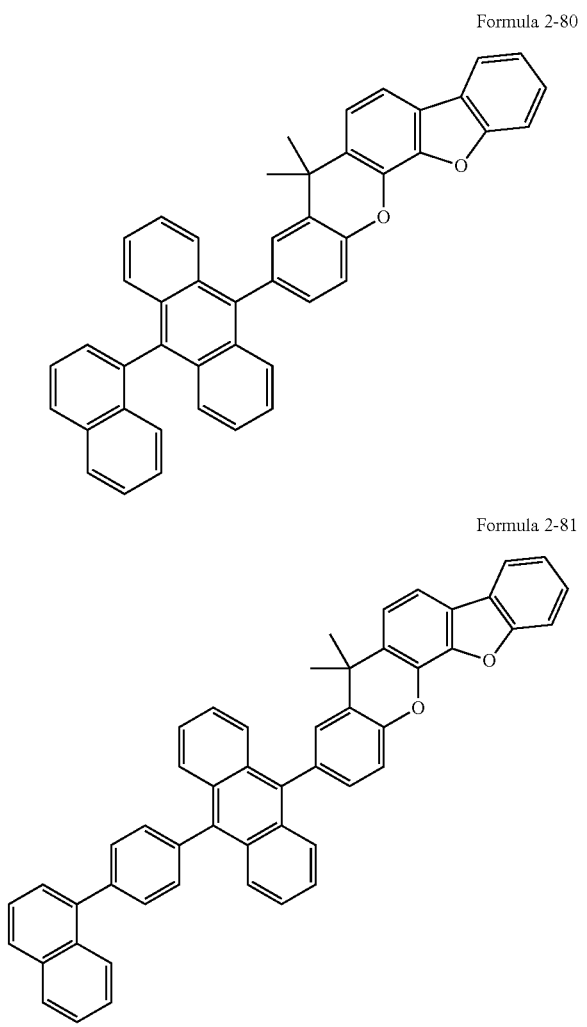

Specifically, according to an exemplary embodiment of the present specification, in the general synthesis example, the compound represented by K may be produced through a ring closing reaction by using the compound represented by Q and a benzoate-based compound, and furthermore, the compound represented by L may be prepared by using a halide. The compound represented by Formula 1 may be prepared by using the synthesis example, and adjusting various substituents or substitution positions, if necessary.

An exemplary embodiment of the present specification provides an organic light emitting device including the hetero-cyclic compound.

An exemplary embodiment of the present specification provides an organic light emitting device including: a first electrode; a second electrode provided to face the first electrode; and one or more organic material layers including a light emitting layer provided between the first electrode and the second electrode, in which one or more layers of the organic material layers include the hetero-cyclic compound.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer may include a hole transporting layer, a hole injection layer, or a layer which simultaneously injects and transports holes, and the hole transporting layer, the hole injection layer, or the layer which simultaneously injects and transports holes may include the hetero-cyclic compound.

In another exemplary embodiment, the light emitting layer may include the hetero-cyclic compound. Specifically, according to an exemplary embodiment of the present specification, the hetero-cyclic compound may be a light emitting host.

In an exemplary embodiment of the present specification, the organic material layer may include an electron transporting layer, an electron injection layer, or a layer which simultaneously transports and injects electrons, and the electron transporting layer, the electron injection layer, or the layer which simultaneously transports and injects electrons may include the hetero-cyclic compound.

In an exemplary embodiment of the present specification, the electron transporting layer, the electron injection layer, or the layer which simultaneously transports and injects electrons may include only the hetero-cyclic compound.

In an exemplary embodiment of the present specification, the organic material layer may further include a hole injection layer or a hole transporting layer, which includes a compound including an arylamino group, a carbazole group, or a benzocarbazole group, in addition to the organic material layer including the hetero-cyclic compound.

In an exemplary embodiment of the present specification, the organic material layer including the hetero-cyclic compound may include the hetero-cyclic compound as a host, and may include other organic compounds, a metal or a metal compound as a dopant.

In an exemplary embodiment of the present specification, the organic material layer may include an electron blocking layer, and the electron blocking layer may include the hetero-cyclic compound.

In an exemplary embodiment of the present specification, the organic material layer may further include one or two or more layers selected from the group consisting of a hole injection layer, a hole transporting layer, an electron blocking layer, a charge generation layer, a hole blocking layer, an electron transporting layer, and an electron injection layer.

In another exemplary embodiment, the organic light emitting device may be an organic light emitting device having a structure (normal type) in which an anode, one or more organic material layers, and a cathode are sequentially stacked on a substrate.

In still another exemplary embodiment, the organic light emitting device may be an organic light emitting device having a reverse direction structure (inverted type) in which a cathode, one or more organic material layers, and an anode are sequentially stacked on a substrate.

For example, the structure of the organic light emitting device according to an exemplary embodiment of the present specification is illustrated in FIGS. 1 and 2.

FIG. 1 illustrates an example of an organic light emitting device composed of a substrate 101, an anode 201, a light emitting layer 301, and a cathode 401. In the structure, the hetero-cyclic compound may be included in the light emitting layer 301.

FIG. 2 illustrates an example of an organic light emitting device composed of a substrate 101, an anode 201, a hole injection layer 501, a hole transporting layer 601, a light emitting layer 301, an electron transporting layer 701, an electron injection layer 801, and a cathode 401. In the structure, the hetero-cyclic compound may be included in one or more layers of the hole injection layer 501, the hole transporting layer 601, the light emitting layer 301, the electron transporting layer 701, and the electron injection layer 801.

The organic light emitting device of the present specification may be manufactured by the materials and methods known in the art, except that one or more layers of the organic material layers include the compound of the present specification, that is, the hetero-cyclic compound.

When the organic light emitting device includes a plurality of organic material layers, the organic material layer may be formed of the same material or different materials.

The organic light emitting device of the present specification may be manufactured by the materials and methods known in the art, except that one or more layers of the organic material layers include the hetero-cyclic compound, that is, the compound represented by Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form an anode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a cathode, thereon. In addition to the method described above, an organic light emitting device may be made by sequentially depositing a cathode material, an organic material layer, and an anode material on a substrate.

Further, the compound of Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be manufactured by sequentially stacking a cathode material, an organic material layer, and an anode material on a substrate (International Publication No. 2003/012890). However, the manufacturing method is not limited thereto.

In an exemplary embodiment of the present specification, the first electrode is an anode, and the second electrode is a cathode.

In another exemplary embodiment, the first electrode is a cathode, and the second electrode is an anode.

As the anode material, a material having a large work function is usually preferred so as to smoothly inject holes into an organic material layer. Specific examples of the anode material which may be used in the present invention, include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly (3-methylthiophene), poly[3,4-(ethylene-1,2-dioxy)thiophene] (PEDOT), polypyrrole, and polyaniline, and the like, but are not limited thereto.

As the cathode material, a material having a small work function is usually preferred so as to smoothly inject electrons into an organic material layer. Specific examples of the cathode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes, and thus has an effect of injecting holes at an anode and an excellent effect of injecting holes for the light emitting layer or the light emitting material, prevents excitons produced from the light emitting layer from moving to an electron injection layer or an electron injection material, and is excellent in the ability to form a thin film. It is preferred that the highest occupied molecular orbital (HOMO) of the hole injection material is between the work function of the anode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from the hole injection layer and transports holes to the light emitting layer, and a hole transporting material is a material which may receive holes from an anode or a hole injection layer to transfer holes to a light emitting layer, and is suitably a material which allows large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from the hole transporting layer and the electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene (PPV)-based polymer; a Spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto. Examples of the dopant material include an organic compound, a metal, or a metal compound.

Examples of the organic compound as the dopant material include an aromatic amine derivative, a styrylamine compound, a boron complex, a fluoranthene compound, and the like. Specifically, the aromatic amine derivative is a condensed aromatic ring derivative having a substituted or unsubstituted arylamino group, and examples thereof include a pyrene, an anthracene, a chrysene, a periflanthene, and the like having an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. In addition, as the metal or the metal compound, typical metal or metal compound may be used, and specifically, a metal complex may be used. Examples of the metal complex include an iridium complex, a platinum complex, and the like, but are not limited thereto.

The electron transporting material is a material which receives electrons from an electron injection layer and transports electrons to a light emitting layer, and an electron transporting material is a material which may inject electrons well from a cathode and may transfer electrons to a light emitting layer, and is suitably a material which allows large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transporting layer may be used with any desired cathode material, as used according to the related art. In particular, examples of an appropriate cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to the hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a cathode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The electron blocking layer is a layer which serves to enhance the probability that electrons and holes are recombined by blocking electrons while transporting holes, and is a suitably a material which is significantly low in the ability to transport electrons. As a material for the electron blocking layer, the aforementioned materials for the hole transporting layer may be used if necessary, and publicly known electron blocking layers may be used without being limited thereto.

The organic light emitting device according to the present specification may be a top emission type, a bottom emission type, or a dual emission type according to the material to be used.

In an exemplary embodiment of the present specification, the hetero-cyclic compound may be included in an organic solar cell or an organic transistor in addition to the organic light emitting device.

MODE FOR INVENTION

The preparation of the hetero-cyclic compound represented by Formula 1 and the organic light emitting device including the same will be specifically described in the following Examples. However, the following Examples are provided for illustrating the present specification, and the scope of the present specification is not limited thereby.

[Preparation Example 1] Preparation of Compound P2

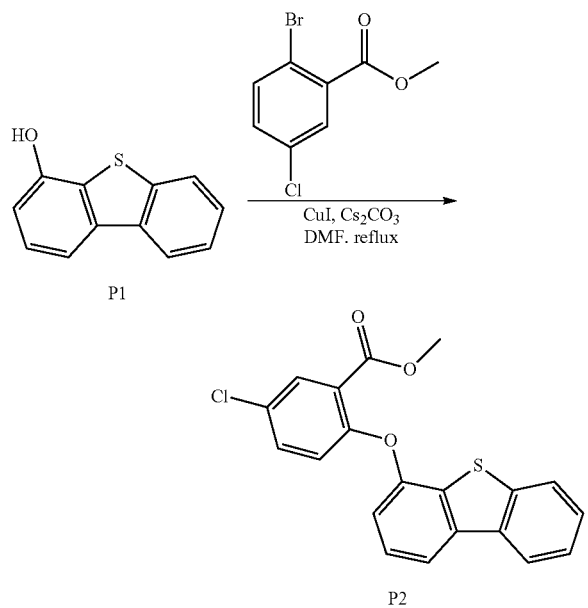

P1 (20 g, 99.8 mmol), methyl 2-bromo-5-chlorobenzoate (36 g, 144 mmol), CuI (5.2 g, 27.3 mmol), and $Cs_2CO_3$ (64 g, 196 mmol) were suspended in dimethylformamide (DMF) (150 mL). The mixture was stirred while being refluxed under an atmosphere of nitrogen for about 12 hours, and then was cooled to room temperature. 200 mL of 2 M HCl was slowly added thereto at 0° C., and then a solid produced by stirring the resulting mixture at normal temperature for 1 hour was filtered. The filtered solid was dissolved in 500 mL of $CHCl_3$, and then washed with water. The product was dried over anhydrous magnesium sulfate, and then the solvent was removed by reducing pressure. The produced solid was purified by column chromatography with hexane/ethyl acetate (10/1, v/v), thereby obtaining a white solid P2 (20 g, yield 54%).

MS: [M+H]=353

[Preparation Example 2] Preparation of Compound P3

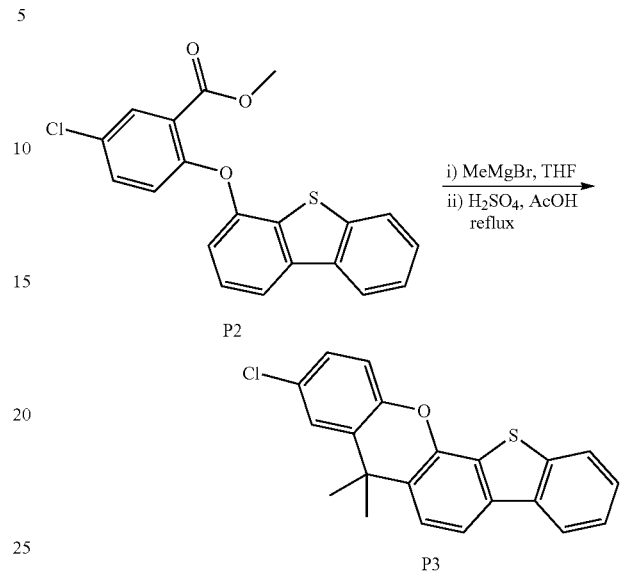

Compound P2 (20.0 g, 54.3 mmol) was dissolved in anhydrous tetrahydrofuran (THF) (300 mL), and then, a MeMgBr solution (3 M, 55 mL in an ether solution) was slowly added thereto under an atmosphere of nitrogen at 0° C. The resulting solution was stirred at normal temperature for 12 hours, and then was slowly added to a saturated $NH_4Cl$ solution (500 mL). After the mixed solution was extracted with ethyl acetate, the resulting product was dried over anhydrous magnesium sulfate, and then the solvent was removed by reducing pressure. The produced solid was suspended in AcOH without further purification, and then 0.5 mL of sulfuric acid was added dropwise thereto. The mixture was stirred while being refluxed under nitrogen for about 12 hours, and then was cooled to room temperature. The solvent was removed, and then water was added thereto. After the mixed solution was extracted with ethyl acetate, the resulting product was dried over anhydrous magnesium sulfate, and then the solvent was removed by reducing pressure. The resulting product was purified by column chromatography with hexane/ethyl acetate (10/1, v/v), thereby obtaining a white solid P3 (13 g, yield 68%).

MS: [M+H]=351

[Preparation Example 3] Preparation of Compound P4

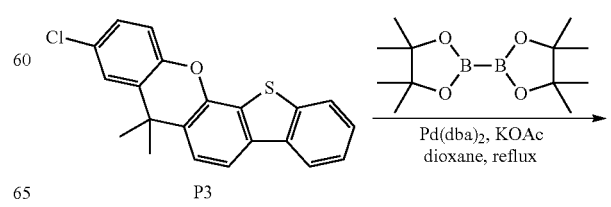

-continued

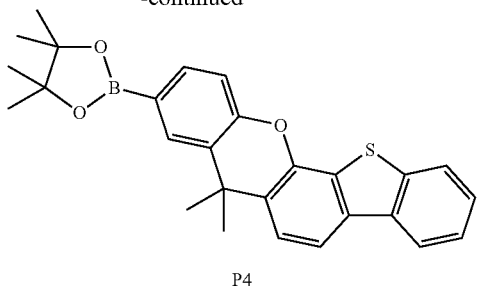

P4

Compound P3 (12.0 g, 34.2 mmol), bispinacolatodiboron (10.1 g, 39.7 mmol), Pd(dba)$_2$ (0.7 g, 1.2 mmol), PCy$_3$ (0.8 g, 2.8 mmol), and KOAc (12.5 g, 127.0 mmol) were suspended in 1,4-dioxane (150 mL). The mixture was stirred while being refluxed under an atmosphere of nitrogen for about 24 hours, and then was cooled to room temperature. The solvent was removed, and then the resulting product was dissolved in chloroform. The solution was dried over anhydrous magnesium sulfate and filtered, and then the solvent was removed by reducing pressure. The produced solid was purified by using EtOH, thereby obtaining P4 (13.7 g, yield 90%).
MS: [M+H]=443

[Preparation Example 4] Preparation of Formula P5

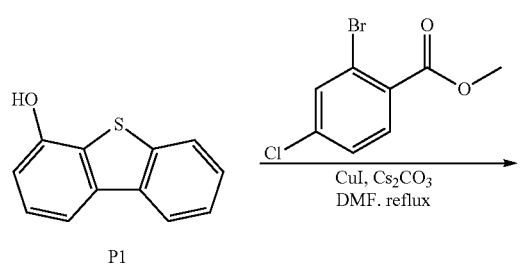

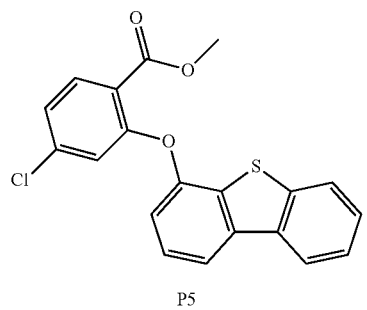

P5

Compound P5 (14.1 g, 81%) was obtained by carrying out the preparation in the same manner as in the preparation of Compound P2 in Preparation Example 1, except that methyl 2-bromo-4-chlorobenzoate (11.7 g, 46.9 mmol) was used instead of methyl 2-bromo-5-chlorobenzoate.
MS: [M+H]=369

[Preparation Example 6] Preparation of Formula P6

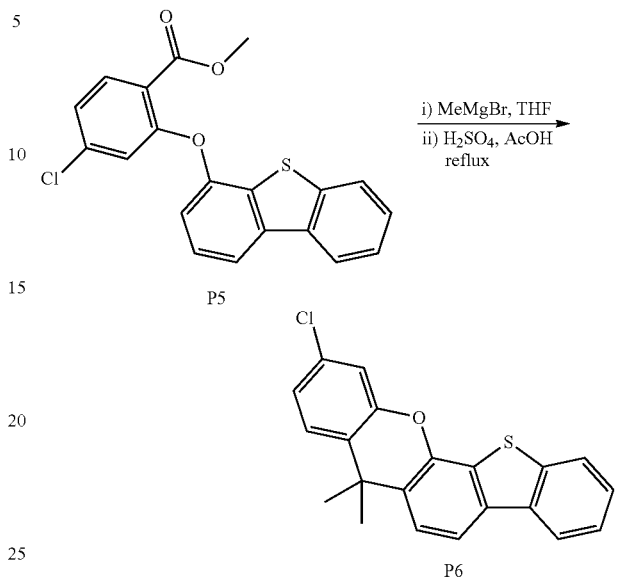

Compound P6 (8.1 g, 77.9%) was obtained by carrying out the preparation in the same manner as in the preparation of Compound P3 in Preparation Example 2, except that P5 (10.9 g, 29.5 mmol) was used instead of P2.
MS: [M+H]=351

[Preparation Example 7] Preparation of Formula P7

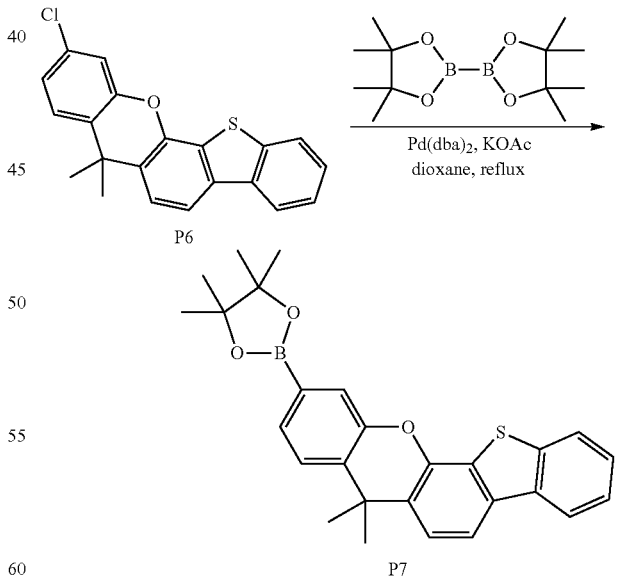

Compound P7 (6.1 g, 84.5%) was obtained by carrying out the preparation in the same manner as in the preparation of Compound P4 in Preparation Example 3, except that P6 (5.7 g, 16.2 mmol) was used instead of P3.
MS: [M+H]=443

[Preparation Example 8] Preparation of Formula P9

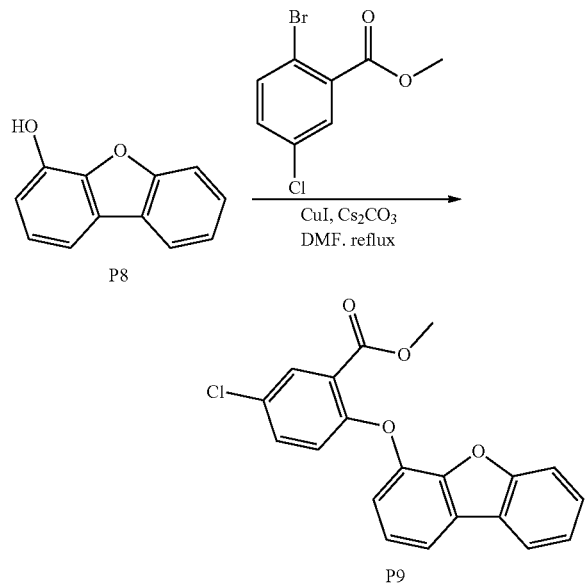

Compound P9 (16.1 g, 46.6%) was obtained by carrying out the preparation in the same manner as in the preparation of Compound P2 in Preparation Example 1, except that P8 (18.0 g, 97.7 mmol) was used instead of P1.

MS: [M+H]=353

[Preparation Example 9] Preparation of Formula P10

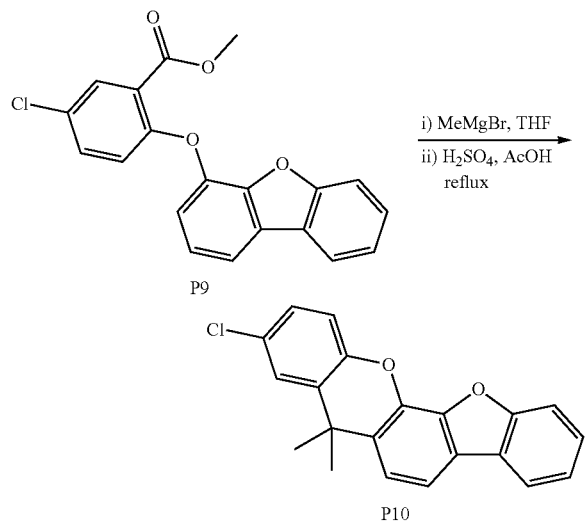

Compound P10 (7.7 g, 82.6%) was obtained by carrying out the preparation in the same manner as in the preparation of Compound P3 in Preparation Example 2, except that P9 (9.8 g, 27.7 mmol) was used instead of P2.

MS: [M+H]=335

[Preparation Example 10] Preparation of Formula P11

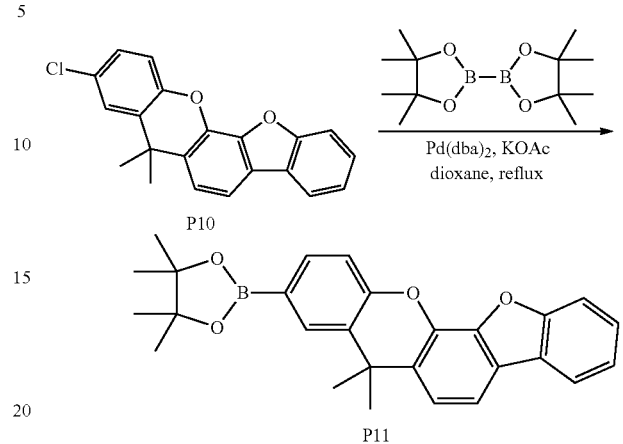

Compound P11 (5.1 g, 78.2%) was obtained by carrying out the preparation in the same manner as in the preparation of Compound P4 in Preparation Example 3, except that P10 (5.1 g, 15.2 mmol) was used instead of P3.

MS: [M+H]=427

[Preparation Example 11] Preparation of Formula P12

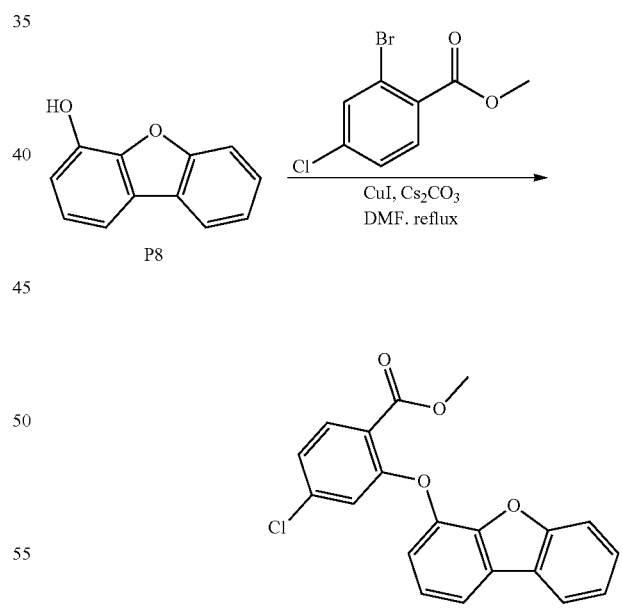

Compound P12 (13.4 g, 58%) was obtained by carrying out the preparation in the same manner as in the preparation of Compound P2 in Preparation Example 1, except that P8 (12.0 g, 65.1 mmol) was used instead of P1, and methyl 2-bromo-4-chlorobenzoate (15.5 g, 62.1 mmol) was used instead of methyl 2-bromo-5-chlorobenzoate.

MS: [M+H]=353

[Preparation Example 12] Preparation of Formula P13

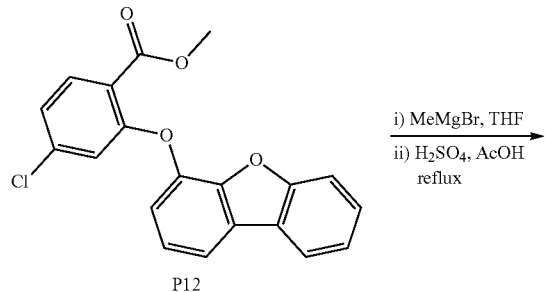

Compound P13 (8.9 g, 80.0%) was obtained by carrying out the preparation in the same manner as in the preparation of Compound P3 in Preparation Example 2, except that P12 (11.7 g, 33.1 mmol) was used instead of P2.

MS: [M+H]=335

[Preparation Example 13] Preparation of Formula P14

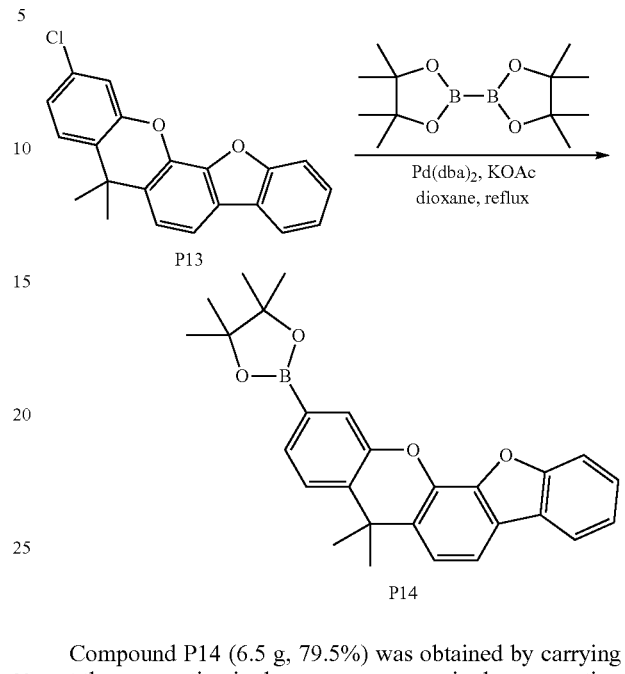

Compound P14 (6.5 g, 79.5%) was obtained by carrying out the preparation in the same manner as in the preparation of Compound P4 in Preparation Example 3, except that P13 (6.4 g, 19.1 mmol) was used instead of P3.

MS: [M+H]=427

[Preparation Example 14] Preparation of Formula 2-2

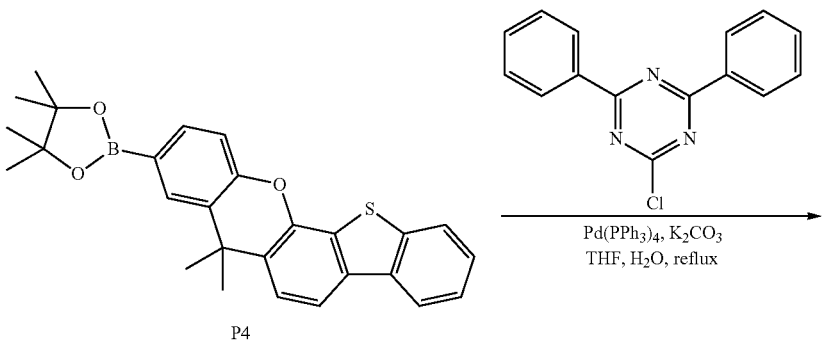

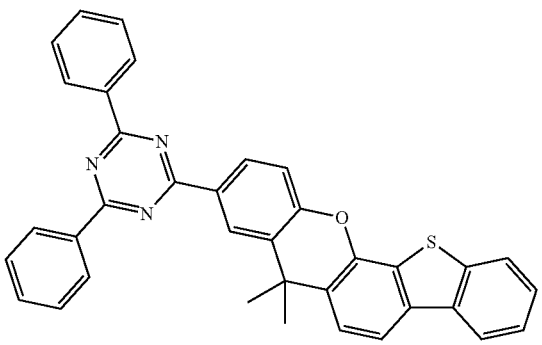

P4 (12.0 g, 27.1 mmol), 2-chloro-4,6-diphenyl-1,3,5-triazine (7.5 g, 28.0 mmol), Pd(PPh$_3$)$_4$ (0.7 g, 1.2 mmol), and K$_2$CO$_3$ (12 g, 86.8 mmol) were suspended in tetrahydrofuran (THF) (100 mL). The mixture was stirred while being refluxed under an atmosphere of nitrogen for about 24 hours, and then was cooled to room temperature. The solvent was removed, and then the resulting product was dissolved in chloroform. The solution was dried over anhydrous magnesium sulfate and filtered, and then the solvent was removed by reducing pressure. The produced solid was purified with THF/toluene, thereby obtaining a white solid compound (10.3 g, yield 69%) represented by Formula 2-2.

MS: [M+H]=548

[Preparation Example 15] Preparation of Formula 2-8

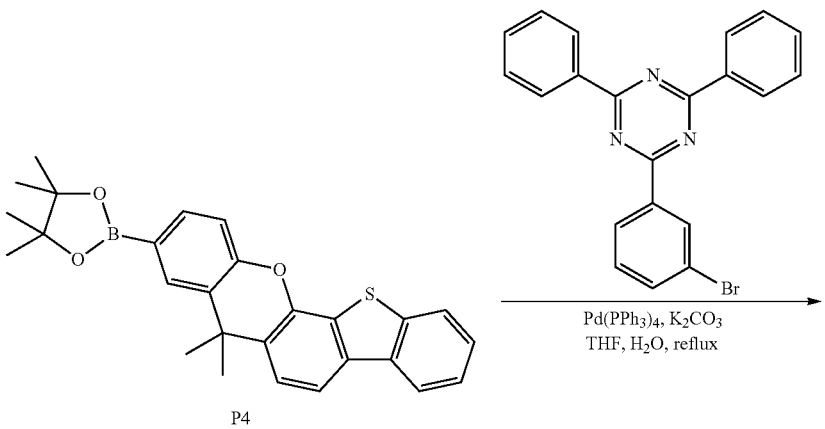

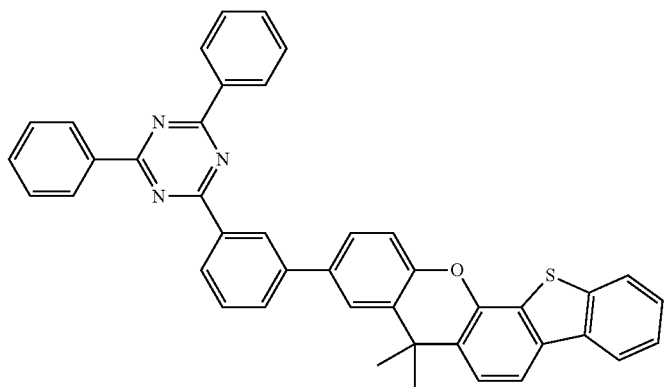

Compound 2-8 (8.9 g, 64.8%) was obtained by carrying out the preparation in the same manner as in the preparation of Compound 2-2 in Preparation Example 14, except that 2-(3-bromophenyl)-4,6-diphenyl-1,3,5-triazine (9.7 g, 21.9 mmol) was used instead of 2-chloro-4,6-diphenyl-1,3,5-triazine.

MS: [M+H]=624

[Preparation Example 16] Preparation of Formula 2-18
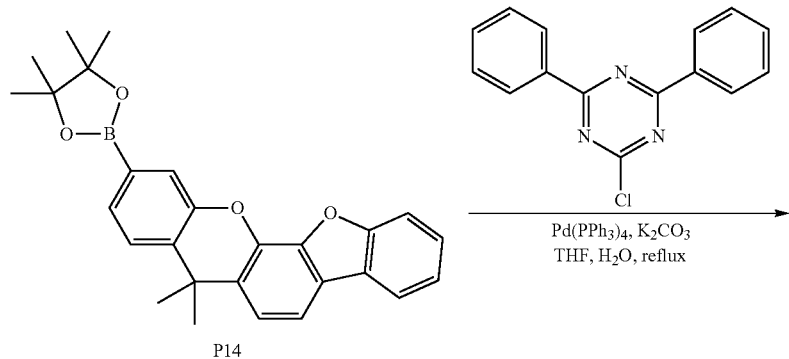
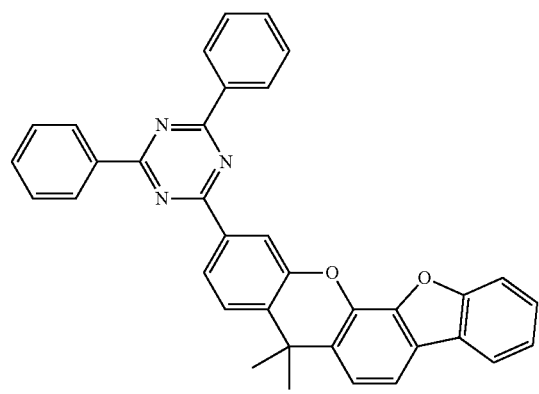
Compound 2-18 (7.3 g, 74.0%) was obtained by carrying out the preparation in the same manner as in the preparation of Compound 2-2 in Preparation Example 14, except that P14 (7.9 g, 18.5 mmol) was used instead of P4.
MS: [M+H]=532
[Preparation Example 17] Preparation of Formula 2-31
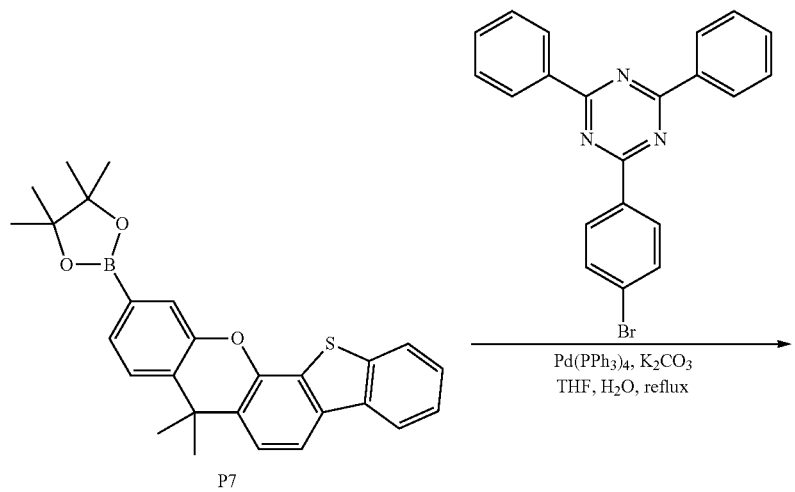

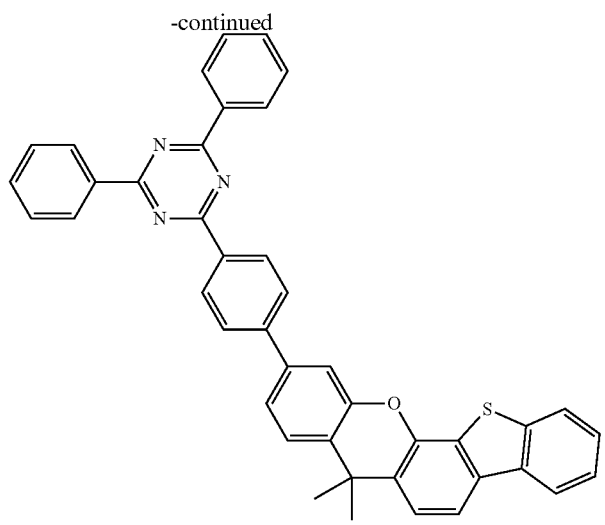

Compound 2-31 (8.9 g, 64.8%) was obtained by carrying out the preparation in the same manner as in the preparation of Compound 2-2 in Preparation Example 14, except that P7 (9.7 g, 21.9 mmol) was used instead of P4, and 2-(4-bromophenyl)-4,6-diphenyl-1,3,5-triazine (9.7 g, 21.9 mmol) was used instead of 2-chloro-4,6-diphenyl-1,3,5-triazine.

MS: [M+H]=624

[Preparation Example 18] Preparation of Formula 2-56

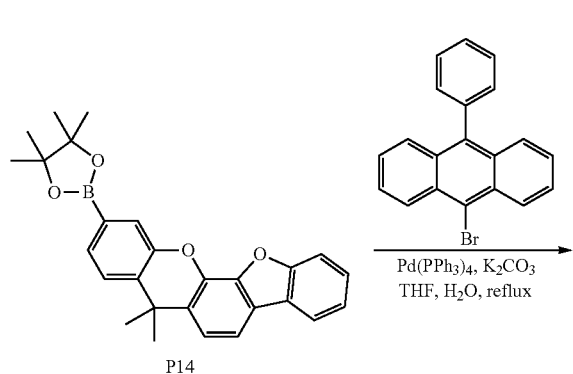

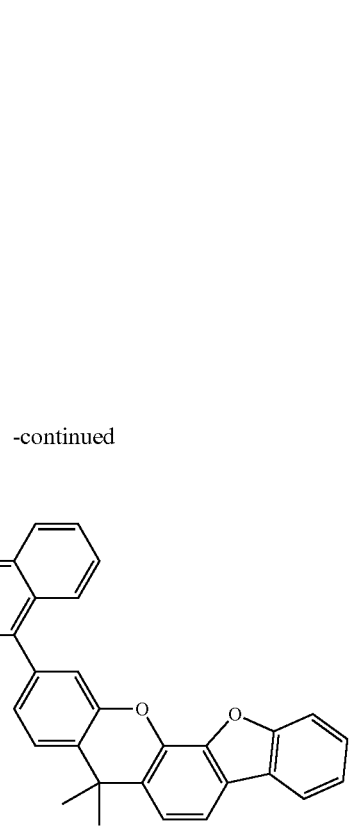

Compound 2-56 (6.3 g, 70.0%) was obtained by carrying out the preparation in the same manner as in the preparation of Compound 2-2 in Preparation Example 14, except that P14 (6.7 g, 15.7 mmol) was used instead of P4, and 9-bromo-10-phenylanthracene (5.4 g, 16.2 mmol) was used instead of 2-chloro-4,6-diphenyl-1,3,5-triazine.

MS: [M+H]=567

[Preparation Example 19] Preparation of Formula 2-72

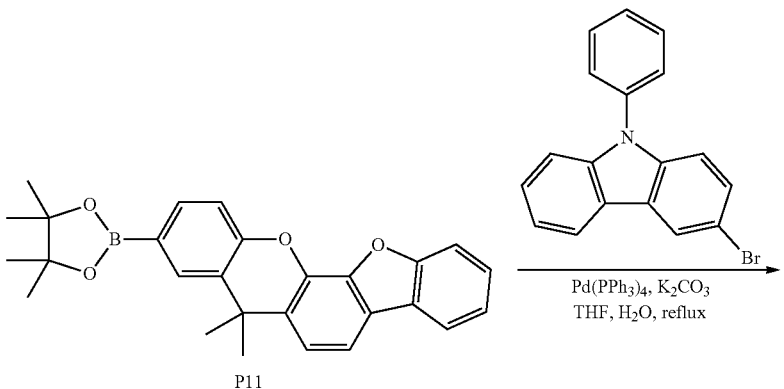

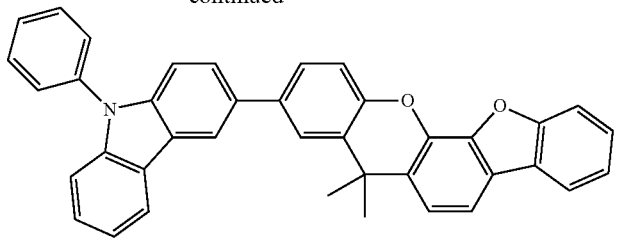

Compound 2-72 (6.0 g, 64.4%) was obtained by carrying out the preparation in the same manner as in the preparation of Compound 2-2 in Preparation Example 14, except that P11 (7.1 g, 16.6 mmol) was used instead of P4, and 3-bromo-9-phenyl-9H-carbazole (5.4 g, 16.7 mmol) was used instead of 2-chloro-4,6-diphenyl-1,3,5-triazine.

MS: [M+H]=558

[Preparation Example 20] Preparation of Formula 2-76

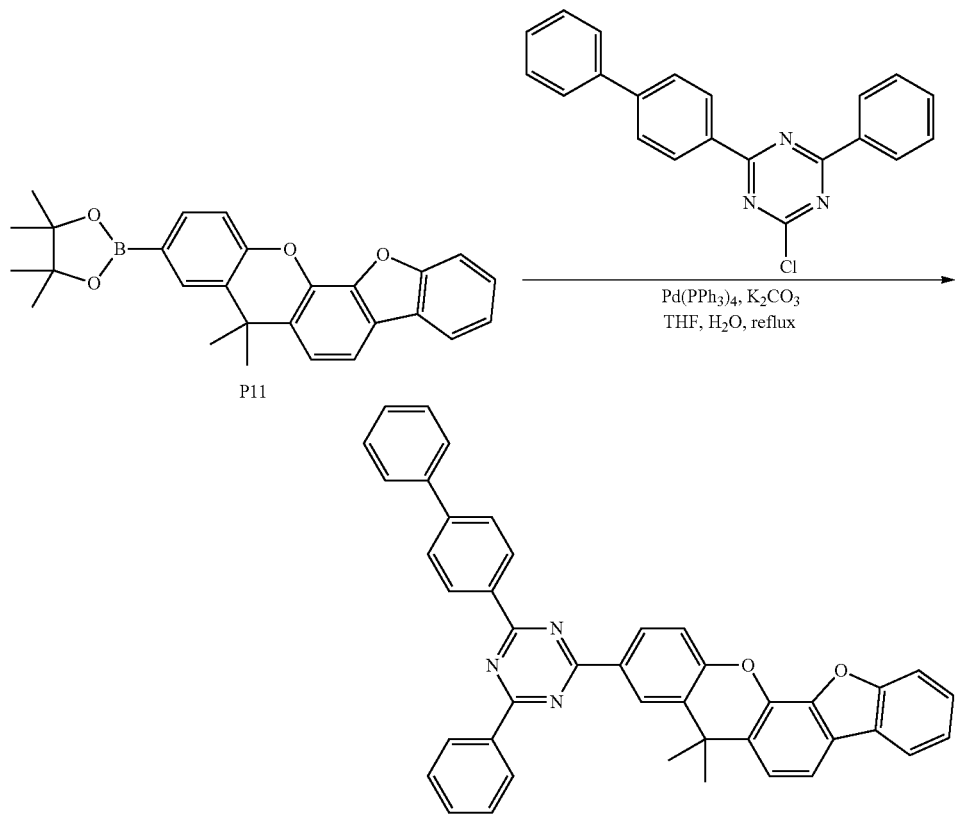

Compound 2-76 (7.5 g, 75.0%) was obtained by carrying out the preparation in the same manner as in the preparation of Compound 2-2 in Preparation Example 14, except that P11 (7.0 g, 16.4 mmol) was used instead of P4, and 2-([1,1'-biphenyl]-4-yl)-4-chloro-6-phenyl-1,3,5-triazine (5.7 g, 16.5 mmol) was used instead of 2-chloro-4,6-diphenyl-1,3,5-triazine.

MS: [M+H]=608

[Preparation Example 21] Preparation of Formula 2-79

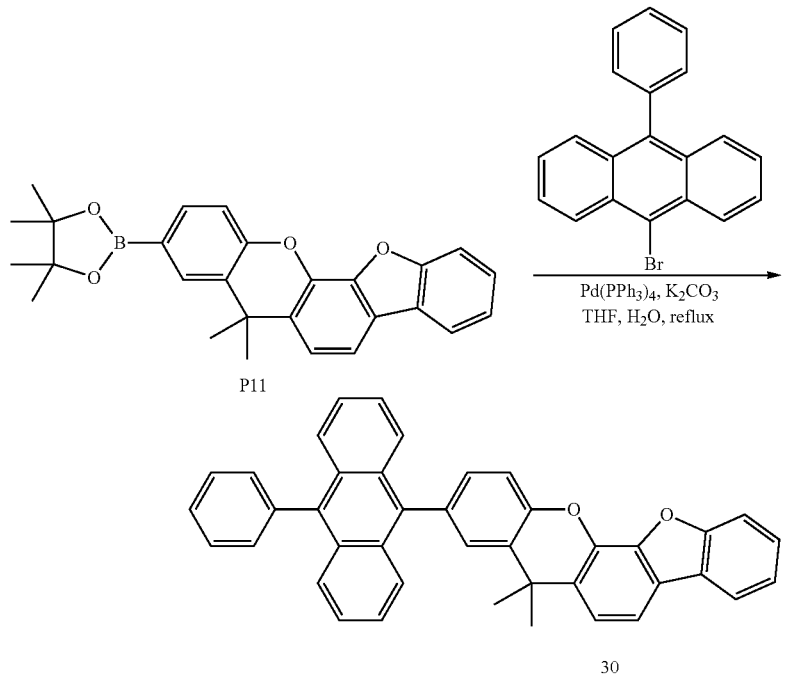

Compound 2-79 (7.7 g, 75.1%) was obtained by carrying out the preparation in the same manner as in the preparation of Compound 2-2 in Preparation Example 14, except that P11 (7.9 g, 18.5 mmol) was used instead of P4, and 9-bromo-10-phenylanthracene (6.5 g, 19.5 mmol) was used instead of 2-chloro-4,6-diphenyl-1,3,5-triazine.

MS: [M+H]=553

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted. Hexanitrile hexaazatriphenylene was vacuum deposited to have a thickness of 500 Å by heating on a transparent ITO electrode, which was thus prepared, thereby forming a hole injection layer. HT-1 (400 Å), which is a material transporting holes, was vacuum deposited thereon, and then Compound 2-56, which was synthesized in Preparation Example 18 as a host of a light emitting layer, and a dopant D1 compound were vacuum deposited to have a thickness of 300 Å. And then, the E1 compound (300 Å) was vacuum deposited by heating sequentially as an electron injection layer and an electron transporting layer. A negative electrode was formed by sequentially depositing lithium fluoride (LiF) and aluminum to have a thickness of 12 Å and 2,000 Å, respectively, on the electron transporting layer, thereby manufacturing an organic light emitting device. In the aforementioned procedure, the deposition rates of the organic material, lithium fluoride, and aluminum were maintained at 1 Å/sec, 0.2 Å/sec, and 3 to 7 Å/sec, respectively.

[Hexanitrile hexaazatriphenylene]:

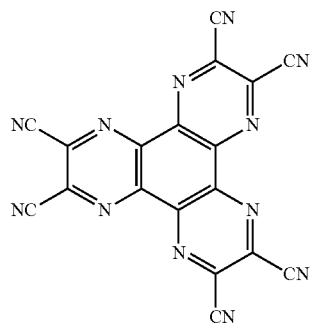

[HT1]:

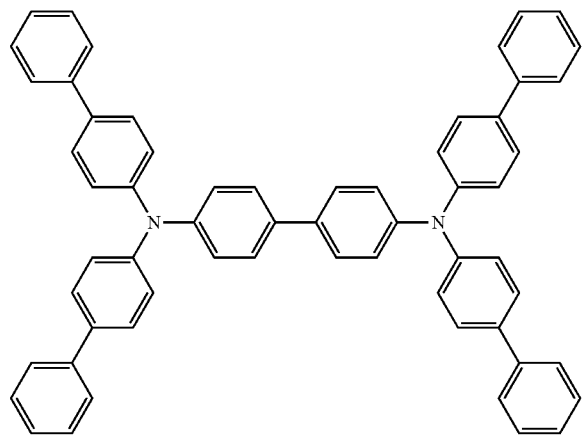

-continued

[NPB]:

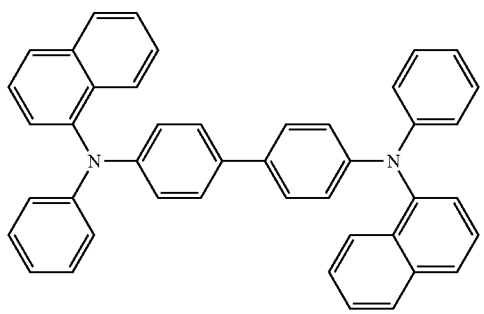

[H1]:

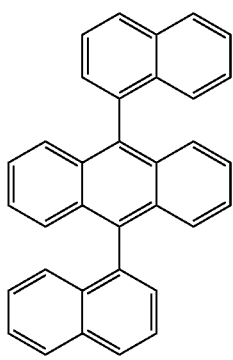

[D1]:

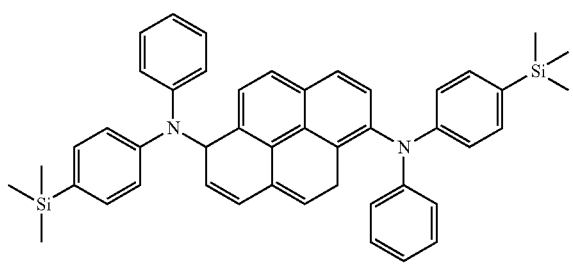

[H2]:

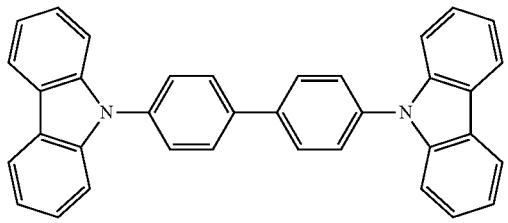

-continued

[E1]:

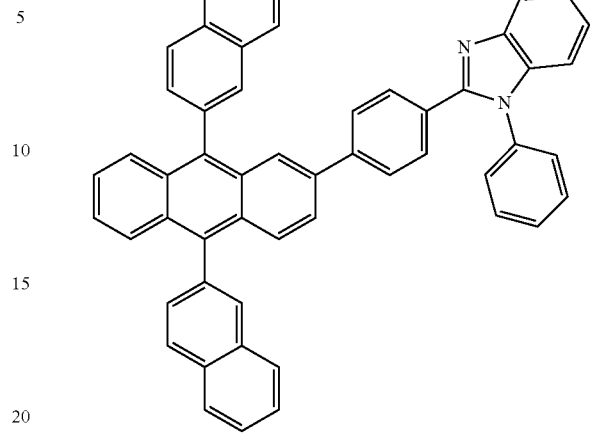

Example 2

An experiment was performed in the same manner as in Example 1, except that as the host of the light emitting layer, Compound 2-79 was used instead of Compound 2-56 synthesized in Preparation Example 18.

Comparative Example 1

An experiment was performed in the same manner as in Example 1, except that as the host of the light emitting layer, H1 was used instead of Compound 2-56 synthesized in Preparation Example 18.

The experimental results are shown in the following Table 1.

TABLE 1

| Experimental Example (50 mA/cm$^2$) | Host material | Voltage (V) | Current efficiency (Cd/A) |
|---|---|---|---|
| Comparative Example 1 | H1 | 6.13 | 5.85 |
| Example 1 | 2-56 | 5.5 | 6.01 |
| Example 2 | 2-79 | 5.61 | 5.9 |

As shown in Table 1, the compound derivatives of Formulae according to the present invention may exhibit excellent characteristics in efficiency and driving voltage in an organic electronic device including an organic light emitting device.

Example 3

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted. Hexanitrile hexaazatriphenylene was vacuum deposited to have a thickness of 500 Å by heating on a transparent ITO electrode, which was thus prepared, thereby forming a hole injection layer. NPB (400 Å), which is a material transporting holes, was vacuum deposited thereon, and then Compound 2-2, which was synthesized in Preparation Example 14 as a host of a light emitting layer, and an Ir(ppy)$_3$ dopant were vacuum deposited to have a thickness of 300 Å at a 10% concentration. And then, the E1 compound (200 Å) was vacuum deposited by heating sequentially as an electron injection layer and an electron transporting layer. A negative electrode was formed by sequentially depositing lithium fluoride (LiF) and aluminum to have a thickness of 12 Å and 2,000 Å, respectively, on the electron transporting layer, thereby manufacturing an organic light emitting device. In the aforementioned procedure, the deposition rates of the organic material, lithium fluoride, and aluminum were maintained at 1 Å/sec, 0.2 Å/sec, and 3 to 7 Å/sec, respectively.

Example 4

An experiment was performed in the same manner as in Example 3, except that as the host of the light emitting layer, Compound 2-8 was used instead of Compound 2-2 synthesized in Preparation Example 14.

Example 5

An experiment was performed in the same manner as in Example 3, except that as the host of the light emitting layer, Compound 2-18 was used instead of Compound 2-2 synthesized in Preparation Example 14.

Example 6

An experiment was performed in the same manner as in Example 3, except that as the host of the light emitting layer, Compound 2-32 was used instead of Compound 2-2 synthesized in Preparation Example 14.

Example 7

An experiment was performed in the same manner as in Example 3, except that as the host of the light emitting layer, Compound 2-76 was used instead of Compound 2-2 synthesized in Preparation Example 14.

Example 8

An experiment was performed in the same manner as in Example 3, except that as the host of the light emitting layer, Compounds 2-76 and 2-72 were used instead of Compound 2-2 synthesized in Preparation Example 14.

Comparative Example 2

An experiment was performed in the same manner as in Example 3, except that as the host of the light emitting layer, H2 was used instead of Compound 2-2 synthesized in Preparation Example 14.

The experimental results are shown in the following Table 2.

TABLE 2

| No. | Host | Dopant | Doping concentration (%) | Driving voltage (V) @5,000 cd/m$^2$ | Light emitting efficiency (Cd/A) |
|---|---|---|---|---|---|
| Comparative Example 1 | H2 | Ir(ppy)$_3$ | 10 | 5.2 | 36 |
| Example 3 | Formula 2-2 | Ir(ppy)$_3$ | 10 | 4.7 | 41 |
| Example 4 | Formula 2-8 | Ir(ppy)$_3$ | 10 | 4.9 | 40 |
| Example 5 | Formula 2-18 | Ir(ppy)$_3$ | 10 | 5.0 | 44 |
| Example 6 | Formula 2-32 | Ir(ppy)$_3$ | 10 | 5.1 | 43 |
| Example 7 | Formula 2-76 | Ir(ppy)$_3$ | 10 | 4.9 | 40 |
| Example 8 | Formula 2-76 and Formula 2-72 | Ir(ppy)$_3$ | 10 | 4.5 | 41 |

As shown in Table 2, the compound derivatives of Formulae according to the present invention may exhibit excellent characteristics in efficiency and driving voltage in an organic electronic device including an organic light emitting device.

EXPLANATION OF REFERENCE NUMERALS AND SYMBOLS

101: Substrate
201: Anode
301: Light emitting layer
401: Cathode
501: Hole injection layer
601: Hole transporting layer
701: Electron transporting layer
801: Electron injection layer

The invention claimed is:

1. A hetero-cyclic compound represented by the following Formula 1:

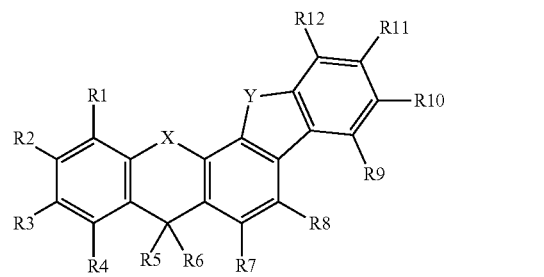

[Formula 1]

in Formula 1,
X and Y are each independently O or S,
R1 to R12 are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted aryl group; a substituted or unsubstituted fluorenyl group; a substituted or unsubstituted carbazole group; or a substituted or unsubstituted hetero-cyclic group comprising one or more of N, O and S atoms, provided that at least one of R1 to R4 is each independently represented by (L)$_n$-A, n is an integer of 0 to 4, L comprises at least one of: a substituted or unsubstituted arylene group, and one or more selected from the group consisting of a substituted or unsubstituted divalent hetero-cyclic group including one or more of N, O and S atoms, and when n is 2 to 4, a plurality of L's is optionally the same as or different from each other, and A is a substituted or unsubstituted hetero-cyclic group; or a substituted or unsubstituted aryl group.

2. The hetero-cyclic compound of claim 1, wherein R2 or R3 is represented by -(L)$_n$-A, n is 0 or 1, L is a substituted or unsubstituted phenylene group; a substituted or unsubstituted biphenylene group; a substituted or unsubstituted divalent naphthalene group; or a substituted or unsubstituted anthracenylene group, and A is a substituted or unsubstituted hetero-cyclic group; or a substituted or unsubstituted aryl group.

3. The hetero-cyclic compound of claim 2, wherein R5 and R6 are a substituted or unsubstituted alkyl group.

4. The hetero-cyclic compound of claim 1, wherein A is a substituted or unsubstituted pyridine group; a substituted or unsubstituted pyrimidine group; a substituted or unsubstituted pyridazine group; a substituted or unsubstituted pyrazine group; a substituted or unsubstituted triazine group; a substituted or unsubstituted tetrazine group; a pentazine group; a substituted or unsubstituted carbazole group; a substituted or unsubstituted dibenzofuranyl group; a substituted or unsubstituted dibenzothiophene group; a substituted or unsubstituted phenyl group; a substituted or unsubstituted biphenyl group; a substituted or unsubstituted naphthyl group; a substituted or unsubstituted phenanthrenyl group; a substituted or unsubstituted anthracenyl group; a substituted or unsubstituted fluorenyl group; a substituted or unsubstituted spiro bifluorenyl group; a substituted or unsubstituted fluoranthene group; or a substituted or unsubstituted triphenylene group.

5. The hetero-cyclic compound of claim 1, wherein the hetero-cyclic compound represented by Formula 1 is represented by the following Formula 1-1 or 1-2:

[Formula 1-1]

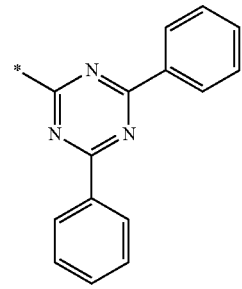

[Formula 1-2]

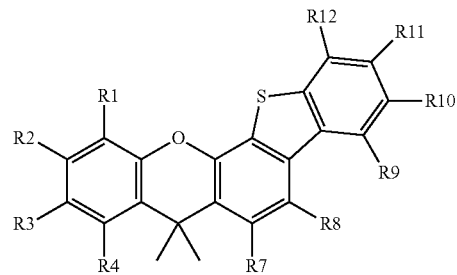

in Formulae 1-1 and 1-2, a definition of R1 to R4 and R7 to R12 is the same as those in claim 1.

6. The hetero-cyclic compound of claim 1, wherein -(L) n-A is any one substituent of the following Substituents 1-1 to 1-41, which are substituted or unsubstituted:

Substituent 1-1

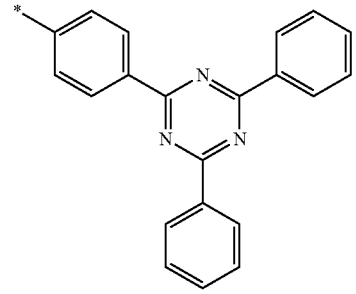

Substituent 1-2

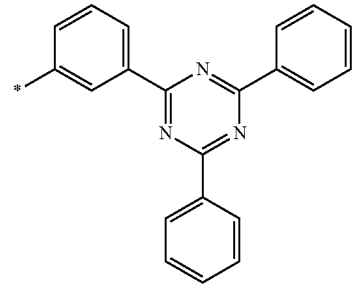

Substituent 1-3

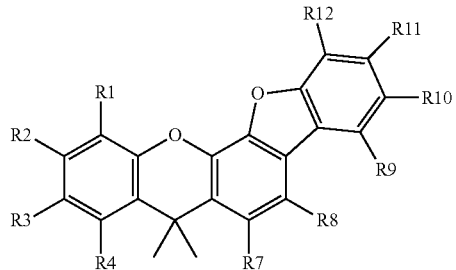

Substituent 1-4

Substituent 1-5

Substituent 1-6

Substituent 1-7

Substituent 1-8

Substituent 1-9

Substituent 1-10

Substituent 1-11

Substituent 1-12

Substituent 1-13

Substituent 1-14

Substituent 1-15
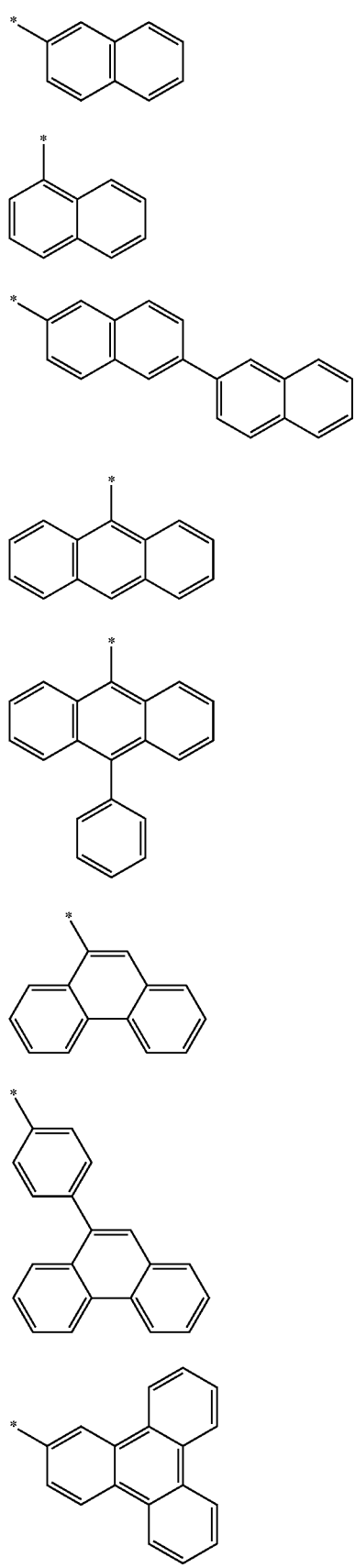
Substituent 1-16
Substituent 1-17
Substituent 1-18
Substituent 1-19
Substituent 1-20
Substituent 1-21
Substituent 1-22
Substituent 1-23
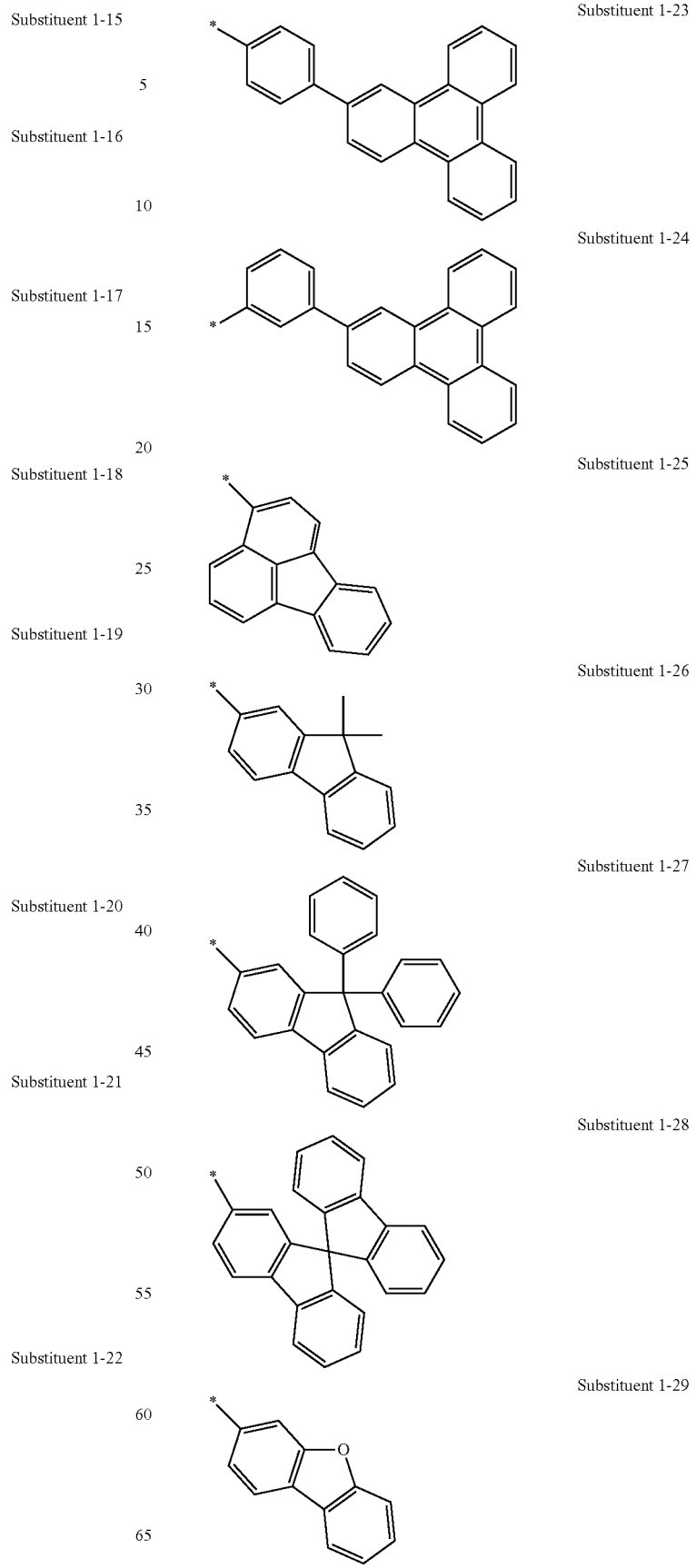
Substituent 1-24
Substituent 1-25
Substituent 1-26
Substituent 1-27
Substituent 1-28
Substituent 1-29

Substituent 1-30
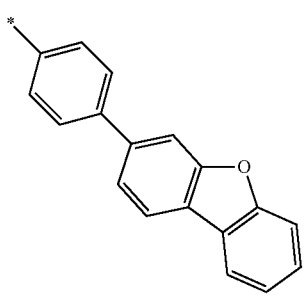
Substituent 1-31
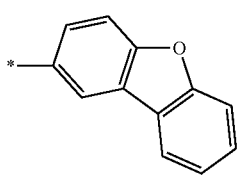
Substituent 1-32
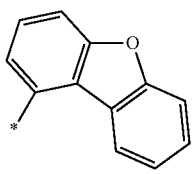
Substituent 1-33
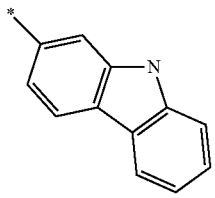
Substituent 1-34
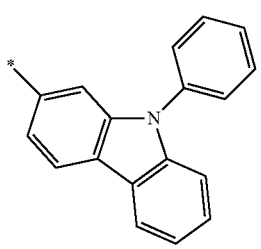
Substituent 1-35
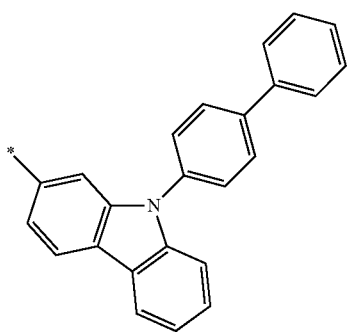
Substituent 1-36
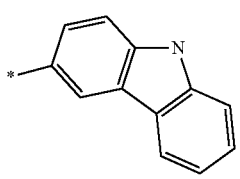
Substituent 1-37
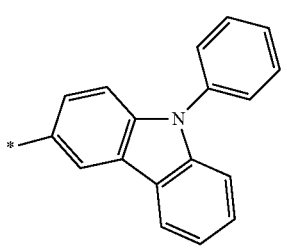
Substituent 1-38
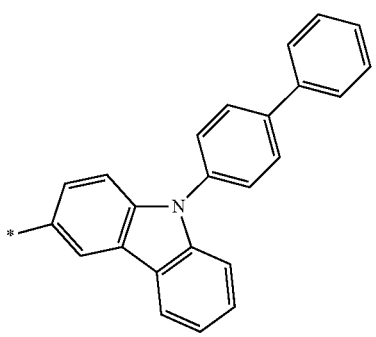
Substituent 1-39
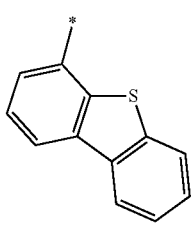
Substituent 1-40
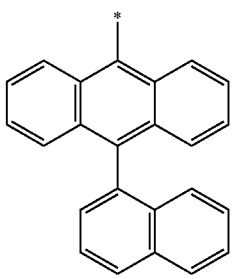
Substituent 1-41
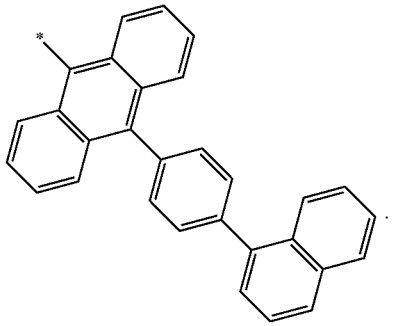
7. The hetero-cyclic compound of claim 1, wherein the compound represented by Formula 1 is a compound represented by any one of the following Formulae 2-1 to 2-81:

Formula 2-1
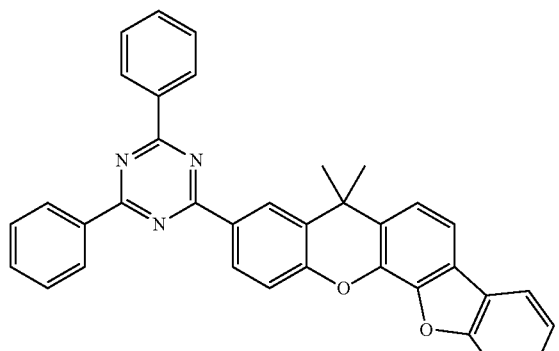
Formula 2-2
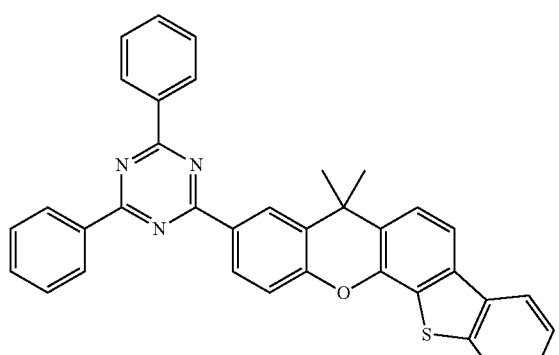
Formula 2-3
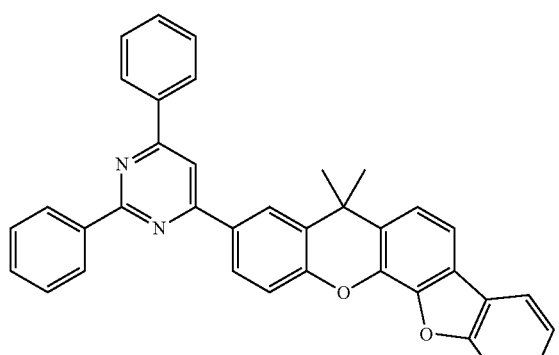
Formula 2-4
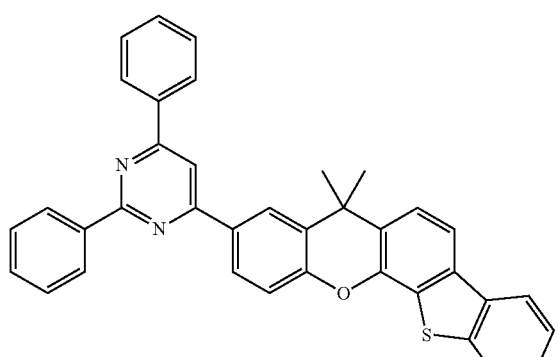
Formula 2-5
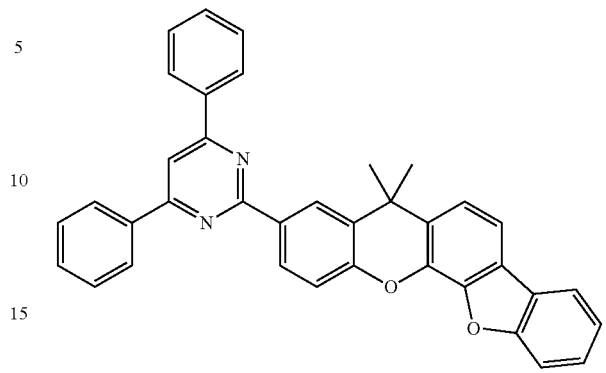
Formula 2-6
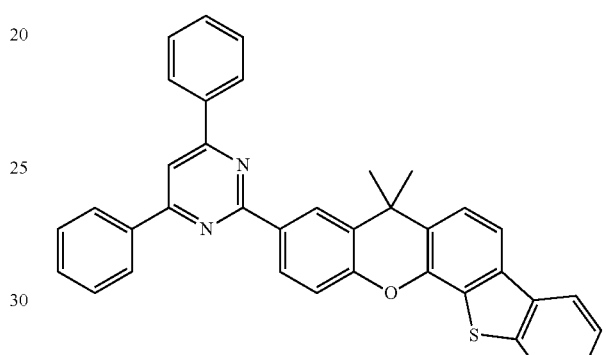
Formula 2-7
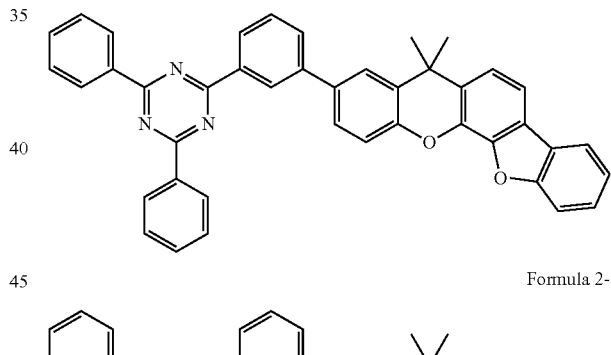
Formula 2-8
Formula 2-9
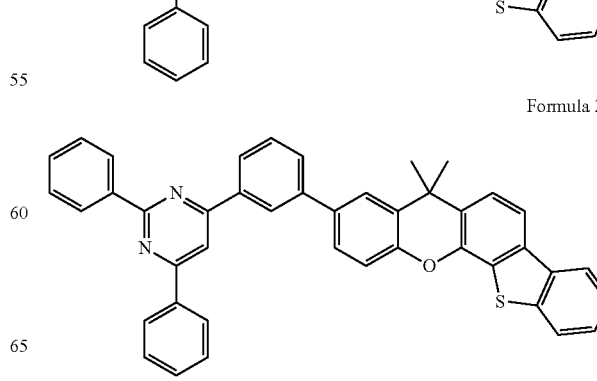

Formula 2-10
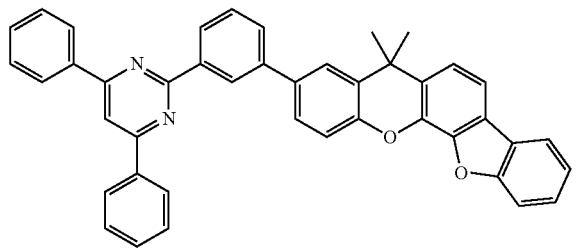
Formula 2-11
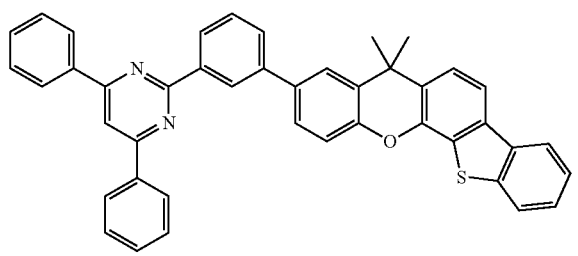
Formula 2-12
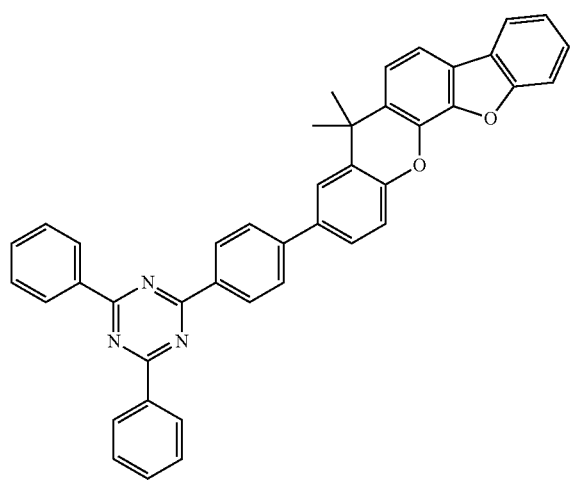
Formula 2-13
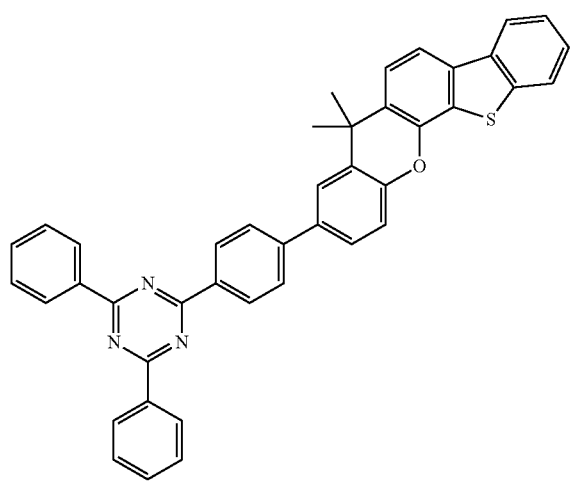
Formula 2-14
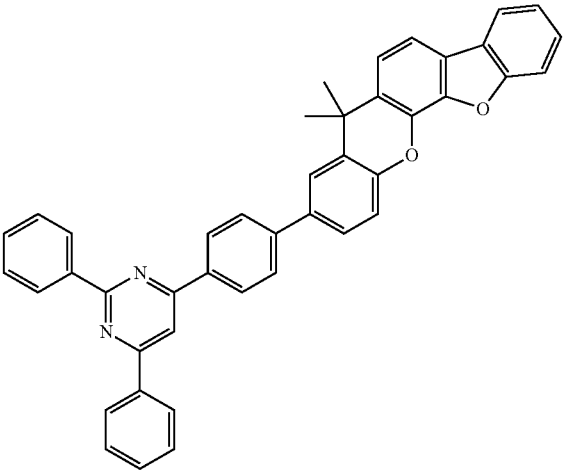
Formula 2-15
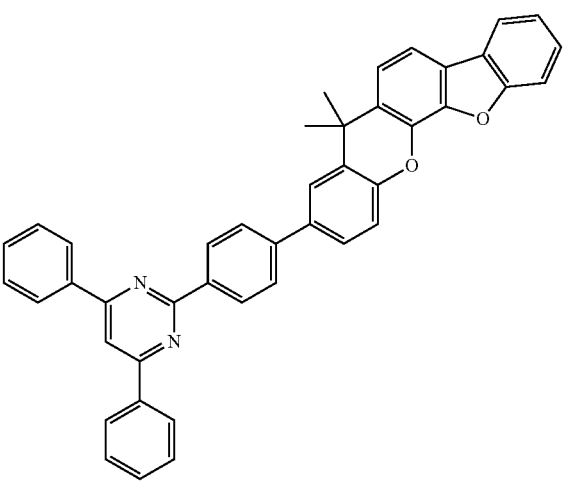
Formula 2-16

Formula 2-17
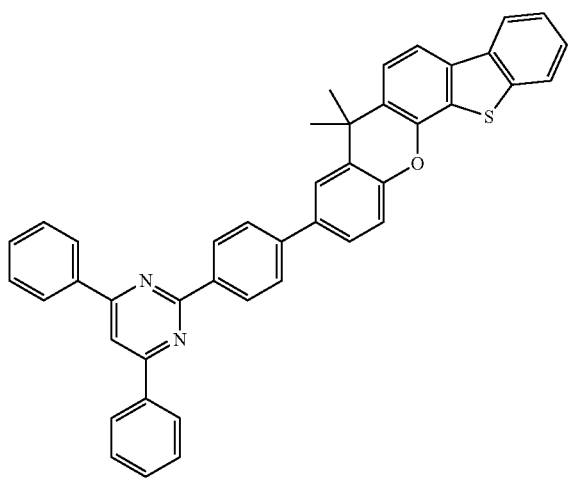
Formula 2-18
Formula 2-19
Formula 2-20
Formula 2-21
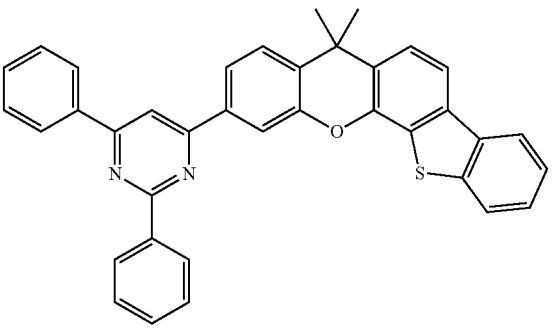
Formula 2-22
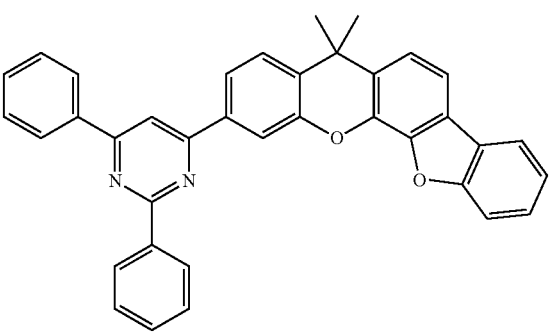
Formula 2-23
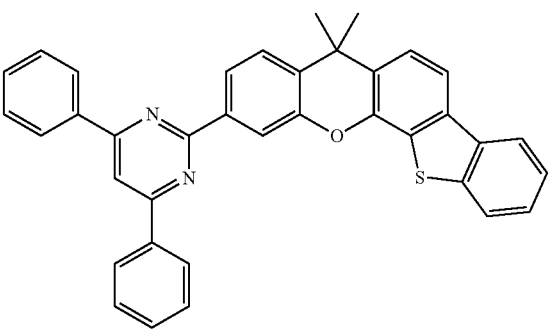
Formula 2-24
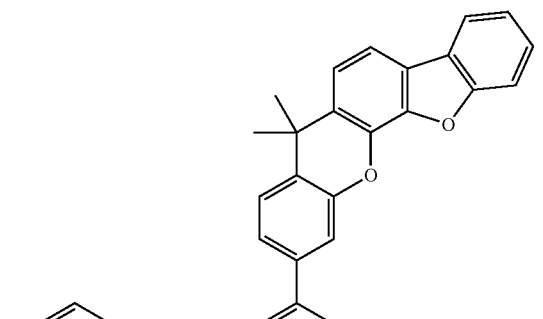

Formula 2-25
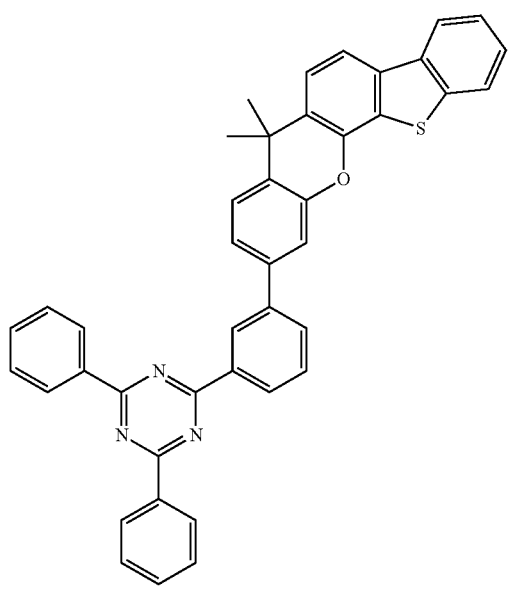
Formula 2-27
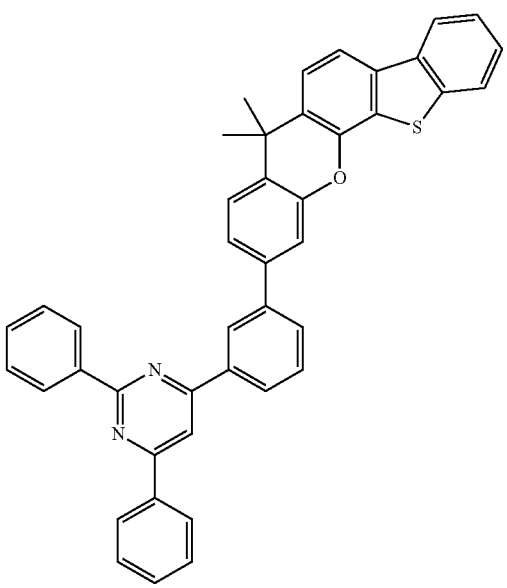
Formula 2-26
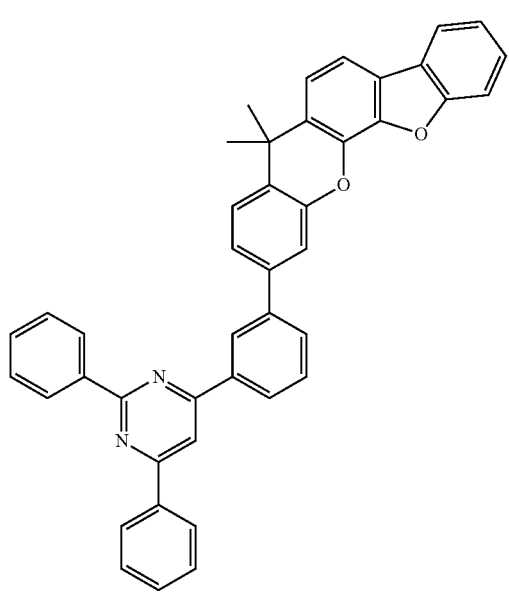
Formula 2-28
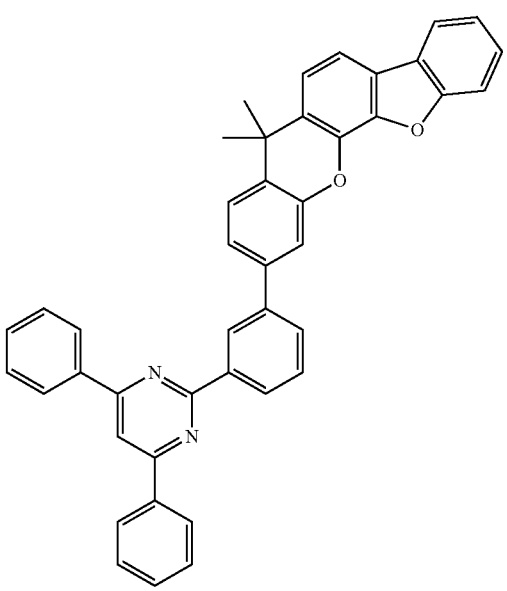

Formula 2-29
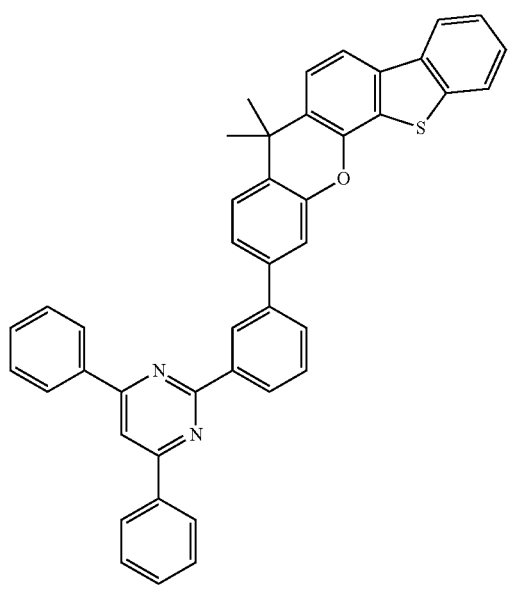
Formula 2-30
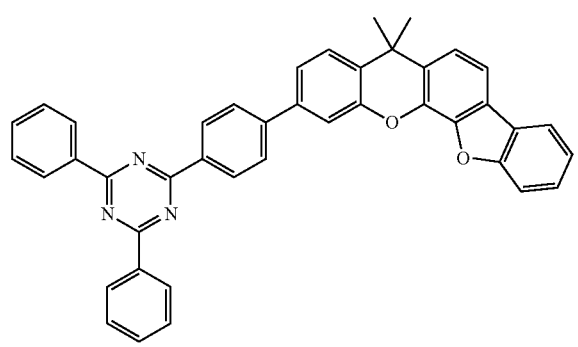
Formula 2-31
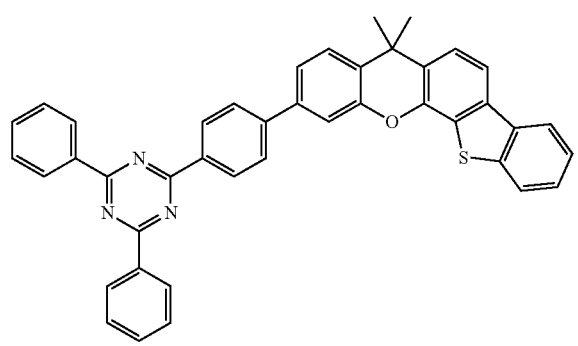
Formula 2-32
Formula 2-33
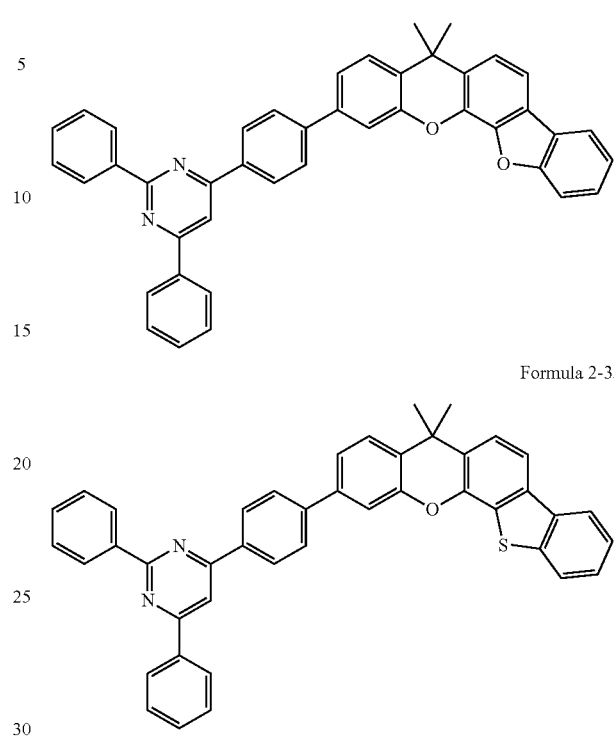
Formula 2-34
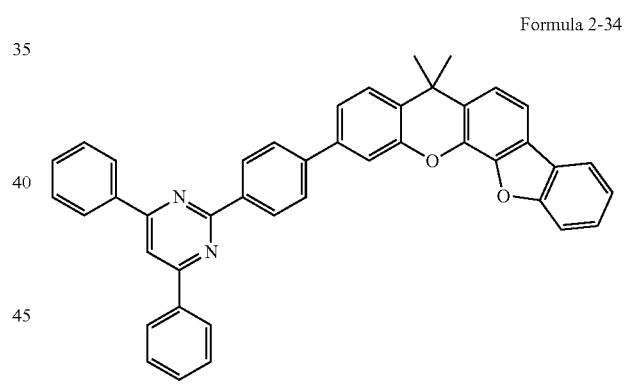
Formula 2-35
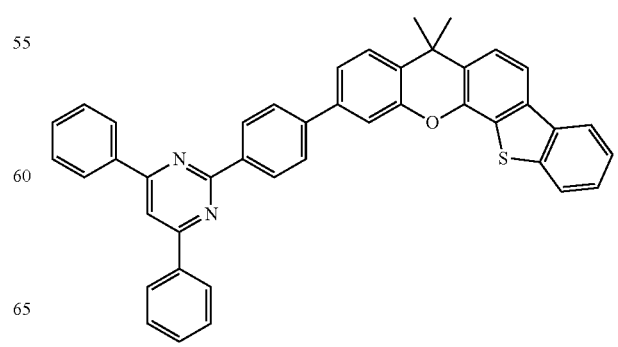

-continued
Formula 2-36
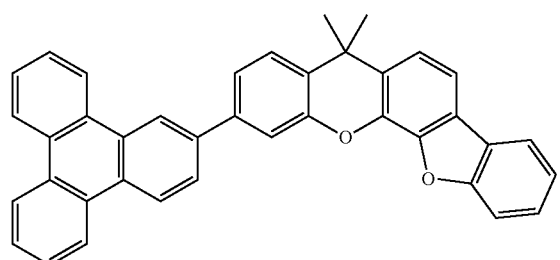
Formula 2-37
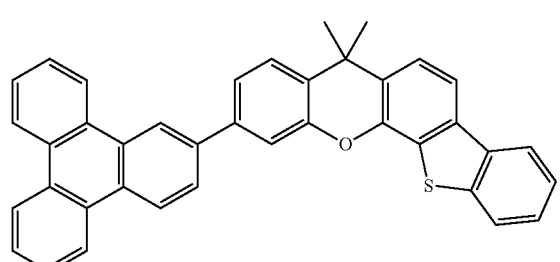
Formula 2-38
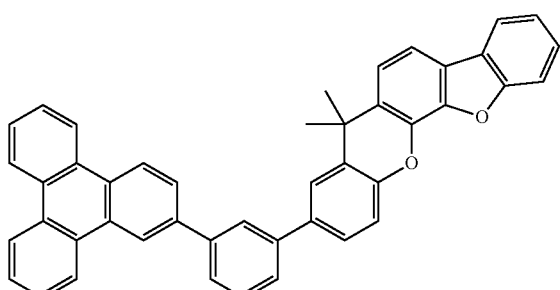
Formula 2-39
Formula 2-40
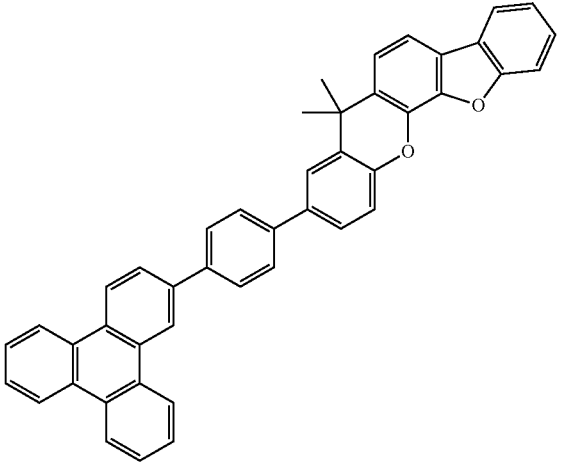
Formula 2-41
Formula 2-42
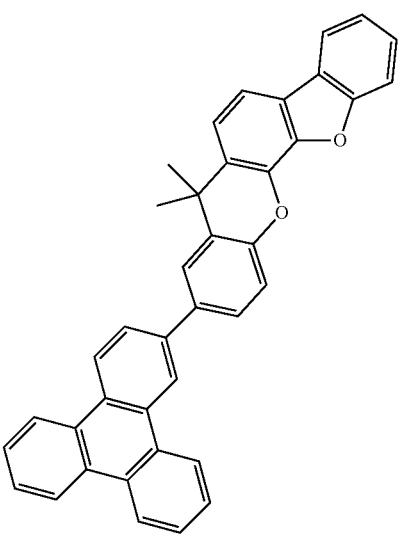

Formula 2-43
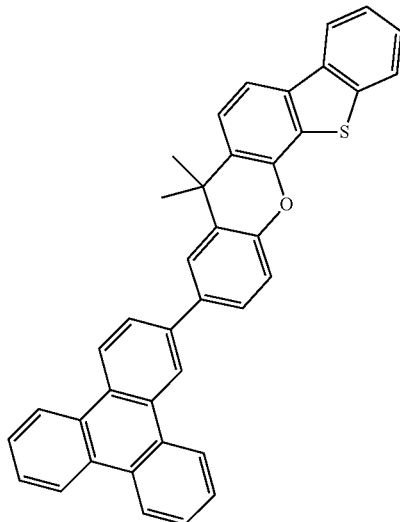
Formula 2-44
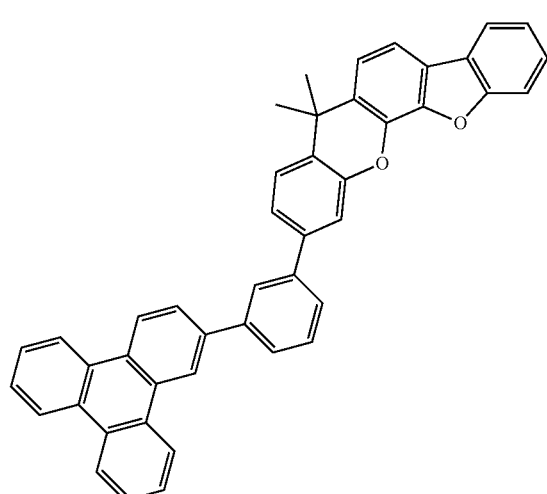
Formula 2-45
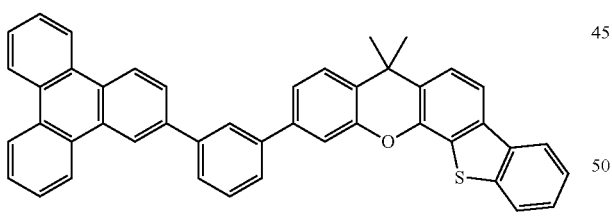
Formula 2-46
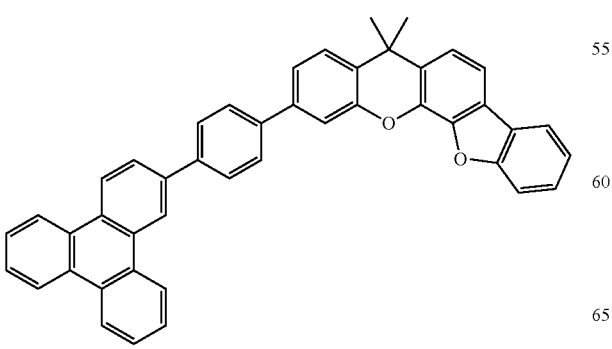
Formula 2-47
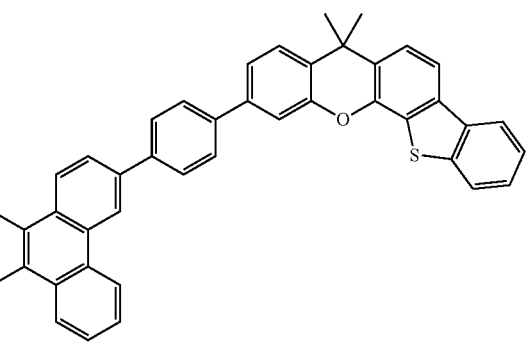
Formula 2-48
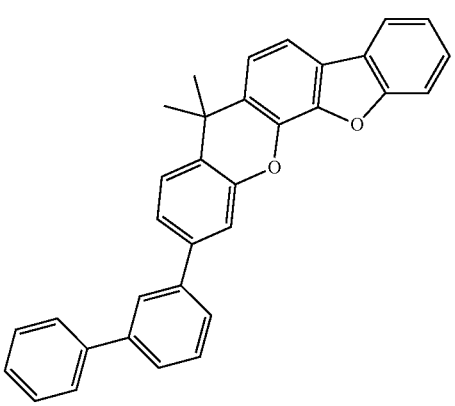
Formula 2-49
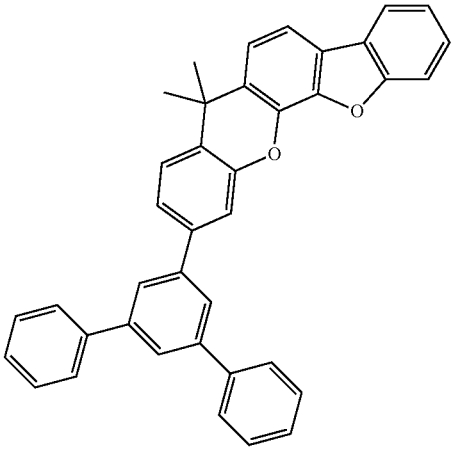

Formula 2-50
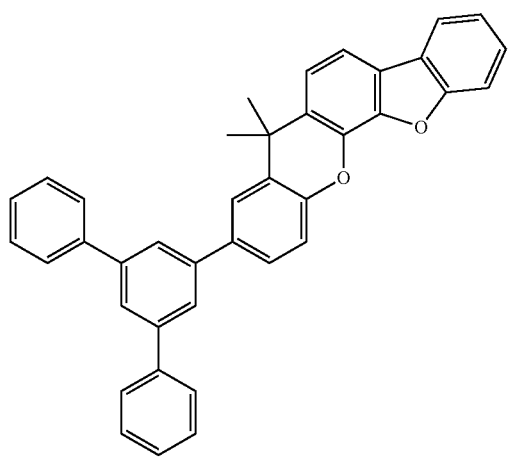
Formula 2-51
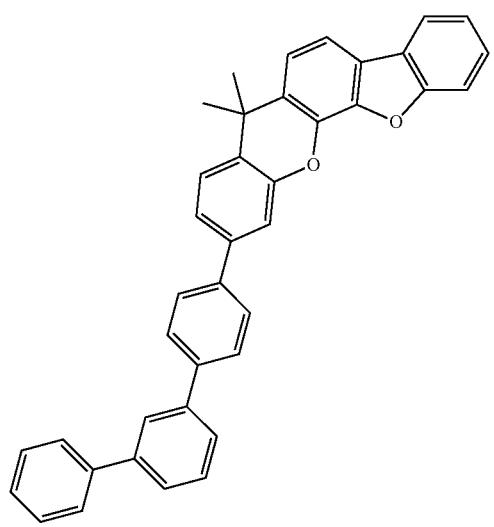
Formula 2-52
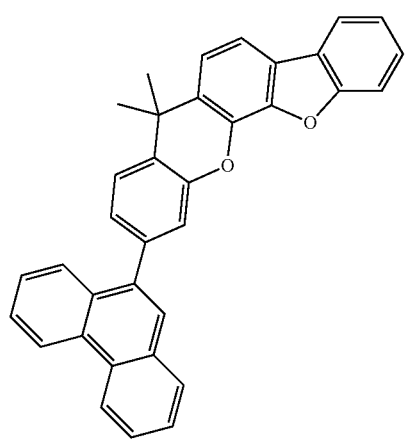
Formula 2-53
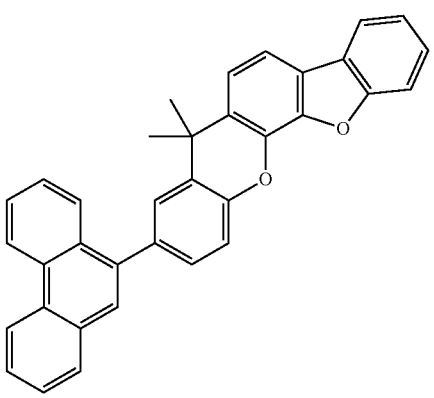
Formula 2-54
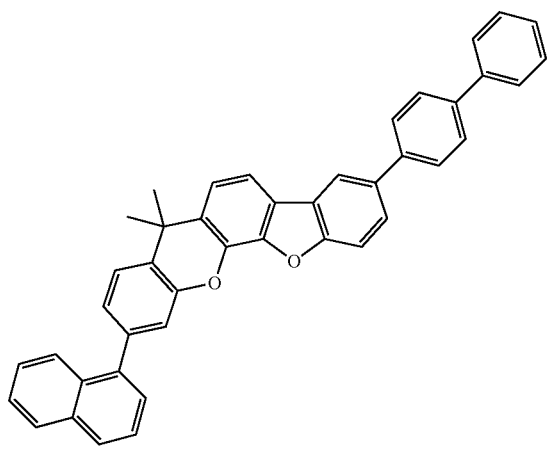
Formula 2-55
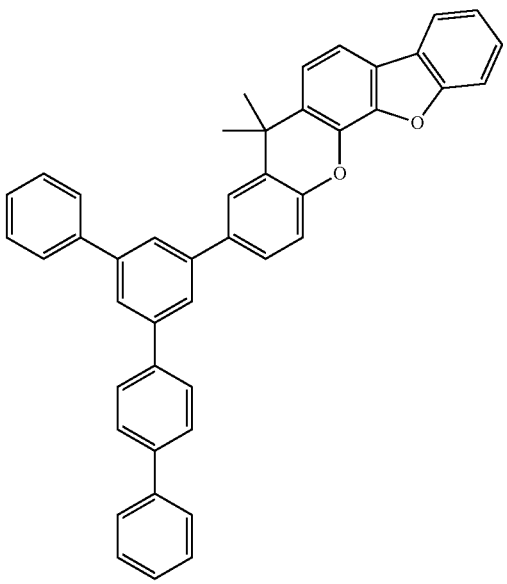

Formula 2-56
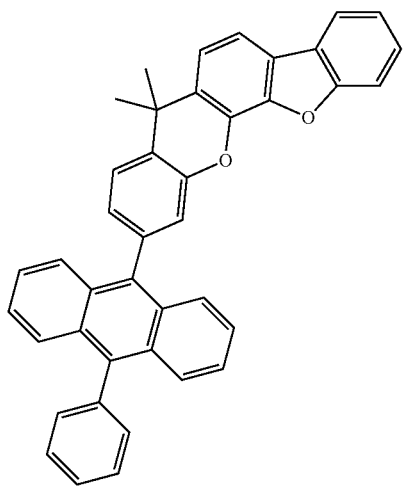
Formula 2-57
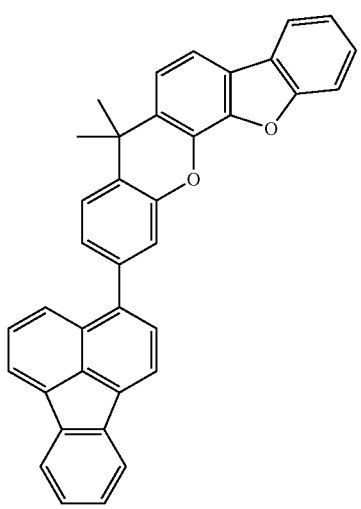
Formula 2-58
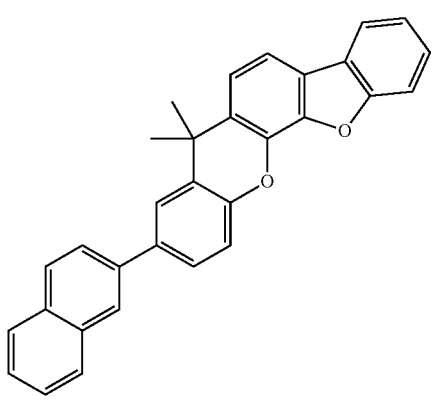
Formula 2-59
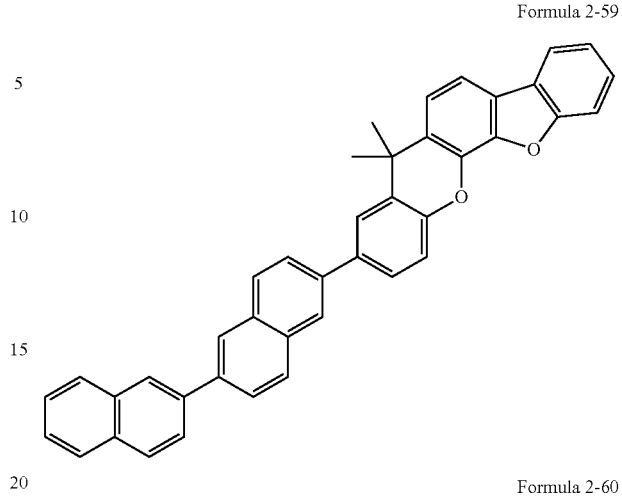
Formula 2-60
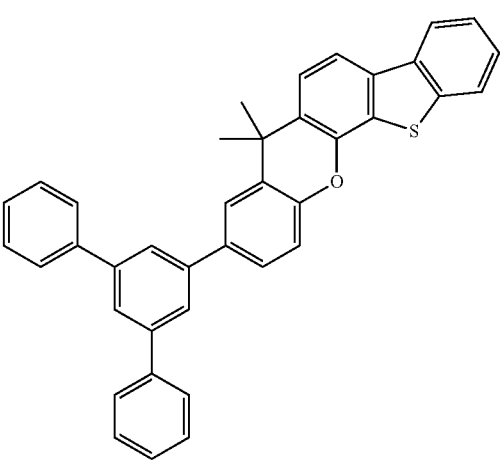
Formula 2-61
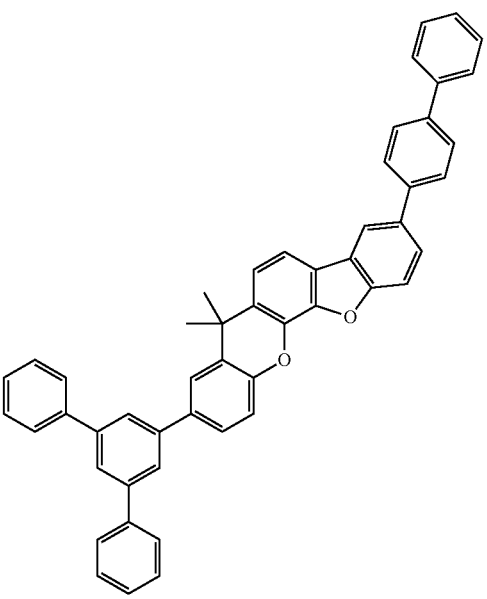

Formula 2-62
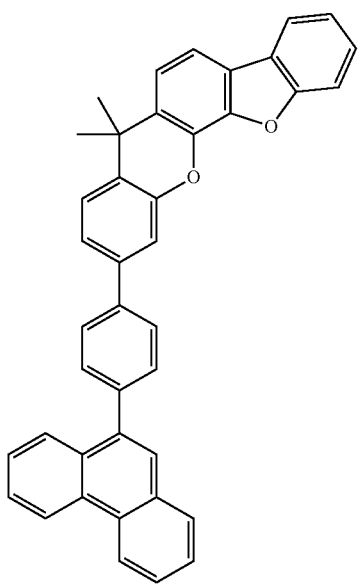
Formula 2-65
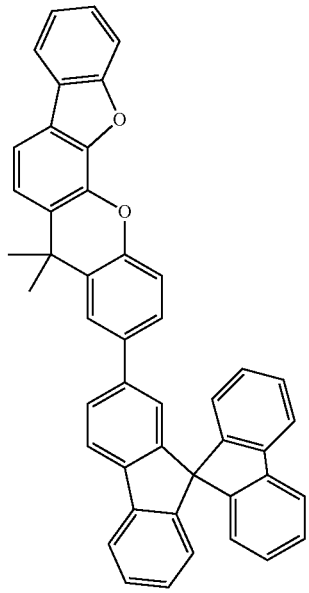
Formula 2-63
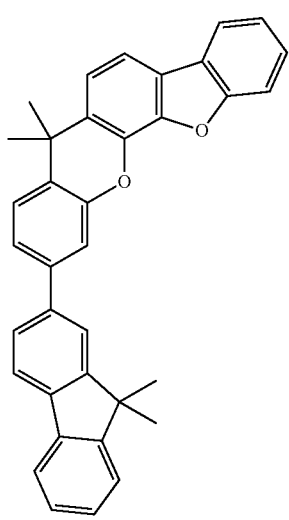
Formula 2-66
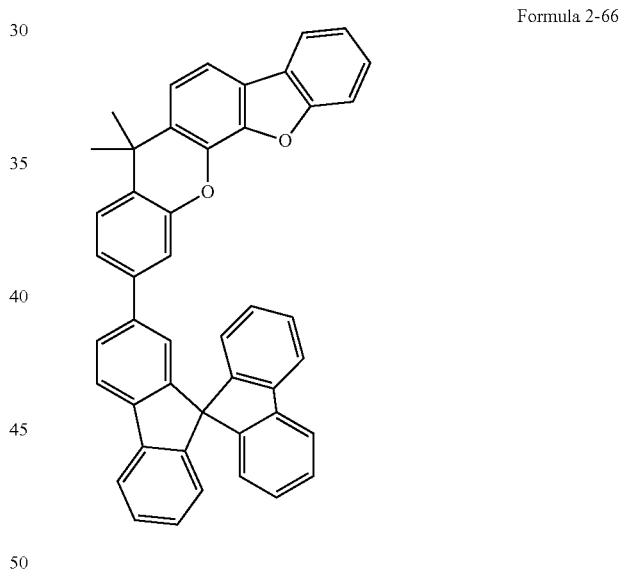
Formula 2-64
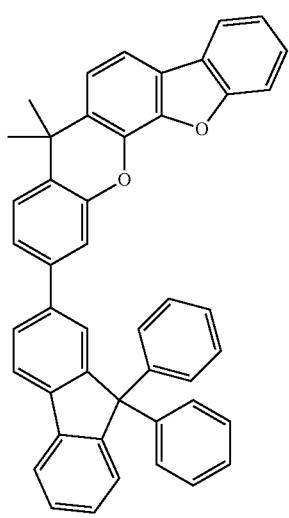
Formula 2-67
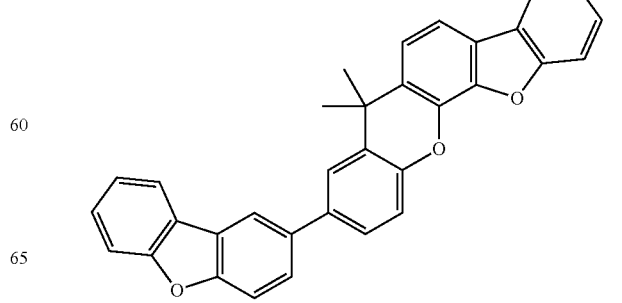

97
-continued
Formula 2-68
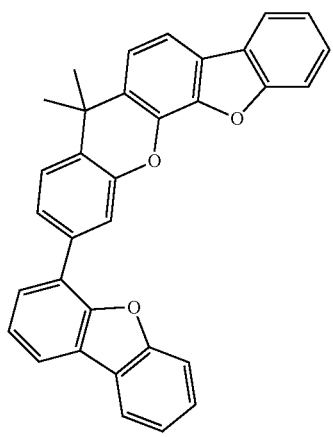
Formula 2-69
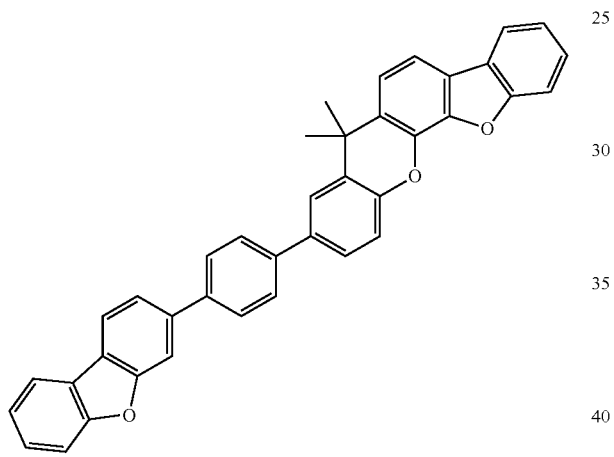
Formula 2-70
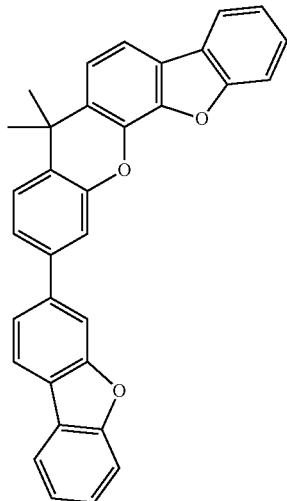
98
-continued
Formula 2-71
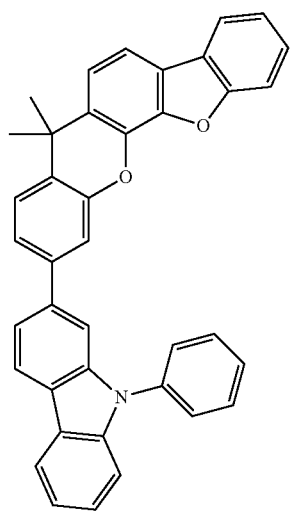
Formula 2-72
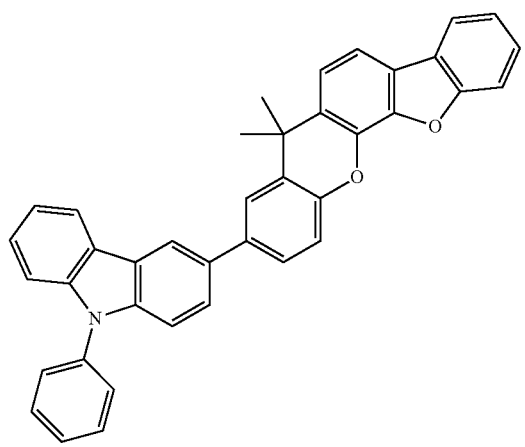
Formula 2-73
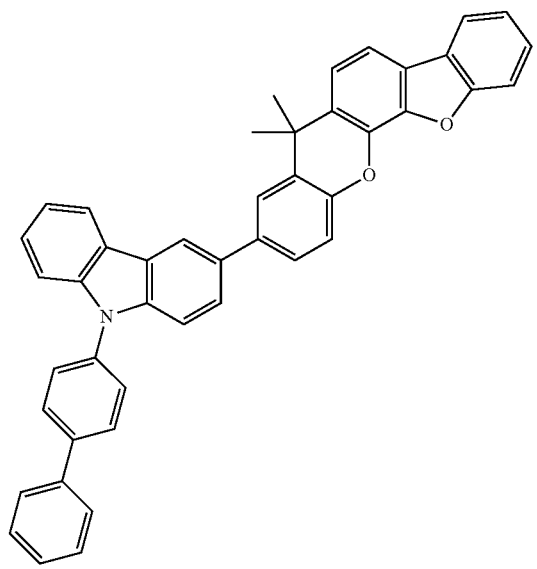

Formula 2-74
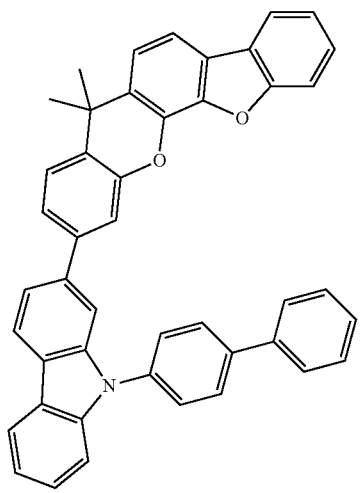
Formula 2-75
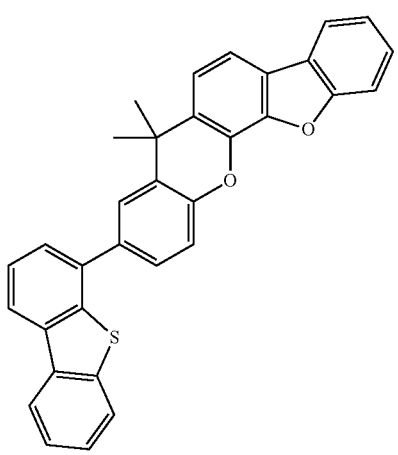
Formula 2-76
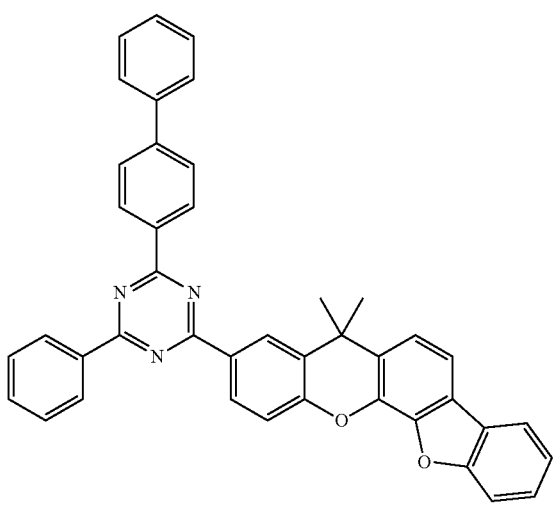
Formula 2-77
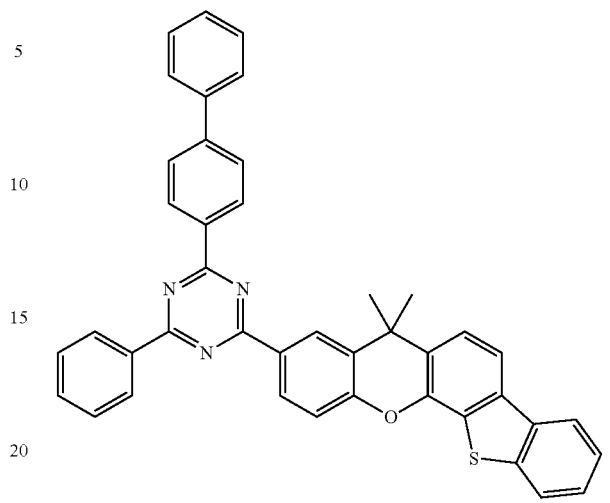
Formula 2-78
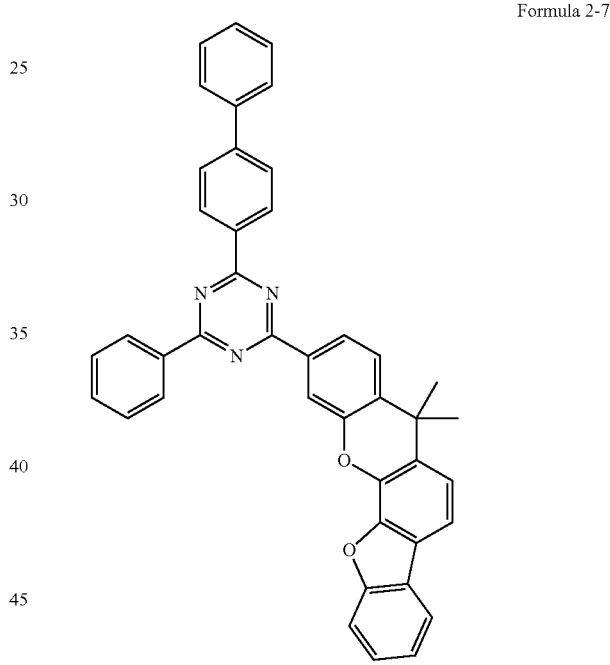
Formula 2-79
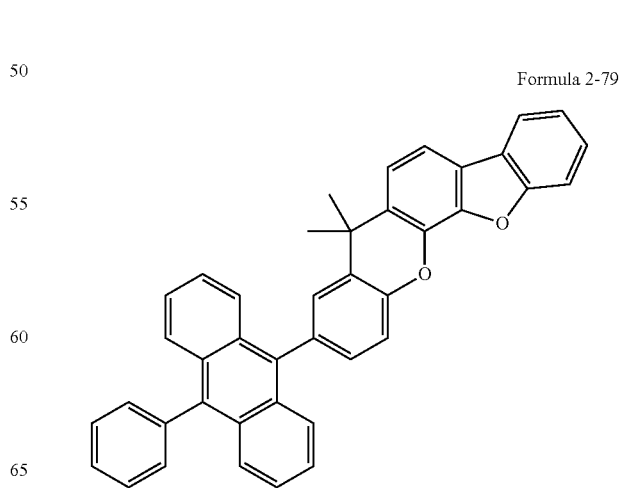

-continued

Formula 2-80

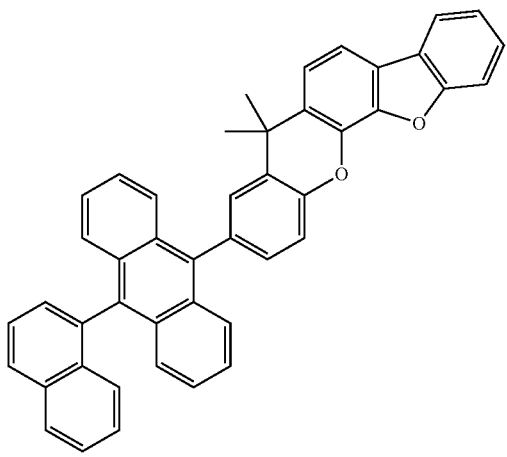

Formula 2-81

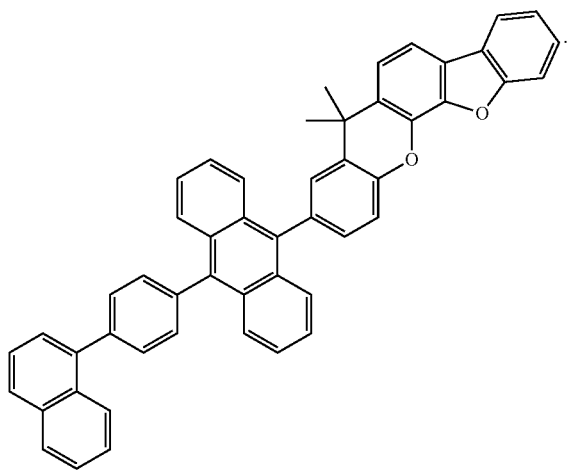

8. An organic light emitting device comprising:
   a first electrode;
   a second electrode provided to face the first electrode; and
   one or more organic material layers comprising a light emitting layer provided between the first electrode and the second electrode,
   wherein one or more layers of the organic material layers comprise the hetero-cyclic compound of claim 1.

9. The organic light emitting device of claim 8, wherein the organic material layer comprises an electron transporting layer, an electron injection layer or a layer which simultaneously transports and injects electrons, and
   the electron transporting layer, the electron injection layer or the layer which simultaneously transports and injects electrons comprises the hetero-cyclic compound.

10. The organic light emitting device of claim 8, wherein the organic material layer comprises a hole transporting layer, a hole injection layer or a layer which simultaneously injects and transports holes, and
    the hole transporting layer, the hole injection layer or the layer which simultaneously injects and transports holes comprises the hetero-cyclic compound.

11. The organic light emitting device of claim 8, wherein the light emitting layer comprises the hetero-cyclic compound.

12. The organic light emitting device of claim 11, wherein the hetero-cyclic compound is a light emitting host.

13. The organic light emitting device of claim 8, wherein the organic material layer further comprises one or two or more layers selected from the group consisting of a hole injection layer, a hole transporting layer, an electron blocking layer, a charge generation layer, a hole blocking layer, an electron transporting layer, and an electron injection layer.

* * * * *